US012708627B2

(12) United States Patent
Nassar et al.

(10) Patent No.: US 12,708,627 B2
(45) Date of Patent: Aug. 18, 2026

(54) COMBINATION THERAPY FOR VAV3 CANCER

(71) Applicants: Children's Hospital Medical Center, Cincinnati, OH (US); UNIVERSITY OF CINCINNATI, Cincinnati, OH (US)

(72) Inventors: Nicolas Nassar, Cincinnati, OH (US); Jose A. Cancelas, Cincinnati, OH (US)

(73) Assignees: Children's Hospital Medical Center, Cincinnati, OH (US); UNIVERSITY OF CINCINNATI, Cincinnati, OH (US)

(*) Notice: Subject to any disclaimer, the term of this patent is extended or adjusted under 35 U.S.C. 154(b) by 305 days.

(21) Appl. No.: 18/681,723

(22) PCT Filed: Aug. 9, 2022

(86) PCT No.: PCT/US2022/039790

§ 371 (c)(1),
(2) Date: Feb. 6, 2024

(87) PCT Pub. No.: WO2023/018688

PCT Pub. Date: Feb. 16, 2023

(65) Prior Publication Data

US 2024/0335449 A1 Oct. 10, 2024

Related U.S. Application Data

(60) Provisional application No. 63/231,035, filed on Aug. 9, 2021.

(51) Int. Cl.

| | |
|---|---|
| ***A61K 31/53*** | (2006.01) |
| ***A61K 31/341*** | (2006.01) |
| ***A61K 31/4184*** | (2006.01) |
| ***A61K 31/444*** | (2006.01) |
| ***A61K 31/5025*** | (2006.01) |
| ***A61P 35/02*** | (2006.01) |

(52) U.S. Cl.

CPC ............ *A61K 31/53* (2013.01); *A61K 31/341* (2013.01); *A61K 31/4184* (2013.01); *A61K 31/444* (2013.01); *A61K 31/5025* (2013.01); *A61P 35/02* (2018.01)

(58) Field of Classification Search

CPC ...................................................... A61K 31/53
USPC ......................................................... 514/246
See application file for complete search history.

(56) References Cited

U.S. PATENT DOCUMENTS

| | | | | |
|---|---|---|---|---|
| 2002/0095039 | A1 | 7/2002 | Cupps et al. | |
| 2002/0107196 | A1 | 8/2002 | Gupta | |
| 2013/0345268 | A1 | 12/2013 | Ratner et al. | |
| 2020/0345712 | A1* | 11/2020 | Nassar | A61K 31/444 |

FOREIGN PATENT DOCUMENTS

| | | | |
|---|---|---|---|
| CN | 102264720 | A | 11/2011 |
| CN | 104586832 | A | 5/2015 |
| WO | 00/66112 | A1 | 11/2000 |
| WO | 2011/058139 | A1 | 5/2011 |
| WO | 2015/175846 | A2 | 11/2015 |
| WO | 2016/077793 | A1 | 5/2016 |

OTHER PUBLICATIONS

International Search Report and Written Opinion for PCT/US2022/039790 mailed Oct. 11, 2022.

International Search Report and Written Opinion dated Sep. 4, 2020 for Application No. PCT/US2020/031298, 21 pgs.

Canadian Office Action dated Nov. 29, 2023 for Application No. CA 3,138,876, 4 pgs.

Chinese Office Action, Notification of the First Office Action and Preliminary Search Report dated Jun. 29, 2023 for Application No. CN 2020800478233, 11 pgs.

European Supplementary Search Report and Written Opinion dated Nov. 23, 2022 for Application No. EP 20802505.6, 9 pgs.

Indian Examination Report dated Nov. 8, 2023 for Application No. IN 202117050783, 7 pgs.

Aguilar, H., et al., "VAV3 mediates resistance to breast cancer endocrine therapy," Breast Cancer Res, 2014, 16:R53, 16 pgs.

Anastassiadis, T., et al., "Comprehensive assay of kinase catalytic activity reveals features of kinase inhibitor selectivity," Nat Biotechnol, 2012, 29(11):1039-1045, 19 pgs.

Aoki, Y., et al., "Recent advances in RASopathies" J Hum Genet, 2016, 61:33-39, 7 pgs.

Araki, M., et al., "Solution Structure of the State 1 Conformer of GTP-bound H-Ras Protein and Distinct Dynamic Properties between the State 1 and State 2 Conformers," J Biol Chem, 2011, 286(45):39644-39653, 10 pgs.

Arrigoni, E. et al. "Concise Review: Chronic Myeloid Leukemia: Stem Cell Niche and Response to Pharmacologic Treatment," Stem Cells Transl Med, 2018, 7:305-314, 10 pgs.

Azam, M., et al., "Mechanisms of Autoinhibition and STI-571/Imatinib Resistance Revealed by Mutagenesis of BCR-ABL," Cell, 2003, 112:831-843, 13 pgs.

Bar-Sagi, D., et al., "Ras and Rho GTPases: A Family Reunion," Cell, 2000, 103(2):227-238, 12 pgs.

Bassermann, F., et al., "Association of Bcr-Abl with the Proto-oncogene Vav Is Implicated in Activation of the Rac-1 Pathway," J Biol Chem, 2002, 277(14):12437-12445, 9 pgs.

Basu, T.N., et al. "Aberrant regulation of ras proteins in malignant tumour cells from type 1 neurofibromatosis patients," Nature, 1992, 356:713-715, 3 pgs.

(Continued)

*Primary Examiner* — Niloofar Rahmani
(74) *Attorney, Agent, or Firm* — FBT Gibbons LLP; Nicole M. Tepe

(57) ABSTRACT

Disclosed herein are compositions and methods for treating an individual having a leukemia. In certain aspects, the methods may include administering an IODVA1 compound and ponatinib to an individual in need thereof for treatment of a leukemia, which may include, for example, TKI-resistant leukemia, TKI-resistant Ph+ B-ALL, Chronic Myelogenous Leukemia (CML), Ph-Positive Acute Lymphoblastic Leukemia (ALL), Ph-like ALL, Resistant Chronic Phase Chronic Myeloid Leukemia (CP-CML), MLL-rearranged B-ALL, and VAV3 positive leukemia.

9 Claims, 51 Drawing Sheets

Specification includes a Sequence Listing.

(56) References Cited

OTHER PUBLICATIONS

Bavetsias, V., et al., "Optimization of Imidazo[4,5-b]pyridine-Based Kinase Inhibitors: Identification of a Dual FLT3/Aurora Kinase Inhibitor as an Orally Bioavailable Preclinical Development Candidate for the Treatment of Acute Myeloid Leukemia," J Med Chem, 2012, 55:8721-8734, 14 pgs.
Berridge, M.V., et al., "Tetrazolium dyes as tools in cell biology: New insights into their cellular reduction," Biotechnol Annu Rev, 2005, 11:127-152, 26 pgs.
Biesiada, J., et al., "Survey of public domain software for docking simulations and virtual screening," Hum Genomics, 2011, 5(5):497-505, 9 pgs.
Biswas, M., et al., "MBD3/NuRD loss participates with KDM6A program to promote DOCK5/8 expression and Rac GTPase activation in human acute myeloid leukemia," FASEB J, 2019, 33:5268-5286, 19 pgs.
Bixby, D., et al., "Mechanisms of resistance to tyrosine kinase inhibitors in chronic myeloid leukemia and recent therapeutic strategies to overcome resistance," Hematology, 2009, 461-476, 16 pgs.
Boriack-Sjodin, P.A., et al., "The structural basis of the activation of Ras by Sos," Nature, 1998, 394:337-343, 7 pgs.
Bos, J.L., "ras Oncogenes in Human Cancer: A Review," Cancer Res, 1989, 49:4682-4689, 8 pgs.
Bos, J.L., et al., "GEFs and GAPs: Critical Elements in the Control of Small G Proteins," Cell, 2007, 129:865-877, 13 pgs.
Bourgoin, S., et al., "Low Molecular Weight GTP-binding Proteins in HL-60 Granulocytes. Assessment of the Role of ARF and of a 50-kDa Cytosolic Protein in Phospholipase D Activation," J Biol Chem, 1995, 270(7):3172-3178, 7 pgs.
Bustelo, X.R. Rho GTPases in Cancer: known facts, open questions, and therapeutic challenges. *Biochem Soc Trans* 46, 741-760 (2018).
Cardama, G.A., et al., "Relevance of small GTPase Racl pathway in drug and radio-resistance mechanisms: Opportunities in cancer therapeutics," Crit Rev Oncol/Hematol, 2018, 124:29-36, 8 pgs.
Cardarella, S., et al., "The Impact of Genomic Changes on Treatment of Lung Cancer," Am J Respir Crit Care Med, 2013, 188(7):770-775, 6 pgs.
Carpino, N., Chen, Y., Nassar, N. & Oh, H.W. The Sts proteins target tyrosine phosphorylated, ubiquitinated proteins within TCR signaling pathways. Mc)/ Immunol 46, 3224-31 (2009).
Carpino, N. et al. Identification, cDNA cloning, and targeted deletion of p70, a novel, ubiquitously expressed SH3 domain-containing protein. Mol Cell Biol 22, 7491-500 (2002).
Chang, K.H. et al. Vav3 collaborates with p190-BCR-ABL in lymphoid progenitor leukemogenesis, proliferation, and survival. *Blood* 120, 800-11 (2012).
Chardin, P., et al., "Human Sos1: A Guanine Nucleotide Exchange Factor for Ras That Binds to GRB2," Science, 1993, 260:1338-1343, 6 pgs.
Chatterjee, S.S., et al., "SMARCB1 Deficiency Integrates Epigenetic Signals to Oncogenic Gene Expression Program Maintenance in Human Acute Myeloid Leukemia," Mol Cancer Res, 2018, 16(5):791-804, 14 pgs.
Chen, X. et al. Determination of the substrate specificity of protein-tyrosine phosphatase TULA-2 and identification of Syk as a TULA-2 substrate. The Journal of Biological Chemistry 285, 31268-76 (2010).
Chen, Yuxiang, ed., Molecular Pharmaceutics. Hunan Normal University Press, Changsha, Hunan, China, Jan. 31, 2010, pp. 2-5, [English & Chinese language versions included.], 13 pgs.
Chen, Y., Jakoncic, J., Carpino, N. & Nassar, N. Structural and Functional Characterization of the 2H-Phosphatase Domain of Sts-2 Reveals an Acid-Dependent Phosphatase Activity (dagger). Biochemistry (2009).
Chen, Y. et al. Structural and functional characterization of the c-terminal domain of the ecdysteroid phosphate phosphatase from bombyx mori reveals a new enzymatic activity. Biochemistry 47, 12135-45 (2008).
Chen, Y., Jakoncic, J., Parker, K.A., Carpino, N. & Nassar, N. Structures of the phosphorylated and VO(3)-bound 2H-phosphatase domain of Sts-2. Biochemistry 48, 8129-35 (2009).
Chen, X., et al., "Vav3 oncogene is upregulated and a poor prognostic factor in breast cancer patients," Oncol Lett, 2015, 9:2143-2148, 6 pgs.
Cheng, T., et al., "Structure-Based Virtual Screening for Drug Discovery: a Problem-Centric Review," AAPS J, 2012, 14(1):133-141, 9 pgs.
Cilloni, D., et al., "Molecular Pathways: BCR-ABL," Clin Cancer Res, 2012, 18:930-937, 8 pgs.
Citterio, C., et al., "The Rho Exchange Factors Vav2 and Vav3 Control a Lung Metastasis-Specific Transcriptional Program in Breast Cancer Cells," Sci Signal, 2012, 5(244):ra71, 16 pgs.
Coleman, M.L., et al., "RAS and RHO GTPases in G1-Phase Cell-Cycle Regulation," Nat Rev Mol Cell Biol, 2004, 5:355-366, 12 pgs.
Condeelis, J., et al., "The Great Escape: When Cancer Cells Hijack the Genes for Chemotaxis and Motility," Annu Rev Cell Dev Biol, 2005, 21:695-718, 27 pgs.
Corsello, S.M., et al., "The Drug Repurposing Hub: a next-generation drug library and information resource," Nat Med, 2017, 23(4):405-408, 11 pgs.
Cox, A.D., et al., "Drugging the undruggable RAS: mission possible?" Nat Rev Drug Discov, 2014, 13(11):828-851, 47 pgs.
Dar, A.C., Das, T.K., Shokat, K.M. & Cagan, R.L. Chemical genetic discovery of targets and anti-targets for cancer polypharmacology. Nature 486, 80-4 (2012).
De Melo, M., et al., "Phosphorylated Extracellular Signal-Regulated Kinases Are Significantly Increased in Malignant Mesothelioma," J Histochem Cytochem, 2006, 54(8):855-861, 7 pgs.
Declue, J.E., et al., "Abnormal Regulation of Mammalian p21$^{ras}$ Contributes to Malignant Tumor Growth in von Recklinghausen (type 1) Neurofibromatosis," Cell, 1992, 69:265-273, 9 pgs.
Denizot, F., et al., "Rapid colorimetric assay for cell growth and survival: Modifications to the tetrazolium dye procedure giving improved sensitivity and reliability," J Immunol Methods, 1986, 89:271-277, 7 pgs.
Downward, J., "Targeting RAS Signalling Pathways in Cancer Therapy," Nat Rev Cancer, 2003, 3:11-22, 12 pgs.
Doyle, M.L., et al., "Selective Binding and Oligomerization of Murine Granulocyte Colony-stimulating Factor Receptor by a Low Molecular Weight, Nonpeptidyl Ligand," J Biol Chem, 2003, 278(11):9426-9434, 9 pgs.
Espina, C., et al., "A Critical Role for Racl in Tumor Progression of Human Colorectal Adenocarcinoma Cells," Am J Pathol, 2008, 172(1):156-166, 11 pgs.
Etienne-Manneville, S., et al., "Rho GTPases in cell biology," Nature, 2002, 420:629-635, 7 pgs.
Euhus, D.M., et al., "Tumor Measurement in the Nude Mouse," Journal of Surgical Oncology, 1986, 31:229-234, 4 pgs.
Evelyn, C.R., et al., "Combined Rational Design and a High Throughput Screening Platform for Identifying Chemical Inhibitors of a Ras-activating Enzyme," J Biol Chem, 2015, 290(20):12879-12898, 20 pgs.
Evelyn, C.R., et al., "Rational design of small molecule inhibitors targeting the Ras GEF, SOS1," Chem Biol, 2014, 21(12):1618-1628, 23 pgs.
Fei, Y. et al. Identification of novel genetic susceptibility loci for Behcet's disease using a genome-wide association study. Arthritis research & therapy 11, R66 (2009).
Feshchenko, E.A. et al., TULA: an SH3-and UBA-Containing Protein that binds to c-Cbl and Ubiquitin. Oncogene 23, 4690-706 (2004).
Fife, C.M., et al., "Movers and shakers: cell cytoskeleton in cancer metastasis," Br J Pharmacol, 2014, 171:5507-5523, 17 pgs.
Ford, B., et al., "Structure of the G60A Mutant of Ras: Implications for the Dominant Negative Effect," J Biol Chem, 2005, 280(27):25697-25705, 9 pgs.
Ford, B.A., et al., "Characterization of a Ras mutant with identical GDP-and GTP-bound structures," Biochemistry, 2009, 48(48):11449-11457, 21 pgs.

(56) References Cited

OTHER PUBLICATIONS

Foty, R., "A Simple Hanging Drop Cell Culture Protocol for Generation of 3D Spheroids," JoVE, 2011, 51, 4 pgs.
Foulkes, W.D., Smith, I.E. & Reis-Filho, J.S. "Triple-negative Breast Cancer." N Engl J med 363, 1938-48 (2010).
Fujikawa, K., et al., "Vav1/2/3-null Mice Define an Essential Role for Vav Family Proteins in Lymphocyte Development and Activation but a Differential Requirement in MAPK Signaling in T and B Cells," J Exp Med, 2003, 198(10):1595-1608, 14 pgs.
Gasilina, A. et al. IODVA1, a guanidinobenzimidazole derivative, targets Rac activity and Ras-driven cancer models. *PLoS One* 15, e0229801 (2020).
Gatti, A., Huang, Z., Tuazon, P.T. & Traugh, J.A. Multisite autophosphorylation of p21-activated protein kinase gamma-PAK as a function of activation. *J Biol Chem* 274, 8022-8 (1999).
Gennaro, A.R., (ed.), Remington: The Science and Practice of Pharmacy, $19^{th}$ Ed., 1995, Mack Publishing Company, Easton, Pennsylvania, 6 pgs. (Table of Contents Only).
Gennaro, A.R., (ed.), Remington: The Science and Practice of Pharmacy, $20^{th}$ Ed., 2000, Lippincott Williams & Wilkins, Philadelphia, Pennsylvania, 5 pgs. (Table of Contents Only).
Gennaro, A.R., (ed.), Remington's Pharmaceutical Sciences, $18^{th}$ Ed., 1990, Mack Publishing Company, Easton, Pennsylvania, 8 pgs. (Table of Contents Only).
Geyer, M., et al., "Conformational Transitions in $p21^{ras}$ and in Its Complexes with the Effector Protein Raf-RBD and the GTPase Activating Protein GAP," Biochemistry, 1996, 35:10308-10320, 13 pgs.
Gorre, M.E., et al., "Clinical Resistance to STI-571 Cancer Therapy Caused by BCR-ABL Gene Mutation or Amplification," Science, 2001, 293:876-880, 5 pgs.
Green, J., et al., "Design, Synthesis, and Structure-Activity Relationships of Pyridine-Based Rho Kinase (ROCK) Inhibitors," J Med Chem, 2015, 58:5028-5037, 10 pgs.
Gutjar, P., "Design and synthesis of anti cancer agents that inhibit cysteine proteases, limit oxidative stress or terminate proliferation of BCR-ABL expressing cells," Dissertation submitted to the Graduate School of the University of Cincinnati in Partial Fulfillment of the Requirements for the Degree of Doctor of Philosophy (Ph.D.) in the Department of Chemistry, Jul. 2018, 20 pgs.
Hall, A., "Small GTP-Binding Proteins and the Regulation of the Actin Cytoskeleton," Annu Rev Cell Biol, 1994, 10:31-54, 25 pgs.
Hamilton, A., et al., "Chronic myeloid leukemia stem cells are not dependent on Bcr-Abl kinase activity for their survival," Blood, 2012, 119(6):1501-1510, 10 pgs.
Harnois, T. et al. Differential interaction and activation of Rho family GTPases by p210bcr-abl and p190bcr-abl. *Oncogene* 22, 6445-54 (2003).
Hollestelle, A., et al., "Phosphatidylinositol-3-OH Kinase or RAS Pathway Mutations in Human Breast Cancer Cell Lines," Mol Cancer Res, 2007, 5(2):195-201, 7 pgs.
Huey, R., et al., "A Semiempirical Free Energy Force Field with Charge-Based Desolvation," J Comput Chem, 2007, 28:1145-1152, 8 pgs.
Hudis, C.A. & Gianni, L. "Triple-Negative Breast Cancer: an Unmet Medical Need." Oncologist 16 Suppl 1, 1-11 (2011).
Hwang, M.C., et al., "The Differential Effects of the Gly-60 to Ala Mutation on the Interaction of H-Ras p21 with Different Downstream Targets," J Biol Chem, 1996, 271(14):8196-8202, 7 pgs.
Ikeda, F. et al., Involvement of the Ubiquitin-like Domain of TBKI/IKK-I Kinases in Regulation of IFN-Inducible Genes. EMBO J 26, 3451-62 (2007).
Irwin, J.J., et al., "ZINC—A free Database of Commercially Available Compounds for Virtual Screening," J Chem Inf Model, 2005, 45(1):177-182, 11 pgs.
Irwin, J.J., et al., "ZINC: A Free Tool to Discover Chemistry for Biology," J Chem Inf Model, 2012, 52:1757-1768, 12 pgs.
Jabbour, E. et al., "Characteristics and outcomes of patients with chronic myeloid leukemia and T315I mutation following failure of imatinib mesylate therapy," Blood, 2008, 112:53-55, 3 pgs.
Jabbour, E., et al., "Frequency and clinical significance of BCR-ABL mutations in patients with chronic myeloid leukemia treated with imatinib mesylate," Leukemia, 2006, 20:1767-1773, 7 pgs.
Jaffe, A.B., et al., "Rho GTPases: Biochemistry and Biology," Annu Rev Cell Dev Biol, 2005, 21:247-269, 26 pgs.
Jakoncic, J., Sondgeroth, B., Carpino, N. & Nassar, N. The 1.35 A resolution structure of the phosphatase domain of the suppressor of T-cell receptor signaling protein in complex with sulfate. Acta Crystallogr Sect F Struct Biol Cryst Commun 66, 643-7 (2010).
Janes, M.R., et al., "Targeting KRAS Mutant Cancers with a Covalent G12C-Specific Inhibitor," Cell, 2018, 172:578-589, 30 pgs.
Jerabek-Willemsen, M., et al., "Molecular Interaction Studies Using Microscale Thermophoresis," Assay Drug Dev Technol, 2011, 9(4):342-353, 12 pgs.
Jin, Y. et al. Variant of TYR and autoimmunity susceptibility loci in generalized vitiligo. The New England journal of medicine 362, 1686-97 (2010).
Kales, S.C., Ryan, P.E., Nau, M.M. & Lipkowitz, S. Cbl and human myeloid neoplasms: the Cbl oncogene comes of age. Cancer Res 70, 4789-94 (2010).
Kim, Y. et al., "Spectrum of EGFR Gene Copy Number Changes and KRAS Gene Mutation Status in Korean Tiple Negative Breast Cancer Patients" PLoS One 8, e79014 (2013).
Kim, K. et al. High-density genotyping of immune loci in Koreans and Europeans identifies eight new rheumatoid arthritis risk loci. Ann Rheum Dis (2014).
Kiosses, W.B., et al., "Rac recruits high-affinity integrin $\alpha v\beta 3$ to lamellipodia in endothelial cell migration," Nat Cell Biol, 2001, 3:316-320, 5 pgs.
Kissil, J.L., et al. "Requirement for Racl in a K-ras induced Lung Cancer in the Mouse," Cancer Res, 2007, 67(17):8089-8094, 6 pgs.
Knight, Z.A., Lin, H. & Shokat, K.M. Targeting the cancer kinome through polypharmacology. Nat Rev Cancer 10, 130-7 (2010).
Kristelly, R., "Preliminary structure analysis of the DH/PH domains of leukemia-associated RhoGEF," Acta Crystallogr D Biol Crystallogr, 2003, D59:1859-1862, 4 pgs.
Kowanetz, K. et al. Suppressors of T-cell receptor signaling Sts-1 and Sts-2 bind to Cbl and inhibit endocytosis of receptor tyrosine kinases. J Biol Chem 279, 32786-95 (2004).
Lavecchia, A., et al., "Virtual Screening Strategies in Drug Discovery: A Critical Review," Current Medicinal Chemistry, 2013, 20:2839-2860, 22 pgs.
Lee, S.T. et al. Protein tyrosine phosphatase UBASH3B is overexpressed in triplenegative breast cancer and promotes invasion and metastasis. Proc Natl Acad Sci USA 110, 11121-6 (2013).
Lee, L.H. et al. Real-time genomic profiling of histiocytoses identifies early-kinase domain BRAF alterations while improving treatment outcomes. *JCI Insight 2*, e89473 (2017).
Lee, S.H., et al., "Regulation of Actin Cytoskeleton Dynamics in Cells," Mol Cells, 2010, 29(4):311-325, 26 pgs.
Lee, K., et al., "Vav3 oncogene activates estrogen receptor and its overexpression may be involved in human breast cancer," BMC Cancer, 2008, 8:158, 13 pgs.
Levine, A.J., et al., "The Control of the Metabolic Switch in Cancers by Oncogenes and Tumor Suppressor Genes," Science, 2010, 330:1340-1344, 6 pgs.
Li, Y., et al., "Somatic Mutations in the Neurofibromatosis 1 Gene in Human Tumors," Cell, 1992, 69:275-281, 7 pgs.
Lipinski, C.A., et al., "Experimental and computational approaches to estimate solubility and permeability in drug discovery and development settings," Advanced Drug Delivery Reviews, 2001, 46:3-26, 24 pgs.
Loirand, G. & Pacaud, P. The role of Rho protein signaling in hypertension. *Nat Rev Cardiol* 7, 637-47 (2010).
Lorenzo-Martin, L.F., et al., "Vav proteins maintain epithelial traits in breast cancer cells using miR-200c-dependent and independent mechanisms," Oncogene, 2019, 38:209-227, 19 pgs.
Lord, C.J. & Ashworth, A. "Mechanisms of Resistance to Therapies Targeting BRCA-mutant Cancers" Nat Med 19, 1381-8 (2013).
Lounnas, V., et al., "Current Progress in Structure-Based Rational Drug Design Marks a New Mindset in Drug Discovery," Comput Struct Biotechnol J, 2013, 5(6):e201302011, 14 pgs.

(56) References Cited

OTHER PUBLICATIONS

Loveland, B.E., et al., "Validation of the MTT Dye Assay for Enumeration of Cells in Proliferative and Antiproliferative Assays," Biochem Int, 1992, 27(3):501-510, 6 pgs.
Lugo, T.G., et al., "Tyrosine Kinase Activity and Transformation Potency of bcr-abl Oncogene Products," Science, 1990, 247:1079-1082, 4 pgs.
Lyons, R., et al., "The RAC specific guanine nucleotide exchange factor Asef functions downstream from TEL-AML1 to promote leukaemic transformation," Leuk Res, 2010, 34:109-115, 7 pgs.
Mack, N.A., et al., "The diverse roles of Rac signaling in tumorigenesis," Cell Cycle, 2011, 10(10):1571-1581, 11 pgs.
Mahller, Y.Y., et al., "Malignant Peripheral Nerve Sheath Tumors with High and Low Ras-GTP are Permissive for Oncolytic Herpes Simplex Virus Mutants," Pediatr Blood Cancer, 2006, 46:745-754, 10 pgs.
Malliri, A., et al., "Mice deficient in the Rac activator Tiaml are resistant to Ras-induced skin tumours," Nature, 2002, 417(6891):867-871, 5 pgs.
Marei, H., et al., "GEFs: Dual regulation of Rac1 signaling," Small GTPases, 2017, 8(2):90-99, 10 pgs.
Marin-Ramos, N.I., et al., "Blocking Ras inhibition as an antitumor strategy," Semin Cancer Biol, 2019, 54:91-100, 10 pgs.
Martin, H., et al., "Pak and Rac GTPases promote oncogenic KIT-induced neoplasms," J Clin Invest, 2013, 123(10):4449-4463, 15 pgs.
Maurer, T., et al., "Small-molecule ligands bind to a distinct pocket in Ras and inhibit SOS-mediated nucleotide exchange activity," PNAS USA, 2012, 109(14):5299-5304, 6 pgs.
Mccormick, F., "K-Ras protein as a drug target," J Mol Med, 2016, 94:253-258, 6 pgs.
Mckim, A.S., et al., "Dimethyl Sulfoxide USP, PhEur in Approved Pharmaceutical Products and Medical Devices," Pharmaceutical Technology, 2008, 32(5), 7 pgs.
Mestres, J., Gregori-Puigjane, E., Valverde, S. & Sole, R.V. The topology of drug-target interaction networks: implicit dependence on drug properties and target families. Mol Biosyst 5, 1051-7 (2009).
Mikhailik, A. et al. A phosphatase activity of Sts-1 contributes to the suppression of TCR signaling. Mol Cell 27, 486-97 (2007).
Milojkovic, D., et al., "Mechanisms of Resistance to Imatinib and Second-Generation Tyrosine Inhibitors in Chronic Myeloid Leukemia," Clin Cancer Res, 2009, 15(24):7519-7527, 9 pgs.
Minden, A., et al., "Selective Activation of the JNK Signaling Cascade and c-Jun Transcriptional Activity by the Small GTPases Rac and Cdc42Hs," Cell, 1995, 81:1147-1157, 11 pgs.
Mizukawa, B. et al. Inhibition of Rac GTPase signaling and downstream prosurvival Bcl-2 proteins as combination targeted therapy in MLL-AF9 leukemia. *Blood* 118, 5235-45 (2011).
Morris, G.M., et al., "Automated Docking Using a Lamarckian Genetic Algorithm and an Empirical Binding Free Energy Function," J Computational Chemistry, 1998, 19(14):1639-1662, 24 pgs.
Morris, G.M., et al., "AutoDock4 and AutoDockTools4: Automated Docking with Selective Receptor Flexibility," J Comput Chem, 2009, 30(16):2785-2791, 12 pgs.
Mulloy, J.C., et al., "Rho GTPases in hematopoiesis and hemopathies," Blood, 2010, 115(5):936-947, 12 pgs.
Nassar, Nicolas et al., "The Small Molecule IODVA1 Inhibits the Rac Guanine Nucleotide Exchange Factor Vav3 and Overcomes TKI-Resistance in Ph+(BCR-ABL1) B-ALL", Blood, American Society of Hematology, US, vol. 134, Nov. 13, 2019 (Nov. 13, 2019), p. 4647, XP086669051, ISSN: 0006-4971, DOI: 10.1182/BLOOD-2019-130250 pp. 1-2.
Newey, S.E., Velamoor, V., Govek, E.E. & Van Aelst, L. Rho GTPases, dendritic structure, and mental retardation. *J Neurobiol* 64, 58-74 (2005).
Nicolini, F.E., et al., "Mutation status and clinical outcome of 89 imatinib mesylate-resistant chronic myelogenous leukemia patients: a retrospective analysis from the French intergroup of CML (Fi(φ)-LMC Group)," Leukemia, 2006, 20:1061-1066, 6 pgs.
Nieborowska-Skorska, M. et al. Rac2-MRC-cIII-generated ROS cause genomic instability in chronic myeloid leukemia stem cells and primitive progenitors. *Blood* 119, 4253-63 (2012).
Nishimura, T., et al., "Reaction of Guanidines with α-Diketones, Syntheses of 4,5-Disubstituted-2-aminoimidazoles and 2.6-Unsymmetrically Substituted Imidazo[4,5-d]imidazoles," J Org Chem, 1979, 44(5):818-824, 7 pgs.
Nouri, K. et al. IQGAP1 Interaction with RHO Family Proteins Revisited: Kinetic and Equilibrium Evidence for Multiple Distinct Binding Sites. *J Biol Chem* 291, 26364-26376 (2016).
Olson, M.F., et al., "The actin cytoskeleton in cancer cell motility," Clin Exp Metastasis, 2009, 26:273-287, 15 pgs.
Ostrem, J.M.L., et al., "Direct small-molecule inhibitors of KRAS: from structural insights to mechanism-based design," Nat Rev Drug Discov, 2006, 15:771-785, 15 pgs.
Pai, E.F., et al., "Structure of the guanine-nucleotide-binding domain of the Ha-ras oncogene product p21 in the triphosphate conformation," Nature, 1989, 341:209-214, 6 pgs.
Park, H.S. et al. High EGFR gene copy number predicts poor outcome in triple-negative breast cancer. Mod Pathol (2014).
Peddi, P. F., Ellis, M.J. & Ma, C. "Molecular Basis for Triple Negative Breast Cancer and Implications for Therapy." Int J Breast Cancer 2012, 217185 (2012).
Plagnol, V. et al. Genome-wide association analysis of autoantibody positivity in type 1 diabetes cases. PLoS genetics 7, e1002216 (2011).
Porter, A.P., et al., "Deregulation of Rho GTPases in cancer," Small GTPases, 2016, 7(3):123-138, 16 pgs.
PubChem, Compound Summary, 5-(4-Chlorophenyl)-3-[(E)-2-(4-chlorophenyl)-2-phenylethney1]-5-phenyloxolan-2-one, PubChem CID: 6514822, Created May 3, 2006, Modified Jun. 13, 2020, 8 pgs.
PubChem, Substance Record, NSC-124205, PubChem SID: 417201, Deposited Mar. 26, 2005, Modified: Dec. 19, 2011, 8 pgs.
Pui, C.H., Roberts, K.G., Yang, J.J. & Mullighan, C.G. Philadelphia Chromosome-like Acute Lymphoblastic Leukemia. *Clin Lymphoma Myeloma Leuk* 17, 464-470 (2017).
Qu, Y., et al., "Antitumor activity of selective MEK1/2 inhibitor AZD6244 in combination with PI3K/mTOR inhibitor BEZ235 in gefitinib-resistant NSCLC xenograft models," J Exp Clin Cancer Res, 2014, 33:52, 10 pgs.
Quevedo, C.E., et al., "Small molecule inhibitors of RAS-effector protein interactions derived using an intracellular antibody fragment," Nature Communications, 2018, 9:3169, 12 pgs.
Qui, R.G., et al., "An essential role for Rac in Ras transformation," Nature, 1995, 374:457-459, 3 pgs.
Raguz, J., Wagner, S., Dikic, I. & Hoeller, D. Suppressor of T-cell receptor signalling 1 and 2 differentially regulate endocytosis and signaling of receptor tyrosine kinases. FEBS Lett 581, 4767-72 (2007).
Rakha, E.A., & Chan, S. "Metastatic Triple-Negative Breast Cancer." Clin Oncol (R CollRadiol) 23, 587-600 (2011).
Rauen, K.A., "The RASopathies," Annu Rev Genomics Hum Genet, 2013, 14:355-369, 20 pgs.
Reis-Filho, J.S et al. EGFR amplification and lack of activating mutations in metaplastic breast carcinomas. J Pathol 209, 445-53 (2006).
Reuther, G.W., et al., "Leukemia-associated Rho Guanine Nucleotide Exchange Factor, a Dbl Family Protein Found Mutated in Leukemia, Causes Transformation by Activation of RhoA," J Biol Chem, 2001, 276(29):27145-27151, 7 pgs.
Riad El Fakih et al., "Current Paradigms in the Management of Philadelphia Chromosome Positive Acute Lymphoblastic Leukemia in Adults", American Journal of Hematology, New York, NY, US, vol. 93, No. 2, Oct. 31, 2017 (Oct. 31, 2017), pp. 286-295, XP071632050, ISSN: 0361-8609, DOI: 10.1002/AJH.24926 page Section—p. 2.3.
Ridley, A.J. Rho GTPase signaling in cell migration. *Curr Opin Cell Biol* 36, 103-12 (2015).
Ridley, A.J., et al., "The Small GTP-Binding Protein rac Regulates Growth Factor-Induced Membrane Ruffling," Cell, 1992, 70:401-410, 10 pgs.

(56) References Cited

OTHER PUBLICATIONS

Ridley, A.J., et al., "The Small GTP-Binding Protein rho Regulates the Assembly of Focal Adhesions and Actin Stress Fibers in Response to Growth Factors," Cell, 1992, 70(3):389-399, 11 pg.
Roberts, A.E., et al., "Germline gain-of-function mutations in SOS1 cause Noonan syndrome," Nat Genet, 2007, 39(1):70-74, 5 pgs.
Roberts, K.G. & Mullighan, C.G. Genomics in acute lymphoblastic leukaemia: insights and treatment implications. *Nat Rev Clin Oncol* 12, 344-57 (2015).
Rojas, J.M., et al., "Mammalian Son of Sevenless Guanine Nucleotide Exchange Factors: Old Concepts and New Perspectives," Genes & Cancer, 2011, 2(3):298-305, 8 pgs.
Rolfo, C., et al., "Novel therapeutic strategies for patients with NSCLC that do not respond to treatment with EGFR inhibitors," Cancer Treat Rev, 2014, 40:990-1004, 15 pgs.
Rouard, H., et al., "Vav and SLP-76 recruitment by cross-linking of FcγRIIa1 in promyelocytic HL-60 cells," Immunol Lett, 1999, 68:347-353, 7 pgs.
Saci, A., et al., "Rac1 Regulates the Activity of mTORC1 and mTORC2 and Controls Cellular Size," Mol Cell, 2011, 42(1):50-61, 22 pgs.
Sahai, E., et al., "RHO-GTPases and Cancer," Nat Rev Cancer, 2002, 2:133-142, 11 pgs.
Sahai, E., "Mechanisms of cancer cell invasion," Curr Opin Genet Dev, 2005, 15:87-96, 10 pgs.
Sahay, S. et al. The RhoGEF domain of p210 Bcr-Abl activates RhoA and is required for transformation. *Oncogene* 27, 2064-71 (2008).
San Luis, B., Sondgeroth, B., Nassar, N. & Carpino, N. Sts-2 is a phosphatase that negatively regulates zeta-associated protein (ZAP)-70 and T cell receptor signaling pathways. The Journal of biological chemistry 286, 15943-54 (2011).
Schopel, M., et al., "Bisphenol A Binds to Ras Proteins and Competes with Guanine Nucleotide Exchange: Implications for GTPase-Selective Antagonists," J Med Chem, 2013, 56:9664-9672, 9 pgs.
Sengupta, A., et al., "Rac2 GTPase deficiency depletes BCR-ABL$^+$ leukemic stem cells and progenitors in vivo," Blood, 2010, 116(1):81-84, 4 pgs.
Shah, S.P., et al., "The Clonal and Mutational Evolution Spectrum of Primary Triple-Negative Breast Cancers." Nature 486, 395-9 (2012).
Shima, F., et al., "Structural Basis for Conformational Dynamics of GTP-bound Ras Protein," J Biol Chem, 2010, 285(29):22696-22705, 10 pgs.
Shima, F., et al., "In silico discovery of small-molecule Ras inhibitors that display antitumor activity by blocking the Ras-effector interaction," PNAS USA, 2013, 110(20):8182-8187, 6 pgs.
Siegel, R., et al. "Cancer Statistics, 2013," CA Cancer J Clin, 2013, 63:11-30, 20 pgs.
Simanshu, D.K., et al., "RAS Proteins and Their Regulators in Human Disease," Cell, 2017, 170(1):17-33, 34 pgs.
Skorski, T., et al., "BCR/ABL-mediated leukemogenesis requires the activity of the small GTP-binding protein Rac," PNAS USA, 1998, 95:11858-11862, 5 pgs.
Somervaille, T.C., et al., "Identification and characterization of leukemia stem cells in murine MLL-AF9 acute myeloid leukemia," Cancer Cell, 2006, 10:257-268, 12 pgs.
Sonata, S.I., Minowada, J., Tsubota, T. & Sandberg, A.A. Cytogenetic study of a new Ph1-positive cell line (NALM-1). *J Natl Cancer Inst* 59, 833-7 (1977).
Spencer-Smith, R., et al., "Direct inhibition of RAS: Quest for the Holy Grail?" Semin Cancer Biol, 2019, 54:138-148, 25 pgs.
Spiegel, J., et al., "Small-Molecule Modulation of Ras Signaling," Nature Chemical Biology, 2014, 10:613-622, 10 pgs.
Spoerner, M., et al., "Dynamic properties of the Ras switch I region and its importance for binding to effectors," PNAS USA, 2001, 98(9):4944-4949, 6 pgs.
Spoerner, M., et al., "Conformational States of Human Rat Sarcoma (Ras) Protein Complexed with Its Natural Ligand GTP and Their Role for Effector Interaction and GTP Hydrolysis," J Biol Chem, 2010, 285(51):39768-39778, 11 pgs.
Spoerner, M., et al., "Slow conformational dynamics of the guanine nucleotide-binding protein Ras complexed with the GTP analogue GTPγS," The FEBS Journal, 2007, 274:1419-1433, 15 pgs.
Steck, A.K. et al. Effects of non-HLA gene polymorphisms on development of islet autoimmunity and type 1 diabetes in a population with high-risk HLA-DR,DQ genotypes. Diabetes 61, 753-8 (2012.
Steffen, A. et al. Rac function is crucial for cell migration but is not required for spreading and focal adhesion formation. *J Cell Sci* 126, 4572-88 (2013).
Stephen, A.G., et al., "Dragging Ras Back in the Ring," Cancer Cell, 2014, 25:272-281, 10 pgs.
Studier, F.W., "Protein production by auto-induction in high density shaking cultures," Protein Expr Purif, 2005, 41:207-234, 28 pgs.
Sydykov, B., et al., "Storage stability of liposomes stored at elevated subzero temperatures in DMSO/sucrose mixtures," Plos One, 2018, 13(7):e0199867, 16 pgs.
Sun, Q., et al., "Discovery of Small Molecules that Bind to K-Ras and Inhibit Sos-Mediated Activation," Angew Chem Int Ed, 2012, 51:6140-6143, 4 pgs.
Sundaresan, M. et al. Regulation of reactive-oxygen-species generation in fibroblasts by Rac1. *Biochem J* 318 ( Pt 2), 379-82 (1996).
Sung, Y.J., et al., "Mutagenesis of the H-ras p21 at Glycine-60 Residue Disrupts GTP-Induced Conformational Change," Biochemistry, 1995, 34:3470-3477, 8 pgs.
Sung, Y.J., et al., "The Dominant Negative Effects of H-Ras Harboring a Gly to Ala Mutation at Position 60," J Biol Chem, 1996, 271(48):30537-30543, 7 pgs.
Swaminathan, G. & Tsygankov, A. Y. The Cbl family proteins: ring leaders in regulation of cell signaling. Journal of cellular physiology 209, 21-43 (2006).
Tajan, M., et al., "The RASopathy Family: Consequences of Germline Activation of the RAS/MAPK Pathway," Endocr Rev, 2018, 39:676-700, 25 pgs.
Tan, A.R. & Swain, S.M., "Therapeutic Strategies for Triple-Negative Breast Cancer." Cancer J 14, 343-51 (2008).
Tartaglia, M., et al., "Gain-of-function SOS1 mutations cause a distinctive form of Noonan syndrome," Nat Genet, 2007, 39(1):75-79, 6 pgs.
Tartaglia, M., et al., "Noonan syndrome and clinically related disorders," Best Pract Res Clin Endocrinol Metab, 2011, 25(1):161-179, 25 pgs.
Tasian, S.K., Loh, M.L. & Hunger, S.P. Philadelphia chromosome-like acute lymphoblastic leukemia. *Blood* 130, 2064-2072 (2017).
Thomas, E.K., Cancelas, J.A., Zheng, Y. & Williams, D.A. Rac GTPases as key regulators of p210-BCR-ABL-dependent leukemogenesis. *Leukemia* 22, 898-904 (2008).
Thomas, E.K. et al. Rac guanosine triphosphatases represent integrating molecular therapeutic targets for BCR-ABL-induced myeloproliferative disease. *Cancer Cell* 12, 467-78 (2007).
Tidyman, W.E., et al., "The RASopathies: Developmental syndromes of Ras/MAPK pathway dysregulation," Curr Opin Genet Dev, 2009, 19(3):230-236, 11 pgs.
Tomayko, M.M., et al., "Determination of subcutaneous tumor size in athymic (nude) mice," Cancer Chemotherapy and Pharmacology, 1989, 24:148-154, 7 pgs.
Toyama, T. et al., "Frequently Increased Epidermal Growth Factor Receptor (EGFR) Copy Numbers and Decreased BRCA1 mRNA Expression in Japanese Triple-Negative Breast Cancers." BMC Cancer 8, 309 (2008).
Trovo-Marqui, A.B., et al., "Neurofibromin: a general outlook," Clin Genet, 2006, 70:1-13, 13 pgs.
Ueno, N.T., & Zhang, D. "Targeting EGFR in Triple Negative Breast Cancer" J. Cancer 2, 324-8 (2011).
Van Eerdenbrugh, B., et al., "Characterization of physico-chemical properties and pharmaceutical performance of sucrose co-freeze-dried solid nanoparticulate powders of the anti-HIV agent loviride prepared by media milling," Int J Pharma, 2007, 338(Issues 1-3):198-206, 9 pgs.
Vetter, I.R., et al., "The Guanine Nucleotide-Binding Switch in Three Dimensions," Science, 2001, 294:1299-1304, 6 pgs.

(56) References Cited

OTHER PUBLICATIONS

Vicent, S., et al., "ERK1/2 is activated in non-small-cell lung cancer and associated with advanced tumours," Br J Cancer, 2004, 90:1047-1052, 6 pgs.
Vigil, D., Cherfils, J., Rossman, K.L. & Der, C.J. Ras superfamily GEFs and GAPs: validated and tractable targets for cancer therapy? *Nat Rev Cancer* 10, 842-57 (2010).
Wang, X. et al. Obesity related methylation changes in DNA of peripheral blood leukocytes. BMC medicine 8, 87 (2010).
Wang, Z., et al., "Racl is crucial for Ras-dependent skin tumor formation by controlling Pakl-Mek-Erk hyperactivation and hyperproliferation in vivo," Oncogene, 2010, 29(23):3362-3373, 12 pgs.
Warmuth, M., Kim. S., Gu, X.J., Xia, G. & Adrian, F. Ba/F3 Cells and Their Use in Kinase Drug Discovery, Curr Opin Oncol 19, 55-60 (2007).
Wattenhofer, M. et al. Isolation and characterization of the UBASH3A gene on 21q22.3 encoding a potential nuclear protein with a novel combination of domains. Hum Genet 108, 140-7 (2001).
Wei, J. et al. Microenvironment determines lineage fate in a human model of MLL-AF9 leukemia. *Cancer Cell* 13, 483-95 (2008).
Welsch, M.E., et al., "Multivalent small-molecule pan-RAS inhibitors," Cell, 2017, 168(5):878-889, 53 pgs.
Williams, D.A. et al. Dominant negative mutation of the hematopoietic-specific Rho GTPase, Rac2, is associated with a human phagocyte immunodeficiency. *Blood* 96, 1646-54 (2000).
Wittinghofer, A., et al., "How Ras-related proteins talk to their effectors," Trends in Biochemical Sciences, 1996, 21:488-491, 4 pgs.
Woods, K.W., et al., "Synthesis and SAR of indazole-pyridine based protein kinase B/Akt inhibitors," Bioorganic & Medicinal Chemistry, 2006, 14:6832-6846, 15 pgs.
Xing, L., et al., "Scaffold mining of kinase hinge binders in crystal structure database," J Comput Aided Mol Des, 2014, 28:13-23, 11 pgs.
Yamaguchi, H., et al., "Regulation of the actin cytoskeleton in cancer cell migration and invasion," Biochim Biophys Acta, 2007, 1773(5):642-652, 20 pgs.
Yamaguchi, H., et al., "Cell migration in tumors," Current Opinion in Cell Biology, 2005, 17:559-564, 6 pgs.
Yoshizawa, A., et al., "Overexpression of Phospho-eIF4E is Associated with Survival through AKT Pathway in Non-Small Cell Lung Cancer," Clin Cancer Res, 2010, 16(1):240-248, 20 pgs.
Yu, J.S., Chen, W.J., Ni, M.H., Chan, W.H. & Yang, S.D. Identification of the regulatory autophosphorylation site of autophosphorylation-dependent protein kinase (auto-kinase). Evidence that auto-kinase belongs to a member of the p21-activated kinase family. *Biochem J* 334 ( Pt 1), 121-31 (1998).
Zandvakili, I., Lin, Y., Morris, J.C. & Zheng, Y. Rho GTPases: Anti- or pro-neoplastic targets? *Oncogene* 36, 3213-3222 (2017).
Zenke, F.T., King, C.C., Bohl, B.P. & Bokoch, G.M. Identification of a central phosphorylation site in p21-activated kinase regulating autoinhibition and kinase activity. *J Biol Chem* 274, 32565-73 (1999).
Zhu, Y. et al., "Neurofibromin, a Tumor Suppressor in the Nervous System," Exp Cell Res, 2001, 264:19-28, 10 pgs.
Zha, J., Harada, H., Yang, E., Jockel, J. & Korsmeyer, S.J. Serine phosphorylation of death agonist BAD in response to survival factor results in binding to 14-3-3 not BCL-X(L). *Cell* 87, 619-28 (1996).
Zhang, S.C. et al. Liposome reconstitution and modulation of recombinant prenylated human Rac1 by GEFs, GDI1 and Pak1. *PLoS One* 9, e102425 (2014).
Zhuang, H., et al., "Progress of clinical research on targeted therapy combined with thoracic radiotherapy for non-small-cell lung cancer," Drug Des Devel Ther, 2014, 8:667-675, 9 pgs.
Veldhuis, J.D., Anderson, S.M., Iranmanesh, A. & Bowers, C.Y. "Testosterone Blunts Feedback Inhibition of Growth Hormone Secretion by Experimentally Elevated Insulin-like Growth Factor-I Concentrations." J Clin Endocrinol Metab 90, 1613-7 (2005).
Zhernakova, A. et al. Meta-analysis of genome-wide association studies in celiac disease and rheumatoid arthritis identifies fourteen non-HLA shared loci. PLoS genetics 7, e1002004 (2011).

* cited by examiner

MDA-MB-231 cells

MDA-MB-231 xenografts

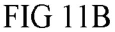
FIG 11B
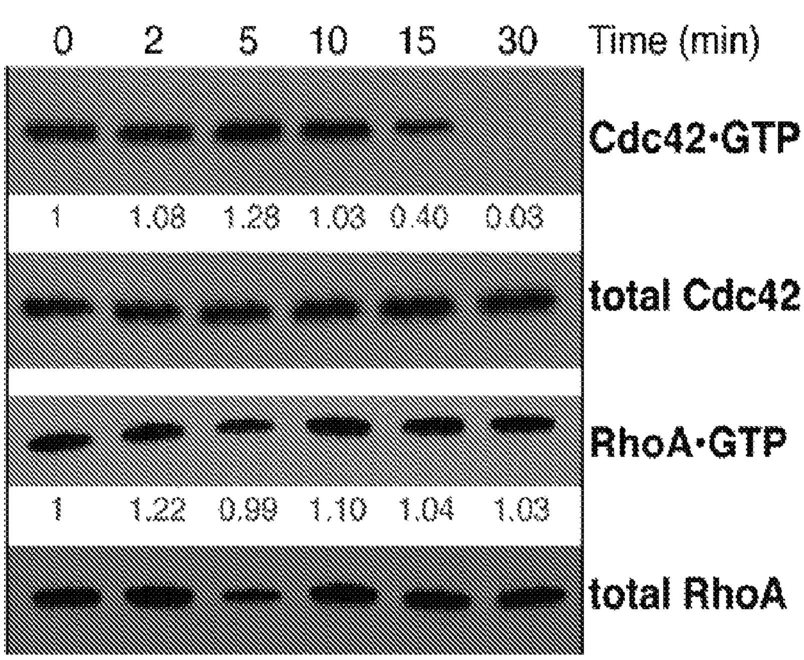
FIG 11C
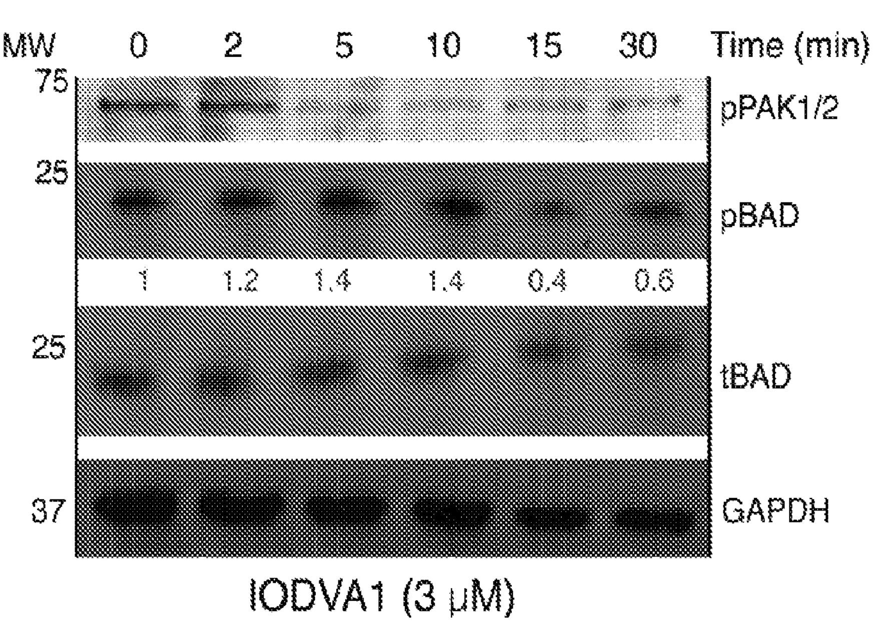

COMBINATION THERAPY FOR VAV3 CANCER

CROSS-REFERENCE TO RELATED APPLICATIONS

This application is national stage entry of International Application No. PCT/US22/39790 filed Aug. 9, 2022, which claims priority to and benefit of U.S. Provisional Pat. App. No. 63/231,035, entitled "COMBINATION THERAPY FOR VAV3 CANCER," filed Aug. 9, 2021, the disclosures of each are incorporated by reference herein, in their entirety and for all purposes.

STATEMENT REGARDING FEDERALLY-SPONSORED RESEARCH

This invention was made with government support under CA 237016 awarded by the National Institutes of Health. The government has certain rights in the invention.

BACKGROUND

Cancer is a serious public health problem in the United States and other developed countries. Currently, one in four deaths in the United States is due to cancer. However, many cancers are not responsive to existing treatments, or are only minimally responsive, such that existing therapies are not effective. In addition, appearance of resistance mechanisms to current therapies and relapse continue to be a major impediment in the clinic. The leading therapies for cancer are currently surgery, radiation, targeted and immunotherapies, and chemotherapy. Chemotherapeutic approaches such as antitumor antibiotics, alkylating agents, nitrosourea compounds, *vinca* alkaloids, steroid hormones, and anti-metabolites form the bulk of therapies available to oncologists. They have undesirable side effects because they don't distinguish between healthy and cancerous tissue. Despite advances in the field of cancer treatment, cancer remains a major health problem.

Thus, there is an urgent need in the art for compositions and methods for treatment of cancer. The present disclosure seeks to address this need in the art.

BRIEF DESCRIPTION OF THE DRAWINGS

Those of skill in the art will understand that the drawings, described below, are for illustrative purposes only. The drawings are not intended to limit the scope of the present teachings in any way.

(FIG. 5A) Schematic of domain architecture of full-length, ΔCH and GEF-mutant VAV3; calponin-homology (CH), acidic region (Ac), Dbl-homology (DH), pleckstrin-homology (PH), zinc finger (ZF), SRC-homology 2 and 3 (SH2/SH3). Black circle and star indicate Y173 and N369, respectively. (FIG. 5B) Bar graphs of representative cell cycle analysis experiment of wild-type ($Vav3^{+/+}$) and VAV3-deficient ($Vav3^{-/-}$) p190-BCR-ABL1 leukemic bone marrow cells expressing empty vector, full-length VAV3, ΔCH or N369A mutants and treated with vehicle control (black) or IODVA1 at 5 or 10 μM for 18 h. (FIG. 5C) Quantification of the average number of colonies made by wild-type and $Vav3^{-/-}$ p190-BCR-ABL1 leukemic bone marrow cells expressing empty vector, or the VAV3 constructs used in (5B) and treated with vehicle control (black) or IODVA1 at 1, 5 and 10 μM. n.s.—not significant, *p≤0.05; p≤0.01; **p≤0.0001 based on Two-way ANOVA with Tukey's multiple comparison test.

FIGS. 11A-11G: depict data showing IODVA1 decreases RAC signaling but does not interfere with the action of the RAC negative regulators GAP or RhoGDI. (11A) Levels of active RAC were assessed using PAK-GBD pull-down assay as was done for (3A), but cells were incubated for a fixed amount of time (1 h) at the indicated IODVA1 concentrations. Densitometric quantification of active RAC (RAC·GTP) levels were done using ImageJ (11B) p190-BCR-ABL1 Ba/F3 cells were treated with IODVA1 (3 M) and levels of active Cdc42 (Cdc42·GTP) and RhoA (Rho·GTP) were assessed by pull-down at the indicated times using GST-PAK-GBD and GST-Rhotekin respectively, followed by immunoblotting. Levels of active GTPase were assessed using ImageJ. (11C) p190-BCR-ABL1 Ba/F3 cells were treated with IODVA1 (3 μM) and lysed at the indicated times. Cell lysates were separated on SDS-PAGE and immunoblotted for pPAK1/2 (T423/T402), pBAD (S136), and BAD. GAPDH was used as loading control. (11A)-(11C) representative blots of two independent experiments. (11D) Morphology of $GFP^+$ leukemic colonies (left panel). Western blot analysis of RAC1 and RAC2 protein expression in $Rac1^{\Delta/\Delta}$+$Rac2^{-/-}$ cells post poly-I: C injections (right panel). (11E) Intrinsic (blue line) and p50GAP-stimulated GTP-hydrolysis reaction in the presence (red line) or absence (black line) of IODVA1. (11F) Sedimentation assay of liposomal RAC1-GDP in the presence of RhoGDI1 (4 μM) and IODVA1 (2 μM). RAC1 was visualized by immunoblotting from pellet (p) and soluble(s) fractions. (11G) Stopped-flow measurement of GDI (10 μM) interaction with fluorescently labelled RAC1 in the absence (black line) or presence (red line) of IODVA1.

DETAILED DESCRIPTION

Definitions

Figure 1A:
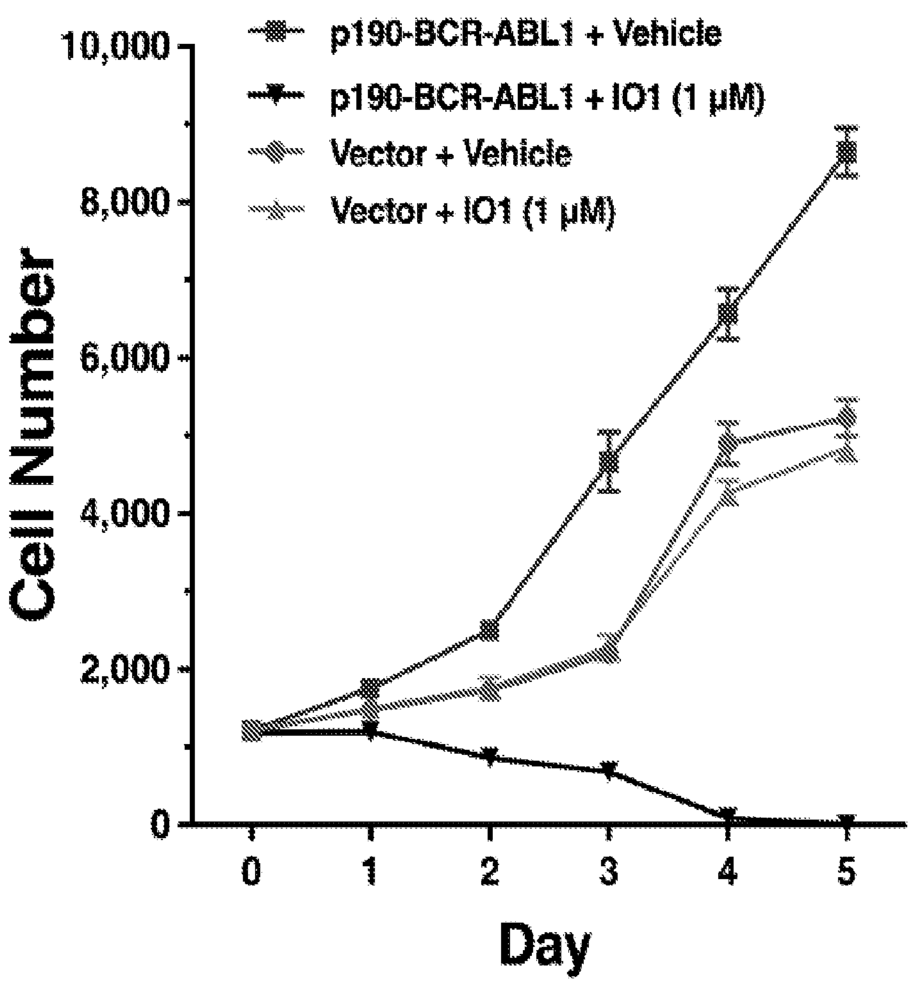
FIGS. 1A-1D depict data showing that IODVA1 inhibits the proliferation and survival of BCR-ABL1-driven cells in vitro and in vivo and eradicates leukemia-propagating cells in secondary transplants. (1A) Cell proliferation of human peripheral $CD34^+$ blood cells transduced with p190-BCR-ABL1 (gray line, squares, and black line, downward triangles) or empty vector (circles and upward triangles) virus and treated with either vehicle or IODVA1 (IO1, 1 μM). Live cells were counted by flow cytometry ($GFP^+$/7-$AAD^-$). Mean±SD of a representative experiment done in triplicates (1B) Cells were transduced and cultured as in (1A) but incubated with either vehicle or IODVA1 (IO1, 1 or 3 μM) and viability (%) was determined by trypan blue exclusion. Mean±SD of a representative experiment done in triplicates. (1C) Kaplan-Meier survival plot of p190-BCR-ABL1 leukemic mice post-treatment with vehicle control, IODVA1 (IO1), imatinib (IM), or the combination at the indicated concentrations in the pump. LDBM cells were transduced with p190-BCR-ABL1/EGFP retrovirus and transplanted into recipient mice. After initial assessment of leukemic burden, drugs were delivered for 28 days in subcutaneously implanted osmotic pumps at day 23 post leukemia transplantation. N=5 mice per group, except for vehicle N=6. (1D) Kaplan-Meier survival plot of secondary mice transplants with the $10^6$-cell dilution. Bone marrow cells from mice treated with vehicle, imatinib (IM), IODVA1 (IO1) or the combination at the indicated concentrations were transplanted into secondary recipients. N=5 mice per group. Arrows indicate overlapping corresponding curves.

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some aspects, the terms refer to humans. In further aspects, the terms may refer to children.

The terms "pharmaceutically acceptable salts" or "a pharmaceutically acceptable salt thereof" refer to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts; salts of free acids and bases; inorganic salts, e.g., sulfate, hydrochloride, and hydrobromide; and other salts which are currently in widespread pharmaceutical use and are listed in sources well known to those of skill in the art, such as The Merck Index. Any suitable constituent can be selected to make a salt of an active drug discussed herein, provided that it is non-toxic and does not substantially interfere with the desired activity. In addition to salts, pharmaceutically acceptable precursors and derivatives of the compounds can be employed. Pharmaceutically acceptable amides, lower alkyl esters, and protected derivatives of the disclosed actives can also be suitable for use in the compositions and methods disclosed herein. A salt of a compound of this disclosure may be formed between an acid and a basic group of the compound, such as an amino functional group, or a base and an acidic group of the compound, such as a carboxyl functional group. According to another aspect, the compound is a pharmaceutically acceptable acid addition salt. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one aspect, pharmaceutically acceptable acid addition salts include those formed with mineral acids such as hydrochloric acid and hydrobromic acid, and especially those formed with organic acids such as maleic acid.

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The term "carrier" applied to pharmaceutical compositions of the disclosure refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable, or synthetic origin, such as peanut oil, soybean oil, mineral oil, sesame oil and the like. Suitable pharmaceutical carriers are described in "Remington's Pharmaceutical Sciences" (any edition).

The term "compound," as used herein, is also intended to include any salts, solvates, or hydrates thereof.

The term "alkyl" includes straight, branched chain, or cyclic alkyl groups, such as, but not limited to, methyl, ethyl, propyl, butyl, trifluoromethyl, and tetradecyl.

The term "alkoxy" includes straight, branched chain, or cyclic alkoxy groups, such as, but not limited to, methoxy, ethoxy, propoxy, butoxy, 2-methoxyethoxy, sec-butoxy, hexyloxy, and 2-ethylhexyloxy, tetradecyloxy groups.

The term "aryl" encompasses monocyclic and polycyclic aryl groups which contain only carbons on the first ring. The term "monocyclic aryl" refers to phenyl (where the ring only contains carbons), and the term "polycyclic aryl" refers to napthyl and anthracenyl, to phenyl rings having at least a second ring fused thereto, and to napthyl rings having a third ring fused thereto. In the case of a polycyclic aryl consisting of a phenyl ring having a second or third ring fused thereto, or a napthyl ring having a third ring fused thereto, the additional rings may be aromatic or non-aromatic carbocyclic or heterocyclic rings, provided that in such cases the point of attachment will be to the carbocyclic aromatic ring. For example, a subset of this aryl group is a polycyclic aryl group wherein the second ring is a "heteroaryl" which contains carbon atoms and at least one heteroatom selected from the group consisting of O, N, and S (provided that O and S cannot be adjacent to each other in the same ring). Alternatively, a ring carbon atom of the second and/or third further rings may be replaced with a carbonyl [—C(═O) group] (e.g., when such rings are non-aromatic). "Substituted aryl" refers to an aryl group substituted by one or more substituents, preferably 1 to 4 substituents (more preferably 1 or 2), at any point of attachment of any ring, selected from alkyl, substituted alkyl, and the substituents recited above for substituted alkyl groups.

Accordingly, examples of aryl groups that may be of interest in forming compounds disclosed herein may include:

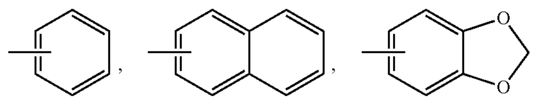

-continued

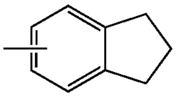, 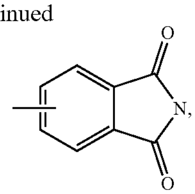

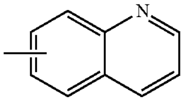, 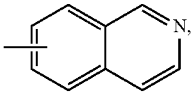

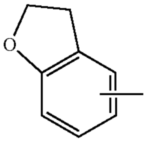, 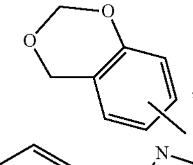, 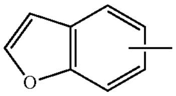,

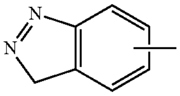, 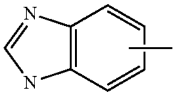,

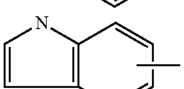, 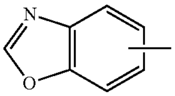,

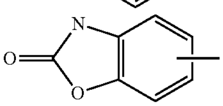, 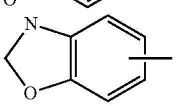,

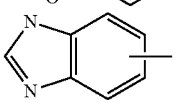, 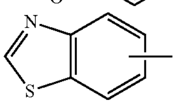,

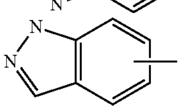, 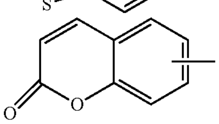,

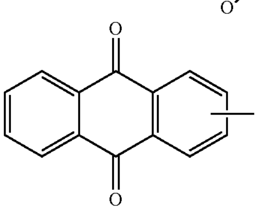, 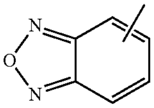, and, additionally, similar structures.

The terms “heterocycle,” “heterocyclic,” and “heterocyclo” refer to fully saturated, partially unsaturated, or fully unsaturated, including aromatic (i.e., “heteroaryl”) cyclic groups (for example, 3 to 7 membered monocyclic, 7 to 11 membered bicyclic, or 10 to 16 membered tricyclic ring systems) which have at least one heteroatom in at least one carbon atom-containing ring. Thus, the term “heteroaryl” is a subset of heterocyclo groups. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized, provided sulfur and oxygen are not adjacent to each other in the ring. (The term “heteroarylium” refers to a heteroaryl group bearing a quaternary nitrogen atom and thus a positive charge.) Additionally, one or more (in one aspect, one) carbon ring atoms of the heterocyclo ring may, as valence allows, be replaced with carbonyl group, i.e., —C(═O)—. The heterocyclic group may be attached to the remainder of the molecule at any heteroatom or carbon atom of the ring or ring system.

Exemplary monocyclic heterocyclic groups include those selected from the group consisting of ethylene oxide, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include those selected from the group consisting of indolyl, isoindolyl, benzothiazolyl, benzodioxolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydrobenzodioxinyl, dihydrodioxidobenzothiophenyl, dihydroisoindolyl, dihydroindolyl, dihydroquinolinyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, dibenzofuranyl, acridinyl, phenanthridinyl, xanthenyl and the like.

The term “heterocyclene” refers to bivalent heterocycle groups as defined above.

“Substituted heterocycle,” “substituted heterocyclic,” and “substituted heterocyclo” (such as “substituted heteroaryl”) refer to heterocycle, heterocyclic or heterocyclo groups substituted with one or more substituents, preferably 1 to 4 substituents, at any available point of attachment, wherein the substituents arc selected from those recited above for substituted cycloalkyl groups.

The term “group” is intended to encompass not only the substituent’s unsubstituted form, but also its form further substituted with any substituent group or groups as herein mentioned, so long as the substituent does not destroy properties necessary for utility. Suitably, a substituent group may be halogen or may be bonded to the remainder of the molecule by an atom of carbon, nitrogen, oxygen, or sulfur.

Disclosed herein are methods that may employ administration of an IODVA1 compound, alone or in combination with a tyrosine kinase inhibitor (TKI).

IODVA1 Compounds

In one aspect, the methods may employ the use of a composition that may comprise a compound having the following structure:

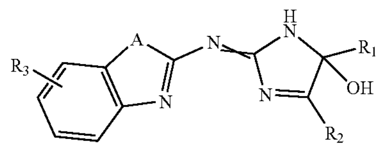

(referred to herein as “Compound 1,” or “an IODVA1 compound”) and a pharmaceutically acceptable carrier;

wherein A=NH, $NR_8$, S, O, C═C, N═C, C═N wherein $R_1$, $R_2$ are independently substituted or unsubstituted aryl or heteroaryl rings wherein $R_3$=singly or multiply substituted as H, D, Halo, CN, C1-C4 Alkyl, C1-C4 Alkoxy, C1-C4 Alkylsulfonyl, C1-C4 Alkyl amino, or C1-C4 mercapto wherein $R_8$=H, M;

and all tautomers thereof.

IODVA1 compounds and the manufacture of IODVA1 compounds are described in, for example WO2020227202A1, Nassar et al., entitled "Compositions and methods for treating cancer," published 12 Nov. 2020, the contents of which are incorporated herein it their entirety.

In one aspect, the compound may have the structure

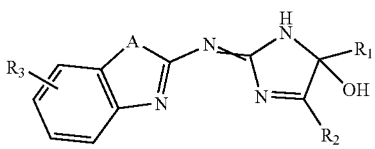

wherein A=NH, S wherein $R_1$, $R_2$ are independently substituted or unsubstituted phenyl, pyridyl, furanyl, pyrimidinyl, triazinyl, or diazinyl rings wherein $R_3$=singly or multiply substituted as H, D, Halo, CN, OH, OMe, OEt, SMe, SEt, $SO_2Me$, NHMe, NMe2, Me, Et, or Pr;

and all tautomers thereof.

In one aspect, the compound may have the structure

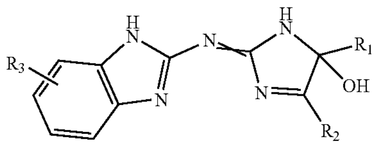

and wherein $R_1$, $R_2$ are independently substituted or unsubstituted phenyl, pyridyl, furanyl, pyrimidinyl rings wherein $R_3$=singly or multiply substituted as H, D, Halo, CN, OH, OMe, OEt, SMe, SEt, $SO_2Me$, NHMe, NMe2, Me, Et, or Pr, and all tautomers thereof.

In one aspect, the compound may have the structure

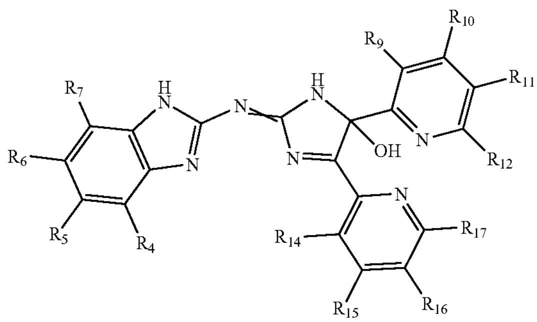

wherein $R_4$-$R_{17}$ are independently selected from H, D, Halo, CN, OH, OMe, OEt, SMe, SEt, $SO_2Me$, NHMe, NMe2, Me, Et, or Pr, and all tautomers thereof.

In one aspect, the compound may have the structure

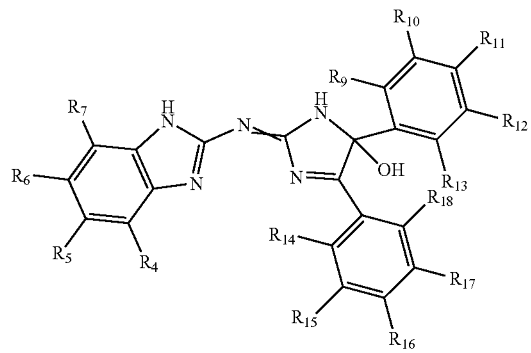

wherein $R_4$-$R_{17}$ are independently selected from H, D, Halo, CN, OH, OMe, OEt, SMe, SEt, $SO_2Me$, NHMe, NMe2, Me, Et, or Pr, and all tautomers thereof.

In one aspect, the compound may have the structure

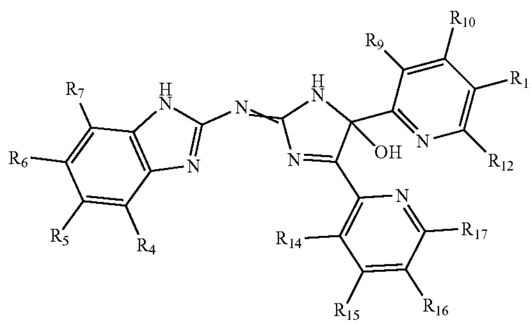

wherein $R_4$-$R_7$ are independently selected from H, D, F, Cl, CN, OH, OMe, SMe, Me, or Et;

wherein $R_9$-$R_{17}$ are independently selected from H, D, F, Cl, CN, OH, OMe, $SO_2Me$, NHMe, NMe2, Me, or Et;

and all tautomers thereof.

In one aspect, the compound may have the structure

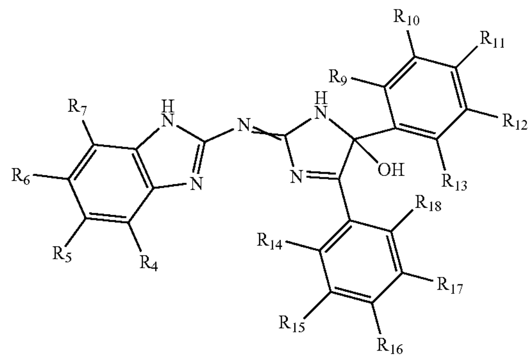

wherein $R_4$-$R_7$ are independently selected from H, D, F, Cl, CN, OH, OMe, SMe, Me, or Et;

wherein $R_9$-$R_{17}$ are independently selected from H, D, F, Cl, CN, OH, OMe, $SO_2Me$, NHMe, NMe2, Me, or Et, and all tautomers thereof.

In one aspect, the compound may have the structure

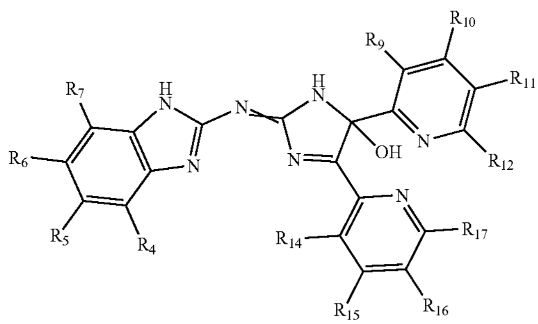

wherein $R_4$-$R_7$ are independently selected from H, D, F, OH, OMe, Me;

wherein $R_9$-$R_{17}$ are independently selected from H, D, F, Cl, CN, OH, OMe, $SO_2Me$, NHMe, NMe2, Me, or Et, and all tautomers thereof.

In one aspect, the compound may have the structure

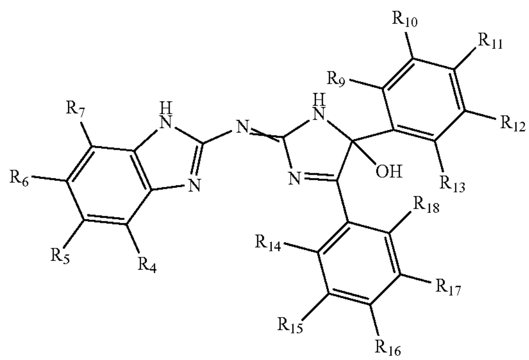

wherein $R_5$, $R_6$ are independently selected from H, D, F, Cl, OH, OMe, or Me;

wherein $R_9$-$R_{17}$ are independently selected from H, D, F, Cl, OH, OMe, or Me;

wherein each ring bears≤2 non-H substituents;

and all tautomers thereof.

In one aspect, the compound may have the structure

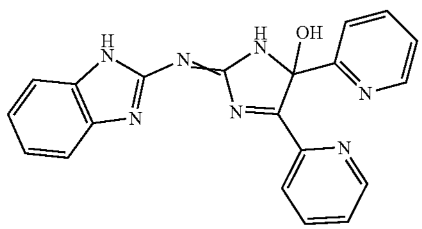 [SMILES: OC1(c2ccccn2)NC(=Nc2nc3ccccc3[nH]2)N=C1c1ccccn1]

and all tautomers thereof.

In one aspect, the compound may have the structure

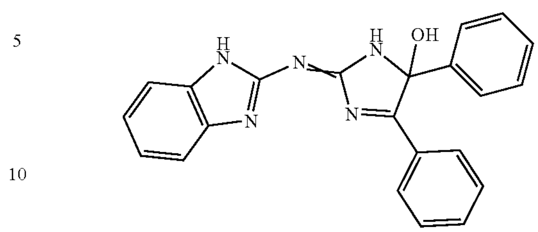

and all tautomers thereof.

In one aspect, a composition comprising a compound having the structure (1c)

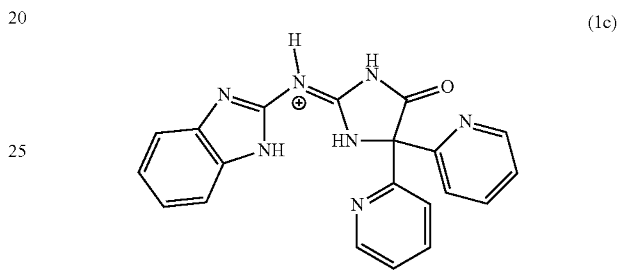

and a pharmaceutically acceptable carrier is disclosed.

In one aspect, the compound may have the structure

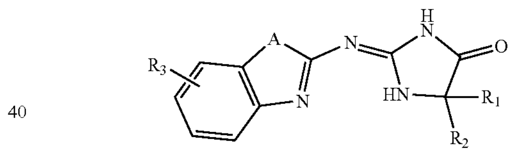

wherein A is selected from NH, $NR_8$, S, O, C═C, N═C, C═N; wherein $R_1$, $R_2$ are independently substituted or unsubstituted* aryl or heteroaryl rings; wherein R3 is singly or multiply substituted as H, D, Halo, CN, $C_1$-$C_4$ Alkyl, $C_1$-$C_4$ Alkoxy, $C_1$-$C_4$ Alkylsulfonyl, $C_1$-$C_4$ Alkyl amino, or C1-C4 mercapto; wherein $R_8$ is H or Me; and all tautomers thereof.

In one aspect, the compound may have the structure

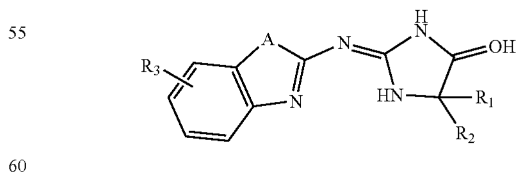

wherein A is NH or S; wherein $R_1$, $R_2$ are independently substituted or unsubstituted phenyl, pyridyl, furanyl, pyrimidinyl, triazinyl, or diazinyl rings; wherein $R_3$ is singly or multiply substituted as H, D, Halo, CN, OH, OMe, OEt, SMe, SEt, SO2Me, NHMe, NMe2, Me, Et, or Pr; and all tautomers thereof.

In one aspect, the compound may have the structure

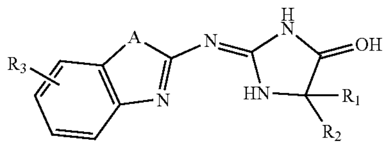

wherein $R_1$, $R_2$ are independently substituted or unsubstituted phenyl, pyridyl, furanyl, pyrimidinyl rings; wherein $R_3$ is singly or multiply substituted as H, D, Halo, CN, OH, OMe, OEt, SMe, SEt, $SO_2Me$, NHMe, NMe2, Me, Et, or Pr; and all tautomers thereof.

In one aspect, the compound may have the structure

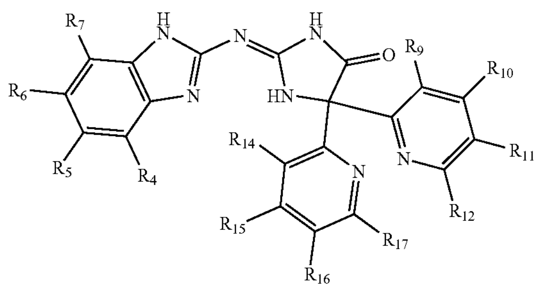

wherein $R_4$-$R_{17}$ are each independently selected from H, D, Halo, CN, OH, OMe, OEt, SMe, SEt, $SO_2Me$, NHMe, NMe2, Me, Et, or Pr; and all tautomers thereof.

In one aspect, the compound may have the structure

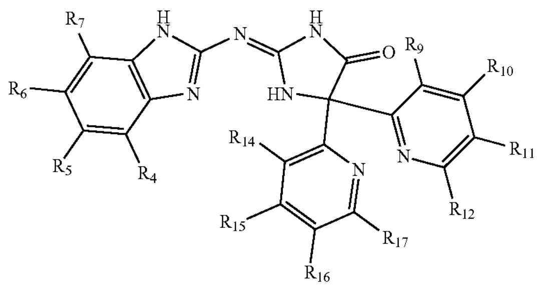

wherein $R_4$-$R_{17}$ are each independently selected from H, D, Halo, CN, OH, OMe, OEt, SMe, SEt, SO2Me, NHMe, NMe2, Me, Et, or P; and all tautomers thereof.

In one aspect, the compound may have the structure

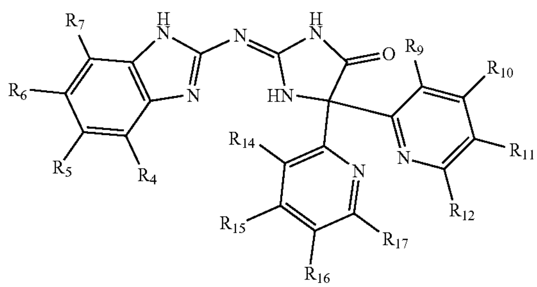

wherein $R_4$-$R_7$ are each independently selected from H, D, F, Cl, CN, OH, OMe, SMe, Me, or Et; wherein $R_9$-$R_{17}$ are each independently selected from H, D, F, Cl, CN, OH, OMe, $SO_2Me$, NHMe, NMe2, Me, or Et; and all tautomers thereof.

In one aspect, the compound may have the structure

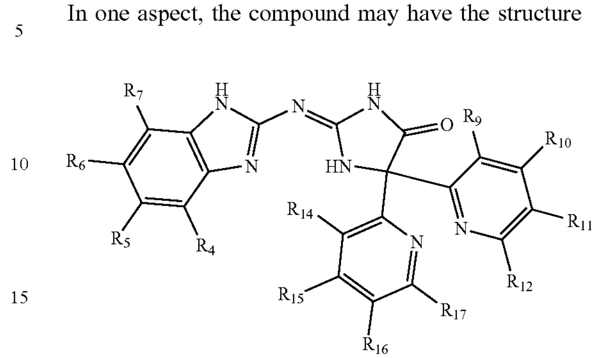

wherein $R_4$-$R_7$=H, D, F, Cl, CN, OH, OMe, SMe, Me, or Et; wherein $R_9$-$R_{17}$=H, D, F, Cl, CN, OH, OMe, $SO_2Me$, NHMe, NMe2, Me, or Et, and all tautomers thereof.

In one aspect, the compound may have the structure

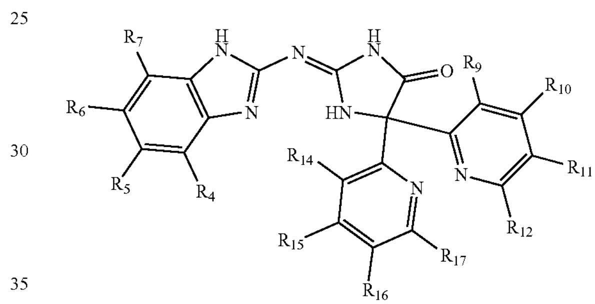

wherein $R_4$-$R_7$=Independently H, D, F, OH, OMe, Me; wherein $R_9$-$R_{17}$ may be independently selected from H, D, F, Cl, CN, OH, OMe, $SO_2Me$, NHMe, NMe2, Me, or Et, and all tautomers thereof.

In one aspect, the compound may have the structure

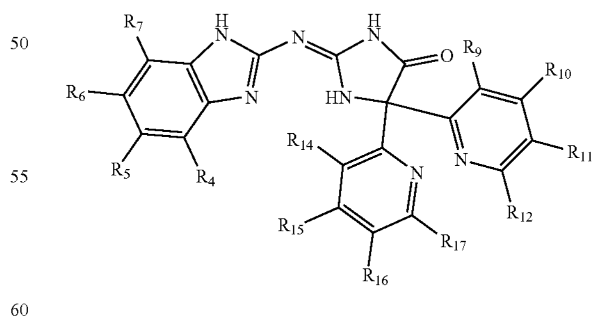

wherein $R_4$-$R_7$=Independently H, D, F, Cl, OH, OMe, or Me; wherein $R_9$-$R_{12}$ and $R_{14}$-$R_{17}$ may be independently selected from H, D, F, Cl, OH, OMe, or Me. Each ring bearing≤2 non-H substituents; and all tautomers thereof.

In one aspect, a composition comprising

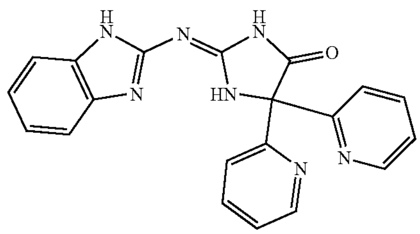 [SMILES: O=C1N/C(=N/c2nc3ccccc3[nH]2)NC1(c1ccccn1)c1ccccn1]

and all tautomers thereof, and a pharmaceutically acceptable carrier is disclosed.

In one aspect, a composition comprising

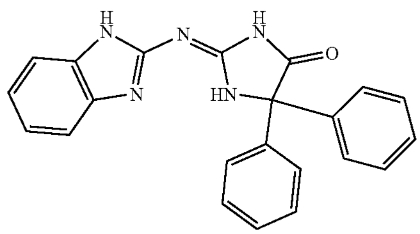 [SMILES: O=C1N/C(=N/c2nc3ccccc3[nH]2)NC1(c1ccccc1)c1ccccc1]

and all tautomers thereof, and a pharmaceutically acceptable carrier, is disclosed.

In one aspect, a composition comprising what is herein referred to as the NIRA2 class of compounds, is disclosed. The composition may comprise a compound having the structure:

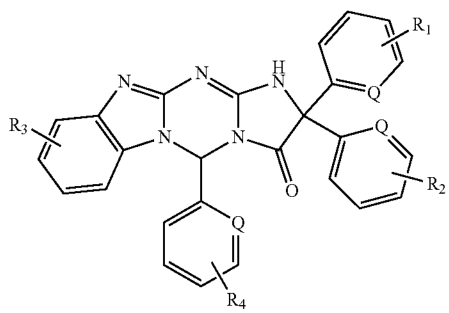

wherein $R_1$, $R_2$, and $R_4$ are independently selected from H, D, Halo, CN, OH, OMe, OEt, SMe, SEt, SO2Me, NHMe, NMe2, Me, Et, or Pr, and all tautomers thereof, wherein $R_3$ is singly or multiply substituted as H, D, Halo, CN, C1-C4 alkyl, C1-C4 alkoxy, C1-C4 alkylsufonyl; C1-C4 alkylamino, or C1-C4 mercapto; wherein A is selected from NH, NR8, S, O, C═C, N═C, C═N, wherein R8 is H or Me, wherein each Q is independently selected from N, C, and S; and a pharmaceutically acceptable carrier.

In one aspect, the compound may have the structure

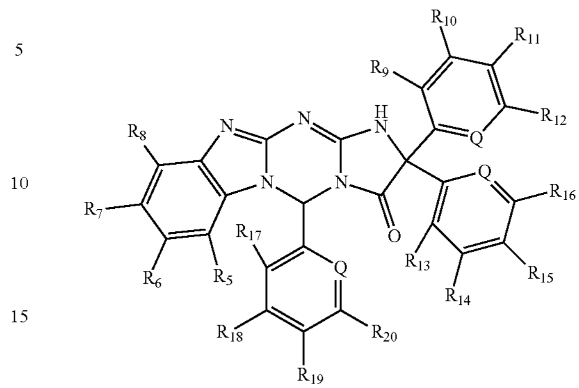

wherein $R_5$-$R_{20}$ are independently selected from H, D, Halo, CN, OH, OMe, OEt, SMe, SEt, $SO_2Me$, NMe2, Me, Et, or Pr, wherein each Q is independently selected from N, C, and S, and all tautomers thereof; and a pharmaceutically acceptable carrier.

In one aspect, the compound may have the structure

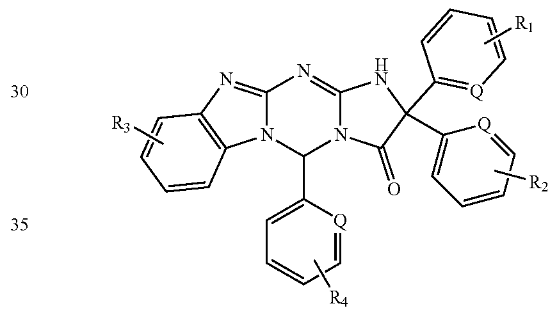

wherein $R_1$, $R_2$, and $R_4$ are independently selected from H, D, Halo, CN, OH, OMe, OEt, SMe, SEt, $SO_2Me$, NHMe, NMe2, Me, Et, or Pr, and all tautomers thereof; wherein $R_3$ is singly or multiply substituted as H, D, Halo, CN, C1-C4 alkyl; C1-C4 alkoxy; C1-C4 alkysulfonyl; C1-C4 akylamino; or C1-C4 mercapto; wherein A is selected from NH, $NR_8$, S, O, C═C, N═C, C═N, wherein $R_8$ is H or Me, wherein each Q is independently selected from N, C, and S; and a pharmaceutically acceptable carrier.

In one aspect, the compound may have the structure

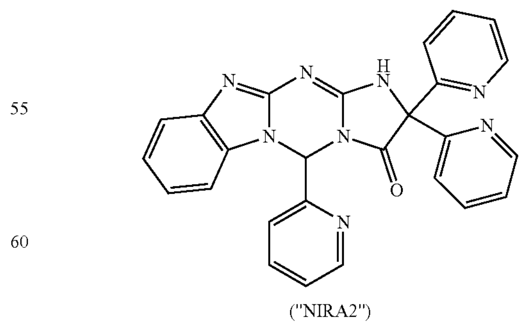

("NIRA2")

or a pharmaceutically acceptable salt thereof and a pharmaceutically acceptable carrier. In one aspect, the compound may have the structure

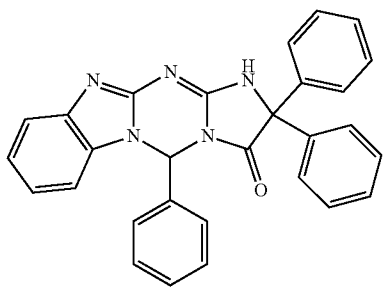 [SMILES: O=C1N2C(=Nc3nc4ccccc4n3C2c2ccccc2)NC1(c1ccccc1)c1ccccc1]

or a pharmaceutically acceptable salt thereof and a pharmaceutically acceptable carrier.

In one aspect, any of the aforementioned compositions may be free of, or substantially free of, one or both of the following compounds:

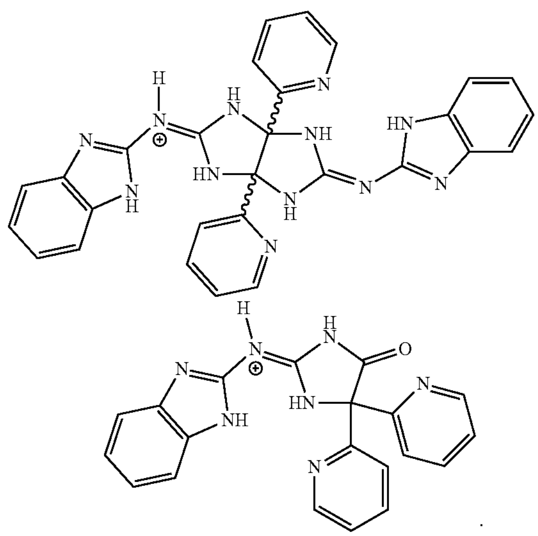

and

.

In one aspect, a composition comprising (NSC600805)

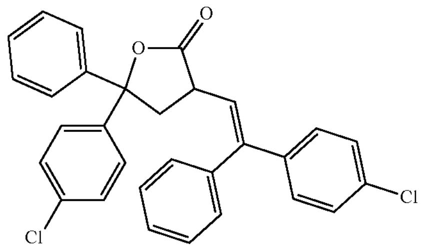

and a pharmaceutically acceptable carrier is disclosed.

Tyrosine Kinase Inhibitor (TKI)

The disclosed methods may employ the administration of a TKI. TKI's include, but are not limited to imatinib, gefitinib, erlotinib, sorafenib, sunitinib, and dasatinib. In one aspect, the TKI is Ponatinib. Ponatinib (also known as AP24534) is a potent, orally active TKI. The molecular formula of ponatinib is $C_{29}H_{28}C_{1}F_{3}N_{6}O$, and the chemical name is 3-(imidazo[1,2-b]pyridazin-3-ylethynyl)-4-methyl-N-19benzamide hydrochloride.[15] Ponatinib was structurally designed with a carbon-carbon triple bond to target the T315I point mutation within the kinase domain (KD) of BCR-ABL. See, e.g., Tan, Fiona H et al. "Ponatinib: a novel multi-tyrosine kinase inhibitor against human malignancies." OncoTargets and therapy vol. 12 635-645. 18 Jan. 2019, doi: 10.2147/OTT.S189391. Ponatinib (Iclusig®), taken by mouth, is approved for the treatment of adult patients with T315I-positive Ph+ ALL.

In one aspect, a method of treating an individual having a cancer, for example a leukemia, is disclosed. The method may comprise administering an IODVA1 compound to said individual, and administering ponatinib to said individual. The IODVA1 compound may be administered at one or more time points selected from prior to administration of a TKI, for example, ponatinib, concurrent with administration of a TKI, for example ponatinib, or following administration of a TKI, for example, ponatinib. The IODVA1 compound may be administered via one or more routes as may be determined by one of ordinary skill in the art, for example via a route selected from orally, intravenously, and combinations thereof. In one aspect, the cancer may be a leukemia that is a TKI-resistant leukemia. In one aspect, the leukemia may be a TKI-resistant Ph+ B-ALL In one aspect, the leukemia may be Chronic Myelogenous Leukemia (CML). In one aspect, the leukemia may be selected from Ph-Positive Acute Lymphoblastic Leukemia (ALL), Ph-like ALL, Chronic Myeloid Leukemia, Resistant Chronic Phase Chronic Myeloid Leukemia (CP-CML), MLL-rearranged B-ALL, a leukemia that is not a RAC-deficient leukemia, a VAV3 positive leukemia.

In one aspect, the individual being treated may be one having a p210-BCR-ABL1 (T315I) mutation. In further aspects, the individual may be a pediatric individual.

The disclosed methods may further provide a method for preventing leukemia relapse in an individual in need thereof comprising administering IODVA1 to the individual. In this aspect, the administration may be used to reduce leukemic stem cells in said individual, or to reduce leukemic progenitor B-cells from peripheral blood, or to reduce leukemic progenitor B-cells from bone marrow. The leukemia may be a TKI-resistant leukemia, a TKI-resistant Ph+ B-ALL, a Chronic Myelogenous Leukemia (CML), a Ph-Positive Acute Lymphoblastic Leukemia (ALL), a Ph-like ALL leukemia, a Chronic Myeloid Leukemial, a Resistant Chronic Phase Chronic Myeloid Leukemia (CP-CML), a MLL-rearranged B-ALL, a leukemia that is not a RAC-deficient leukemia, and/or a VAV3 positive leukemia. In certain aspects the individual may be a pediatric individual.

In further aspects, the methods may involve treating a cancer selected from one or more of a leukemia, for example ALL, AML, or MLL, chemotherapy-resistant leukemia, immunotherapy-resistant leukemia, relapsed leukemia, and other targeted-therapy resistant leukemias. In one aspect, the cancer may be selected from adenocarcinoma, breast cancer. In one aspect, the cancer may be one in which Vav3 is overexpressed, such as prostate cancer, ovarian cancer, endometrial cancer, thyroid cancer, lung cancer, particularly non-small cell lung cancer, colorectal cancer, pancreatic cancer, and cervical cancer. In one aspect, the cancer may be a Ras-driven cancer, including RASopathies, for example, NF1 or MPNST. In one aspect, the cancer is any cancer that overexpresses Vav3.

Method of Treatment Based on VAV3 Status.

In a further aspect, a method of treating a cancer based on the status of Vav3 expression is disclosed. In this aspect, the method may comprise the step of determining the level of Vav3 in a biopsy obtained from a cancer in an individual;

and administering an active agent as described herein to said individual where said level of Vav3 is elevated as compared to a control. In particular, the method may include the step of administering one or both of an IDOVAI compound as described herein and a TKI as described herein.

Pharmaceutical Compositions

In one aspect, active agents provided herein may be administered in an dosage form selected from intravenous or subcutaneous unit dosage form, oral, parenteral, intravenous, and subcutaneous. In some aspects, active agents provided herein may be formulated into liquid preparations for, e.g., oral administration. Suitable forms include suspensions, syrups, elixirs, and the like. In some aspects, unit dosage forms for oral administration include tablets and capsules. Unit dosage forms configured for administration once a day; however, in certain aspects it may be desirable to configure the unit dosage form for administration twice a day, or more.

In one aspect, pharmaceutical compositions may be isotonic with the blood or other body fluid of the recipient. The isotonicity of the compositions may be attained using sodium tartrate, propylene glycol or other inorganic or organic solutes. An example includes sodium chloride. Buffering agents may be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions may be maintained at the selected level using a pharmaceutically acceptable thickening agent. Thickening agents that may be used include, for example, methylcellulose, xanthan gum, carboxymethyl cellulose, hydroxypropyl cellulose, carbomer, and the like. In some aspects, the concentration of the thickener will depend upon the thickening agent selected. An amount may be used that will achieve the selected viscosity. Viscous compositions are normally prepared from solutions by the addition of such thickening agents.

A pharmaceutically acceptable preservative may be employed to increase the shelf life of the pharmaceutical compositions. Benzyl alcohol may be suitable, although a variety of preservatives including, for example, parabens, thimerosal, chlorobutanol, or benzalkonium chloride may also be employed. A suitable concentration of the preservative is typically from about 0.02% to about 2% based on the total weight of the composition, although larger or smaller amounts may be desirable depending upon the agent selected. Reducing agents, as described above, may be advantageously used to maintain good shelf life of the formulation.

In one aspect, active agents provided herein may be in admixture with a suitable carrier, diluent, or excipient such as sterile water, physiological saline, glucose, or the like, and may contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations may include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components may influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions may be provided as a tablet, aqueous or oil suspension, dispersible powder or granule, emulsion, hard or soft capsule, syrup or elixir. Compositions intended for oral use may be prepared according to any method known in the art for the manufacture of pharmaceutical compositions and may include one or more of the following agents: sweeteners, flavoring agents, coloring agents and preservatives. Aqueous suspensions may contain the active ingredient in admixture with excipients suitable for the manufacture of aqueous suspensions.

Formulations for oral use may also be provided as hard gelatin capsules, wherein the active ingredient(s) are mixed with an inert solid diluent, such as calcium carbonate, calcium phosphate, or kaolin, or as soft gelatin capsules. In soft capsules, the active agents may be dissolved or suspended in suitable liquids, such as water or an oil medium, such as peanut oil, olive oil, fatty oils, liquid paraffin, or liquid polyethylene glycols. Stabilizers and microspheres formulated for oral administration may also be used. Capsules may include push-fit capsules made of gelatin, as well as soft, sealed capsules made of gelatin and a plasticizer, such as glycerol or sorbitol. The push-fit capsules may contain the active ingredient in admixture with fillers such as lactose, binders such as starches, and/or lubricants, such as talc or magnesium stearate and, optionally, stabilizers.

Tablets may be uncoated or coated by known methods to delay disintegration and absorption in the gastrointestinal tract and thereby provide a sustained action over a longer period of time. For example, a time delay material such as glyceryl monostearate may be used. When administered in solid form, such as tablet form, the solid formmay comprise from about 0.001 wt. % or less to about 50 wt. % or more of active ingredient(s), for example, from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets may contain the active ingredients in admixture with non-toxic pharmaceutically acceptable excipients including inert materials. For example, a tablet may be prepared by compression or molding, optionally, with one or more additional ingredients. Compressed tablets may be prepared by compressing in a suitable machine the active ingredients in a free-flowing form such as powder or granules, optionally mixed with a binder, lubricant, inert diluent, surface active or dispersing agent. Molded tablets may be made by molding, in a suitable machine, a mixture of the powdered active agent moistened with an inert liquid diluent.

In some aspects, each tablet or capsule contains from about 1 mg or less to about 1,000 mg or more of a active agent provided herein, for example, from about 10, 20, 30, 40, 50, 60, 70, 80, 90, or 100 mg to about 150, 200, 250, 300, 350, 400, 450, 500, 550, 600, 650, 700, 750, 800, or 900 mg. In some aspects, tablets or capsules are provided in a range of dosages to permit divided dosages to be administered. A dosage appropriate to the patient and the number of doses to be administered daily may thus be conveniently selected. In certain aspects two or more of the therapeutic agents may be incorporated to be administered into a single tablet or other dosage form (e.g., in a combination therapy); however, in other aspects the therapeutic agents may be provided in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents may be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, or karaya, or alginic acid or salts thereof.

Binders may be used to form a hard tablet. Binders may include materials from natural products such as acacia, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, may be included in tablet formulations.

Surfactants may also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations may be employed wherein the active agent or analog(s) thereof is incorporated into an inert matrix that permits release by either diffusion or leaching mechanisms. Slowly degenerating matrices may also be incorporated into the formulation. Other delivery systems may include timed release, delayed release, or sustained release delivery systems.

Coatings may be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments may be added for identification or to characterize different combinations of active agent doses.

When administered orally in liquid form, a liquid carrier such as water, petroleum, oils of animal or plant origin such as peanut oil, mineral oil, soybean oil, or sesame oil, or synthetic oils may be added to the active ingredient(s). Physiological saline solution, dextrose, or other saccharide solution, or glycols such as ethylene glycol, propylene glycol, or polyethylene glycol are also suitable liquid carriers. The pharmaceutical compositions may also be in the form of oil-in-water emulsions. The oily phase may be a vegetable oil, such as olive or *arachis* oil, a mineral oil such as liquid paraffin, or a mixture thereof. Suitable emulsifying agents include naturally-occurring gums such as gum acacia and gum tragamayth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions may also contain sweetening and flavoring agents.

Pulmonary delivery of the active agent may also be employed. The active agent may be delivered to the lungs while inhaling and traverses across the lung epithelial lining to the blood stream. A wide range of mechanical devices designed for pulmonary delivery of therapeutic products may be employed, including but not limited to nebulizers, metered dose inhalers, and powder inhalers, all of which are familiar to those skilled in the art. These devices employ formulations suitable for the dispensing of active agent. Typically, each formulation is specific to the type of device employed and may involve the use of an appropriate propellant material, in addition to diluents, adjuvants, and/or carriers useful in therapy.

The active ingredients may be prepared for pulmonary delivery in particulate form with an average particle size of from 0.1 μm or less to 10 μm or more, for example, from about 0.2, 0.3, 0.4, 0.5, 0.6, 0.7, 0.8, or 0.9 μm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 μm. Pharmaceutically acceptable carriers for pulmonary delivery of active agent include carbohydrates such as trehalose, mannitol, xylitol, sucrose, lactose, and sorbitol. Other ingredients for use in formulations may include DPPC, DOPE, DSPC, and DOPC. Natural or synthetic surfactants may be used, including polyethylene glycol and dextrans, such as cyclodextran. Bile salts and other related enhancers, as well as cellulose and cellulose derivatives, and amino acids may also be used. Liposomes, microcapsules, microspheres, inclusion complexes, and other types of carriers may also be employed.

Pharmaceutical formulations suitable for use with a nebulizer, either jet or ultrasonic, typically comprise the active agent dissolved or suspended in water at a concentration of about 0.01 or less to 100 mg or more of active agent per mL of solution, for example, from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg per mL of solution. The formulation may also include a buffer and a simple sugar (e.g., for protein stabilization and regulation of osmotic pressure). The nebulizer formulation may also contain a surfactant, to reduce or prevent surface induced aggregation of the active agent caused by atomization of the solution in forming the aerosol.

Formulations for use with a metered-dose inhaler device generally comprise a finely divided powder containing the active ingredients suspended in a propellant with the aid of a surfactant. The propellant may include conventional propellants, such as chlorofluorocarbons, hydrochlorofluorocarbons, hydrofluorocarbons, and hydrocarbons. Example propellants include trichlorofluoromethane, dichlorodifluoromethane, dichlorotetrafluoroethanol, 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing active agent, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, for example, from about 5, 10, 15, 20, 25, 30, 35, 40, 45, or 50 wt. % to about 55, 60, 65, 70, 75, 80, 85, or 90 wt. % of the formulation.

In some aspects, an active agent provided herein may be administered by intravenous, parenteral, or other injection, in the form of a pyrogen-free, parenterally acceptable aqueous solution or oleaginous suspension. Suspensions may be formulated according to methods well known in the art using suitable dispersing or wetting agents and suspending agents. The preparation of acceptable aqueous solutions with suitable pH, isotonicity, stability, and the like, is within the skill in the art. In some aspects, a pharmaceutical composition for injection may include an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils may be employed conventionally as a solvent or suspending medium. For this purpose, any bland fixed oil may be employed including synthetic mono or diglycerides. In addition, fatty acids such as oleic acid may likewise be used in the formation of injectable preparations. The pharmaceutical compositions may also contain stabilizers, preservatives, buffers, antioxidants, or other additives known to those of skill in the art.

The duration of the injection may be adjusted depending upon various factors, and may comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

In some aspects, the active agents provided herein may be provided to an administering physician or other health care professional in the form of a kit. The kit is a package which houses a container which contains the active agent(s) in a suitable pharmaceutical composition, and instructions for administering the pharmaceutical composition to a subject. The kit may optionally also contain one or more additional therapeutic agents currently employed for treating a disease state as described herein. For example, a kit containing one or more compositions comprising active agents provided herein in combination with one or more additional active agents may be provided, or separate pharmaceutical compositions containing an active agent as provided herein and additional therapeutic agents may be provided. The kit may also contain separate doses of a active agent provided herein for serial or sequential administration. The kit may optionally contain one or more diagnostic tools and instructions for use. The kit may contain suitable delivery devices, e.g., syringes, and the like, along with instructions for administering the active agent(s) and any other therapeutic agent. The kit may optionally contain instructions for storage, reconstitution (if applicable), and administration of any or all therapeutic agents included. The kits may include a plurality of containers reflecting the number of administrations to be given to a subject.

Dosage

In one aspect, an agent disclosed herein may be present in an amount of from about 0.5% to about 95%, or from about 1% to about 90%, or from about 2% to about 85%, or from about 3% to about 80%, or from about 4%, about 75%, or from about 5% to about 70%, or from about 6%, about 65%, or from about 7% to about 60%, or from about 8% to about 55%, or from about 9% to about 50%, or from about 10% to about 40%, by weight of the composition.

In one aspect, the compounds may be administered at the rate of 100 μg to 1000 mg per day per kg of body weight. Orally, the compounds may be suitably administered at the rate of about 100, 150, 200, 250, 300, 350, 400, 450, or 500 μg to about 1, 5, 10, 25, 50, 75, 100, 200, 300, 400, 500, 600, 700, 800, 900, 1000 mg per day per kg of body weight. The required dose can be administered in one or more portions. For oral administration, suitable forms are, for example, tablets, gel, aerosols, pills, dragees, syrups, suspensions, emulsions, solutions, powders and granules; one method of administration includes using a suitable form containing from 1 mg to about 500 mg of active substance. In one aspect, administration may comprise using a suitable form containing from about 1, 2, 5, 10, 25, or 50 mg to about 100, 200, 300, 400, 500 mg of active substance.

A dosage regimen will vary depending upon known factors such as the pharmacodynamic and pharmacokinetic characteristics of the agents and their mode and route of administration; the species, age, sex, health, medical condition, and weight of the patient, the nature and extent of the symptoms, the kind of concurrent treatment, the frequency of treatment, the route of administration, the renal and hepatic function of the patient, and the desired effect. The effective amount of a drug required to prevent, counter, or arrest progression of a symptom or effect of a muscle contracture can be administered. In one aspect, active agents provided herein may be administered in a dosage form selected from intravenous or subcutaneous unit dosage form, oral, parenteral, intravenous, and subcutaneous. In some aspects, active agents provided herein may be formulated into liquid preparations for, e.g., oral administration. Suitable forms include suspensions, syrups, elixirs, and the like. In some aspects, unit dosage forms for oral administration include tablets and capsules. Unit dosage forms configured for administration once a day; however, in certain aspects it may be desirable to configure the unit dosage form for administration twice a day, or more.

In some aspects, active agents provided herein may additionally employ adjunct components conventionally found in pharmaceutical compositions in their art-established fashion and at their art-established levels. Thus, for example, the compositions may contain additional compatible pharmaceutically active materials for combination therapy or may contain materials useful in physically formulating various dosage forms, such as excipients, dyes, thickening agents, stabilizers, preservatives or antioxidants.

EXAMPLES

The following non-limiting examples are provided to further illustrate aspects of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

Despite their efficacy in the clinic, tyrosine kinase inhibitors do not eliminate leukemic stem cells, resulting in relapse and recurrence. Here, Applicant has shown that the small molecule IODVA1 inhibits VAV3 activation and reduces RAC signaling, eliminates leukemic stem cells and overcomes TKI-resistance in vivo. It prolongs the survival of PDX models of pediatric $Ph^+$ B-ALL and decreases the proliferation of primary cells from B-ALL patients ex vivo. IODVA1 thus may be used as an anti-tumor therapeutic agent.

Aberrant activation of RHO guanine nucleotide exchange factors (RhoGEFs) is believed to be a chief mechanism driving abnormal activation of their RhoGTPase targets in transformation and tumorigenesis. Consequently, a small molecule inhibitor of RhoGEF activities may be be used as an anti-cancer drug. Here, Applicant used cellular, mouse, and humanized models of RAC-dependent BCR-ABL1-driven and Ph-like lymphoblastic leukemia to identify VAV3, a tyrosine phosphorylation-dependent RacGEF, as the target of the small molecule IODVA1. Applicant found that IODVA1 binds tightly to VAV3, inhibits RAC activation and signaling, and increases pro-apoptotic activity in BCR-ABL1-transformed cells only. Consistent with this mechanism of action, both VAV3-deficient leukemic cells and mouse models of BCR-ABL1 leukemia do not respond to IODVA1. IODVA1 eradicates leukemic propagating activity of TKI-resistant BCR-ABL1 (T315I) B-ALL cells after treatment withdrawal by decreasing RAC signaling in vivo.

IODVA1 is superior to standard of care dasatinib and ponatinib at prolonging the survival of PDX models of relapsed pediatric $Ph^+$ and TKI-resistant $Ph^+$ B-ALL especially after treatment withdrawal. Cells representing pediatric ALL patients with diverse genetic lesions are highly sensitive to IODVA1 ex vivo and this sensitivity is VAV3-dependent. IODVA1 thus spearheads a novel class of drugs that inhibits a RacGEF, which may be used as an anti-tumor therapeutic agent.

RAC GTPases (RAC1, RAC2, RAC3, and RHOG) are tightly regulated signaling switches that mediate inputs from various receptors and oncogenes to regulate growth, apoptosis, cell-cell and cell-matrix interactions in response to growth factors such as EGF, PDGF, and HGF. Regulation of the actin cytoskeletal remodeling, which plays a key role in cell shape, polarity, division, migration and metastasis, is a major function of RAC[1]. RAC also controls cell cycle progression and cell survival, integrin-mediated adhesion, and is required for Ras transformation[2,3]. It is pivotal in most aggressive types of leukemias [4-6]. Thus, RAC has been associated with pro-tumorigenic functions and linked to the development of cancer. Moreover, RAC is characteristic of resistance to chemo-, radio-, and targeted-therapies and associated with persistence of leukemic stem cells[7,8].

Reducing RAC activity, specifically in cancer cells, is desirable and is an active area of research. However, no small molecule inhibitor of RAC signaling is in clinical use despite the many efforts. RAC activity is regulated by an intricate and well-orchestrated set of proteins comprised of guanine nucleotide exchange factors (GEFs), GTPase-activating proteins (GAPs), and guanine dissociation inhibitors (GDIs). RacGEFs activate RAC by exchanging the bound GDP to GTP to initiate signaling, while GAPs deactivate RAC by increasing the rate of GTP hydrolysis to arrest signaling. GDIs extract RAC from membranes, thereby preventing it from signaling. When activated, RAC binds to and activates downstream effectors such as the p21-activated kinases (PAK1/2/3), which in turn activate pro-survival pathways and actin-regulating proteins. RAC regulators and effectors are themselves subject to tight regulation. For example, VAV proteins (VAV1, VAV2, and VAV3) are multi-domain tyrosine phosphorylation-dependent RacGEFs. Phosphorylation of specific tyrosine residues releases an N- and C-terminal autoinhibition mechanism allowing RAC to access the Dbl-homology (DH) domain necessary for the GTP-exchange reaction [9,10]. Therefore, a small molecule inhibitor of RAC itself or of its activator, such as the VAV proteins, will provide an effective strategy for treatment of malignancies, especially leukemia, with aberrant RAC signaling.

The mechanism of action (MoA) of the small molecule IODVA1, a 2-guanidinobenzimidazole derivative with anti-tumorigenic properties is described herein. Initial characterization of IODVA1 ruled out kinase inhibition potential but showed that it decreases RAC activity and signaling and prevents actin cytoskeletal remodeling at low concentrations and within minutes of cell exposure. It also decreases cell-cell and cell-extracellular matrix interactions and reduces growth of Ras-driven tumors [11]. Applicant's studies showed the specificity of IODVA1 to oncogene-transformed cells. Here, in vitro and in vivo leukemic models of the chimeric BCR-ABL1 oncoprotein B-cell acute lymphoblastic leukemia ($Ph^+$ B-ALL) are used to study the MoA of IODVA1. Seemingly complex pathways activated by BCR-ABL1 all depend on the deregulated kinase activity of BCR-ABL1 and ABL1-tyrosine kinase inhibitors (ABL1-TKIs), e.g. imatinib, dasatinib, and ponatinib are used as first-line therapy. Thus, ABL1-TKIs can be used as positive control to assess the efficacy of IODVA1. However, despite tremendous success of TKIs in treating B-ALL in the clinic, appearance of mechanisms of TKI-dependent and -independent resistance limited their efficacy[12,13]. Thus, there is an unmet need for novel treatments of patients with TKI-resistant leukemia and treatments that prevent leukemic-cell persistence.

Additionally, BCR-ABL1 B-ALL models are well-suited for mechanistic studies. BCR-ABL1 B-ALL mutation in lymphoid committed progenitors is necessary and sufficient to induce B-ALL[5]. While genetic abnormalities including BMI1 upregulation[14], homozygous deletion of INK4A/ARF (CDKN2A) and mutations of the lymphoid transcription factors PAX5, IKZF1, and EBF1[15-17] cooperate with BCR-ABL1 in the progression to aggressive B-ALL, these mutations are not present in all cases of pediatric BCR-$ABL1^+$ B-ALL[16,18] Recurrent epigenetic alterations have also been identified across all B-ALL subtypes and genes frequently affected by structural abnormalities have been shown to be targets for aberrant DNA methylation[19].

Expression of BCR-ABL1, which has constitutive kinase activity, is sufficient to promote the growth advantage of leukemic cells. When expressed, BCR-ABL1 activates a variety of pathways including the Ras-mitogen-activated protein kinase (MAPK) leading to abnormal cell proliferation, the Janus-activated kinase (JAK)-STAT pathway leading to impaired transcriptional activity, and the phosphoinositide 3-kinase (PI-3K)/AKT pathway resulting in prolonged survival[20]. This signaling pathway is mimicked by the Ph-like lymphoblastic leukemias, which include mutations resulting in similar transcriptomes[21]. Expression of p190- or p210-BCR-ABL1 or Ph-like mutations activates RAC signaling pathways to regulate leukemogenesis[22] and deleting RAC isoforms alone impairs leukemogenesis induced by p190- or p210-BCR-ABL1 expression in the hematopoietic stem and progenitor cell compartment[4,5,23,24]. Genetic intervention of VAV3-dependent signaling axis inhibits leukemic cell survival in vitro and in vivo and sensitizes lymphoblastic leukemia cells to TKI [23].

Applicant found that IODVA1 binds tightly and inhibits VAV3, consequently leading to the inhibition of RAC activation and of its downstream signaling and to the induction of apoptosis specifically in BCR-ABL1-transformed cells in vivo and in vitro. Applicant further found that a single agent IODVA1 is better than dasatinib or ponatinib at prolonging the survival of a mouse model of TKI-resistance and of two patient-derived xenograft (PDX) models of wild-type and TKI-resistant $Ph^+$ BCR-ABL1 and reducing leukemic burden long after treatment withdrawal. Applicant also found that IODVA1 is effective in decreasing proliferation and survival of primary cells derived from patients with relapsed and de novo ALL leukemias in a VAV3-dependent manner. IODVA1 is believed to be the first inhibitor of a RhoGEF with in vivo activity against PDX mouse models of cancer. Thus, the disclosed compounds and methods may be used for overcoming TKI-resistance and for treating cancers where VAV3 is a target, including Ras-driven cancers.

Results

Figure 1B:
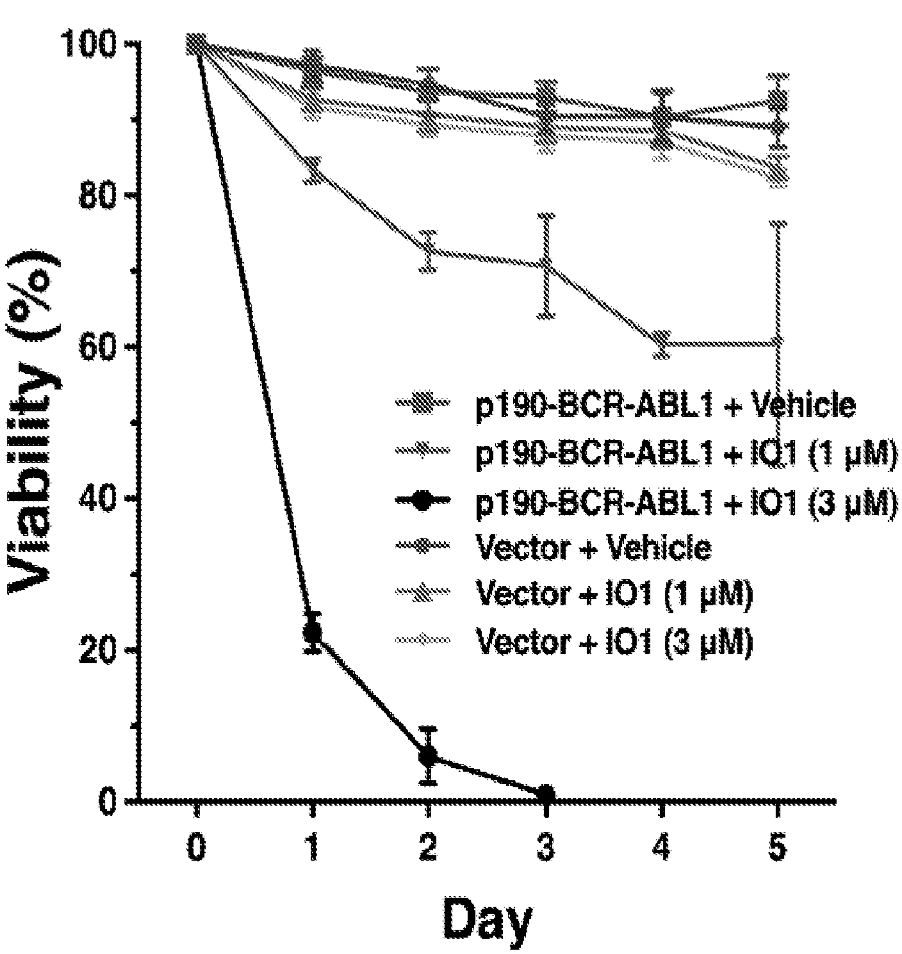

IODVA1 specifically targets BCR-ABL1 B-ALL cells in vitro. To confirm that IODVA1 is specific for oncogene-transformed cells, Applicant tested its efficacy on the proliferation and survival of $CD34^+$ human peripheral blood mononuclear cells transduced with p190-BCR-ABL1. Expression of BCR-ABL1 increased cell proliferation (FIG. 1A, gray line, squares) as compared to the empty vector. Treatment with IODVA1 (IO1, 1 μM, black line, downward triangles) decreased proliferation of BCR-ABL1-transformed cells but did not affect the proliferation of empty vector-transduced cells. Applicant then assessed the survival of p190-BCR-ABL1-transformed $CD34^+$ cells in the presence of IODVA1 by trypan blue exclusion (FIG. 1B). The survival of p190-BCR-ABL1 expressing cells decreased in a dose-dependent manner to 60±16% (SEM, N=3) at 1 μM on day 5 (gray line, downward triangles) and to 1±0.2% (SEM, N=3) at 3 μM on day 3 (black line, circles). Survival of empty vector-expressing cells was not affected by IODVA1. IODVA1 irreversibly inhibited the survival of p190- and p210-BCR-ABL1 but not of empty vector (Mieg3)-expressing Ba/F3 cells with a half maximal effective concentration (EC50) of 380 nM, Nalm-1 cells with an EC50 of 680 nM, and inhibited the clonogenic ability of BCR-ABL1-transformed Ba/F3 cells in soft agar (FIG. 8A-8D). Together, these results indicate that IODVA1 specifically targets proliferation and survival of BCR-ABL1-transformed cells and are consistent with Applicant's findings that IODVA1 is more specific to oncogene expressing cells [11].

Figure 1C:
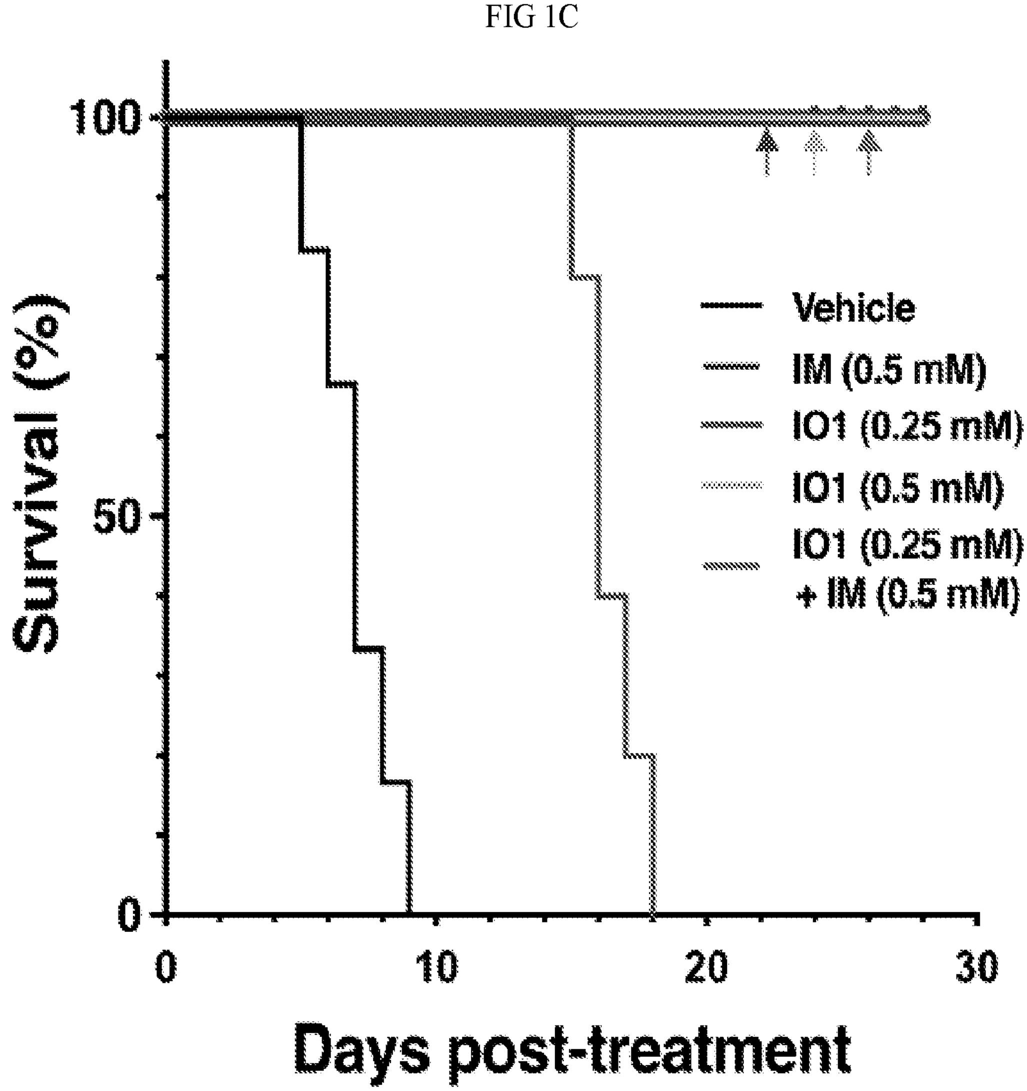

IODVA1 prevents leukemia-related death and significantly decreases the leukemic burden in a BCR-ABL1-induced leukemic murine model. To test if potency of IODVA1 on cells can be recapitulated in vivo, Applicant probed it on a murine model of p190-BCR-ABL1 induced B-ALL and compared it to imatinib, an ABL1-TKI with well-characterized MoA used as first-line therapy in $Ph^+$-induced malignancies in the clinic. C57Bl/6 mice were used as donors and/or recipients of transduction/transplantation model. Mouse low-density bone marrow (LDBM) cells were transduced with a MSCV-driven bicistronic retroviral vector (MSCV-IRES-EGFP) encoding p190-BCR-ABL1. Transduced LDBM cells ($1\times10^6$) were intravenously transplanted into lethally irradiated C57Bl/6 mice. Mice were bled post 23 days and $GFP^+$ cells were analyzed by flow cytometry to assess leukemic burden. All mice had developed leukemia by day 28. Mice were stratified into 5 groups (5 mice per group) and administered either PBS vehicle control, 0.25 or 0.5 mM IODVA1, 0.5 mM imatinib, or the combination 0.25 mM IODVA1+0.5 mM imatinib. Vehicle control group had the same DMSO amount (0.1%) as the other groups. Drugs were administered subcutaneously in osmotic pumps for continuous slow release for 4 weeks. Kaplan-Meier survival plots show that while the control group had died within 7 to 9 days post administration of the vehicle control (black line), the low IODVA1 dose (0.25 mM) increased survival by an average of 10 days (dark gray line). Mice treated with imatinib, the higher IODVA1 dose or the combination were alive for the 4-week duration of the therapy (FIG. 1C). Significantly, IODVA1 decreased the residual p190-BCR-ABL1-expressing leukemic progenitor B-cells ($EGFP^+$/$B220^+$) from peripheral blood (PB) of treated mice (FIG. 8E).

Figure 1D:
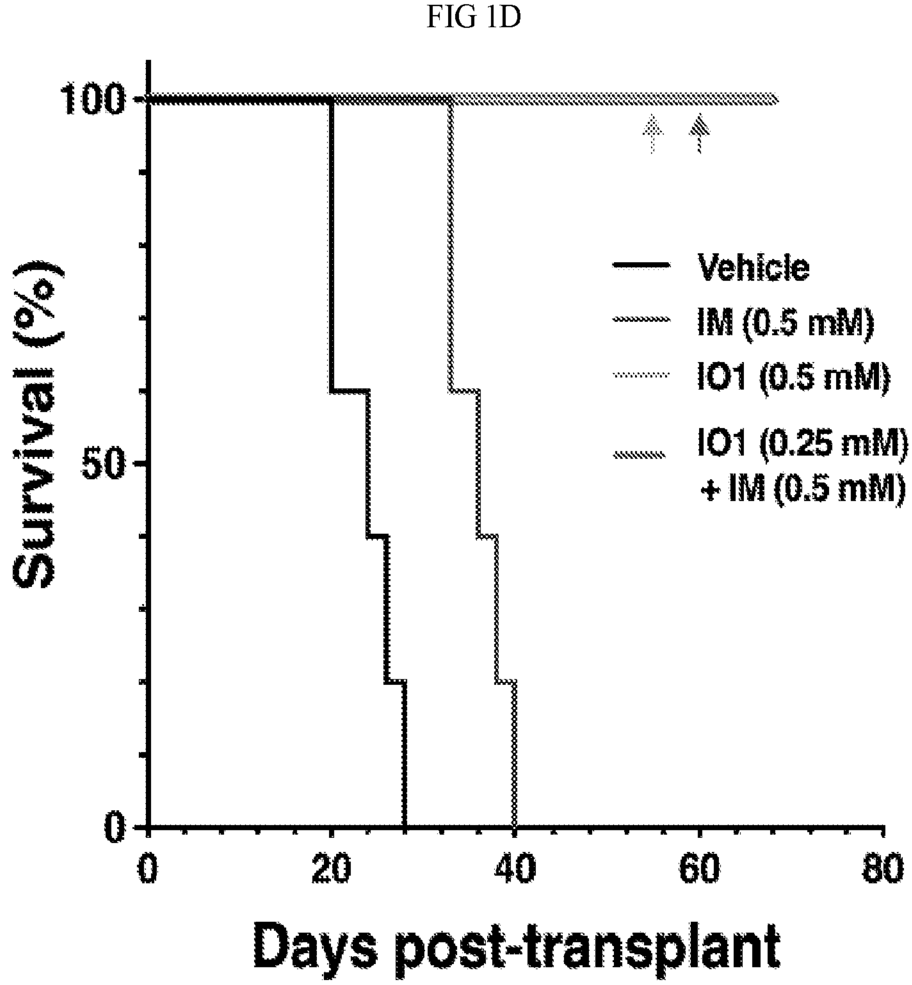

IODVA1 eradicates leukemic propagating activity assessed by serial transplantation. Despite its significant clinical success, imatinib and, more generally, TKIs do not eliminate leukemic stem/progenitor cells in the bone marrow (BM), which can lead to residual disease, appearance of mechanisms of resistance, and ultimately relapse [25,26] To determine if IODVA1 eradicates ability of progenitor B cells to propagate tumors, as a functional surrogate of minimal residual disease capable of leukemia relapse, BM cells from vehicle-control, imatinib, the highest IODVA1 dose or the combination-treated mice from FIG. 1C were transplanted into lethally irradiated secondary C57BL/6 recipients in a limiting dilution series of $1\times10^6$, $0.3\times10^6$, and $0.1\times10^6$ cell doses and monitored for leukemia development and survival in the absence of any additional therapy. Kaplan-Meier survival plots for the $10^6$-cell dilution transplant indicate that administration of IODVA1 alone or in combination with imatinib resulted in survival of p190-BCR-ABL1 chimeric mice beyond the 70-day endpoint analysis (FIG. 1D). Mice transplanted with BM cells from primary recipient mice treated with imatinib alone died by day 40 post-transplantation. Analysis at week 5 post transplantation of the leukemic progenitor cells ($EGFP^+$/B220+) from the peripheral blood of secondary transplant mice (FIG. 8F) indicates that IODVA1 is better than imatinib at eradicating leukemic cell burden. Poisson's distribution analysis of the lower cell dose transplantations (FIG. 8G-8J) indicates >10-fold depletion of tumor propagating activity in grafts from IODVA1- or IODVA1+imatinib-treated leukemic mice compared with leukemic mice treated with imatinib alone.

Figure 2A:
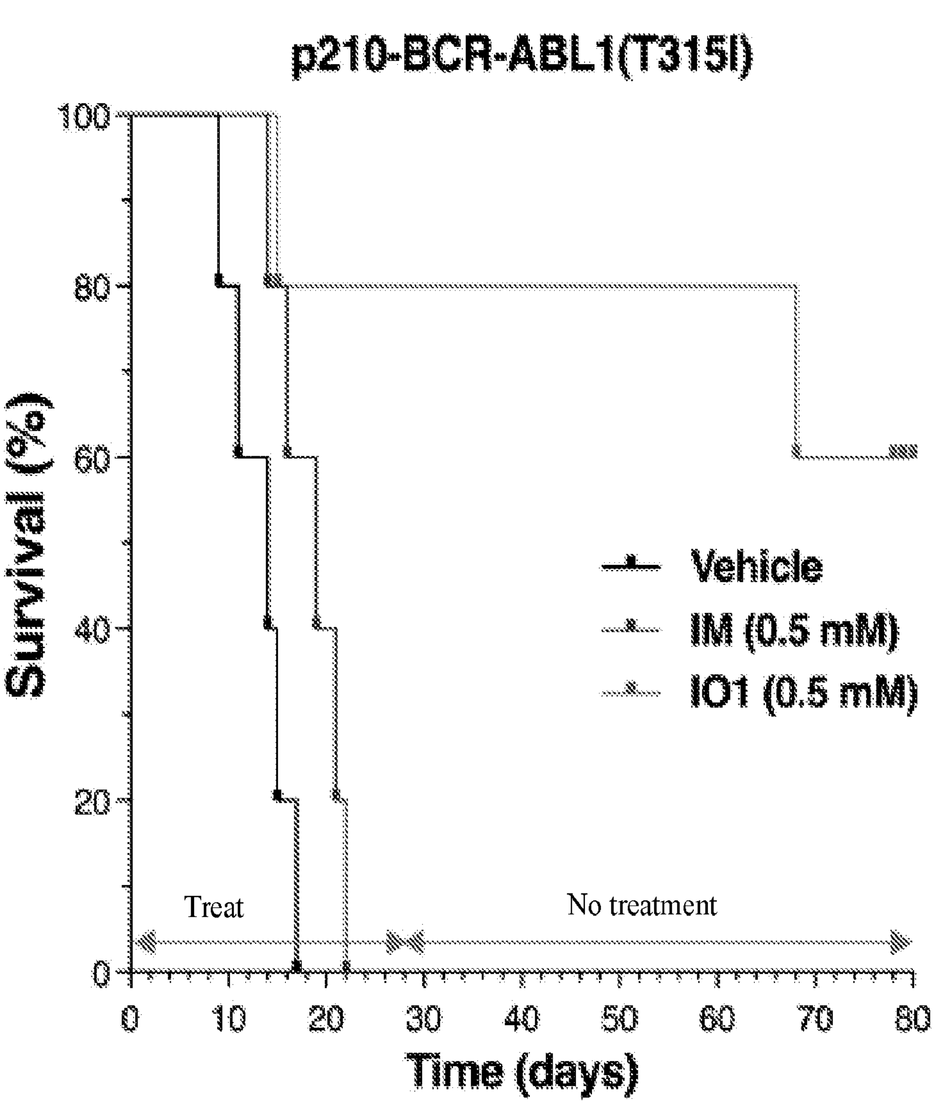
FIGS. 2A-2F depict data showing that IODVA1 increases the survival of PDX models of $Ph^+$ B-ALL better than ABL1-TKIs. Mice engrafted with LDBM cells transduced with TKI-resistant p210-BCR-ABL1 (T315I) gatekeeper mutant. Treatment was delivered continuously for 28 days via surgically implanted subcutaneous pumps (N=5 per treatment group). After 28 days, mice were monitored without any additional treatment. (2A) Kaplan-Meier survival plot of mice with imatinib-resistant leukemia. Pumps either carried vehicle control (black line), 0.5 mM imatinib (IM, gray line), or 0.5 mM IODVA1 (IO1). (2B) Percentage of leukemic progenitors ($EGFP^+$) B-cells in peripheral blood (PB) were assessed by flow cytometry at the indicated week and plotted. Only IODVA1-treated mice remained alive for analysis at weeks 5, 7, and 10. (2C) and (2D)—NSG mice engrafted with B-ALL patient sample 2018-136 were treated days 22-50 with vehicle, IODVA1, dasatinib, IODVA1+dasatinib, ponatinib, IODVA1+ponatinib. Treatment duration is highlighted by a gray rectangle. N=5 mice per treatment group. (2C) Kaplan-Meier survival plot of PDX 2018-136-engrafted mice during treatment and after treatment withdrawal. (2D) Leukemic cell burden assessment in the peripheral blood of PDX-implanted mice at the indicated time points. (2E) and (2F)—Patient sample 2017-129 was engrafted as in (2C) and (2D), except mice were treated only with vehicle, IODVA1, ponatinib and IODVA1+ponatinib combination.
Figure 2B:
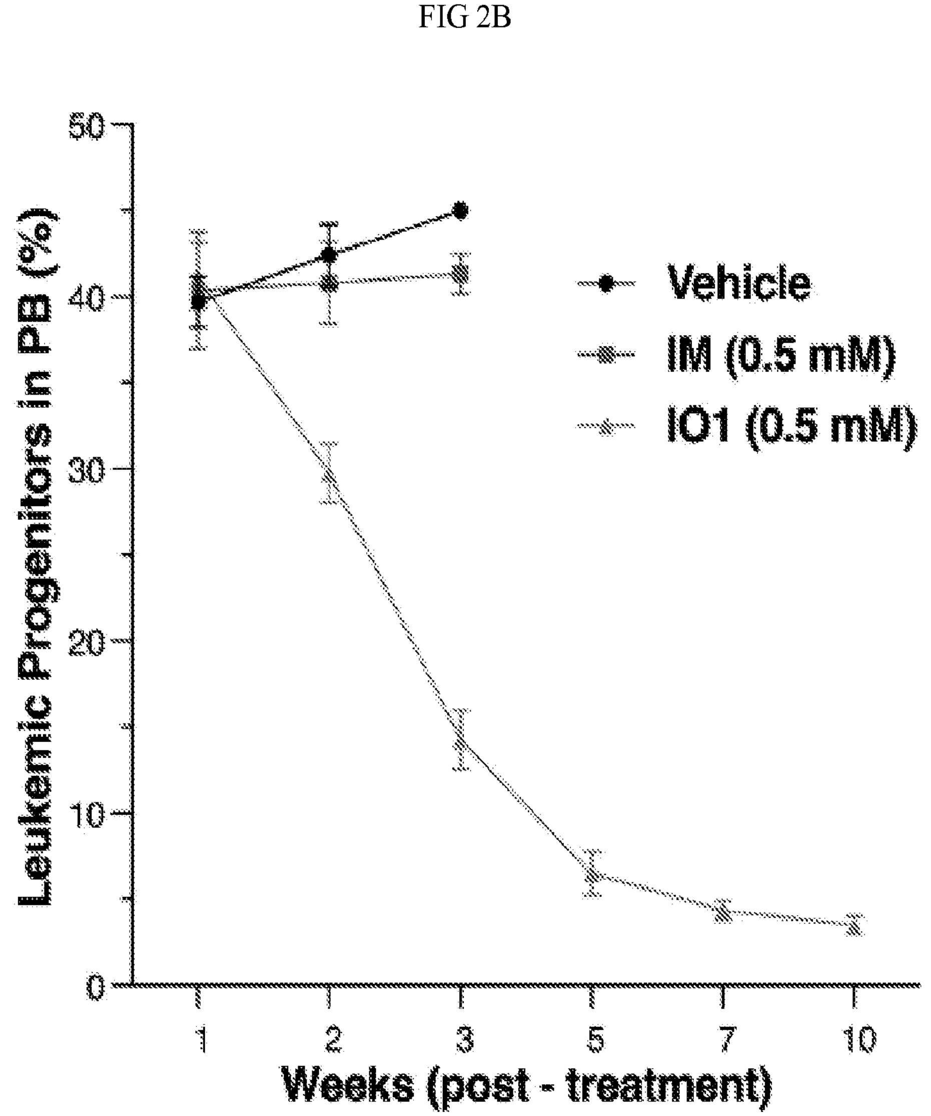
Figure 9:
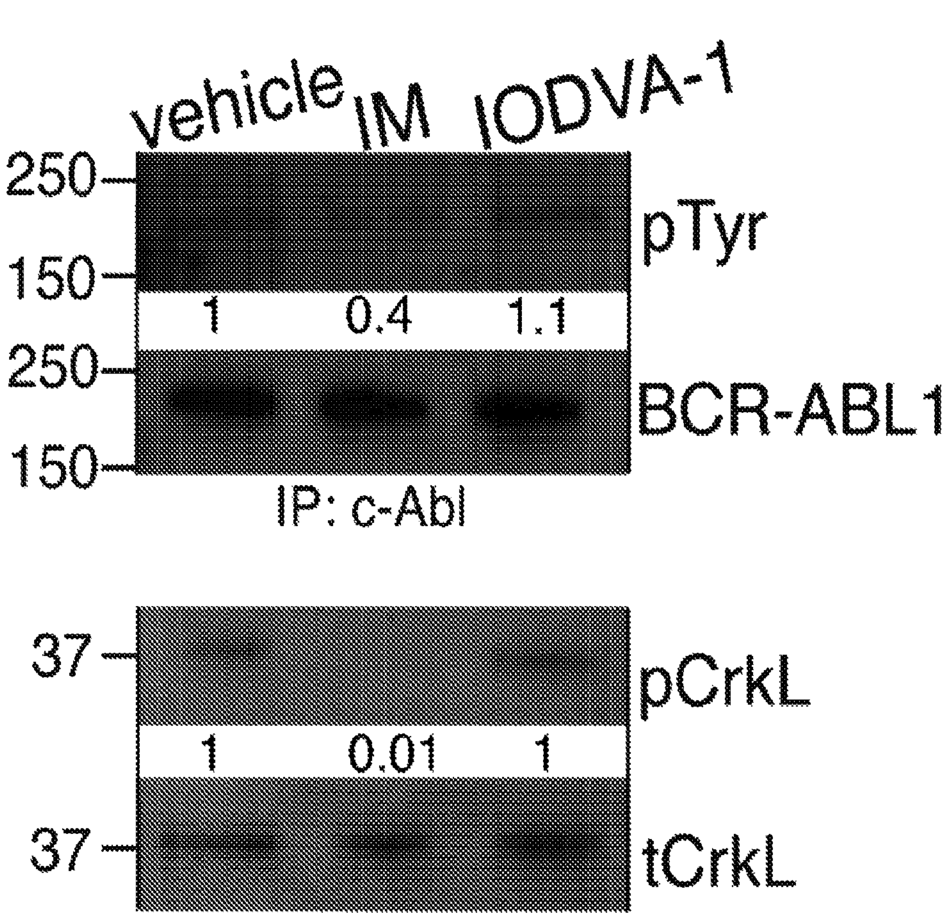
FIG. 9 depicts data showing that IODVA1 does not affect p190-BCR-ABL1 phosphorylation status. Ba/F3 cells expressing p190-BCR-ABL1 were treated with vehicle control, imatinib (IM, 1 μM), or IODVA1 (3 μM) for 4 h. Lysates were immunoprecipitated with ABL1 antibody and the protein complex separated on SDS-PAGE and immunoblotted for phosphotyrosine (pY) and BCR-ABL1 (c-Abl) and quantified. Lysates were also immunoblotted for pCrkl and total Crkl and quantified. IP—immunoprecipitation, IB—immunoblotting.

IODVA1 eradicates TKI-resistant BCR-ABL1 B-ALL by decreasing RAC signaling. IODVA1 has no inhibitory activity in vitro against major wild-type kinases including ABL1 and SRC-like kinases [11]. To confirm that it does not target BCR-ABL, Applicant immuno-precipitated p190-BCR-ABL1 from p190-BCR-ABL1-Ba/F3 cells treated with vehicle control or IODVA1 (3 μM) for 4 h and checked p190-BCR-ABL1 phosphotyrosine levels by immunoblotting. IODVA1 treatment did not affect the phosphorylation level of p190-BCR-ABL1 (FIG. 9). Thus, the anti-proliferative activity of IODVA1 towards in vitro and in vivo BCR-ABL1 B-ALL models and its ability to eradicate residual disease cannot be explained by ABL1 inhibition. To further test this idea, Applicant evaluated the ability of IODVA1 to increase the survival of mice harboring p210-BCR-ABL1 (T315I) gatekeeper mutant. This ABL1 mutant was selected because it is one of the most common compound mutations arising in patients on imatinib therapy[27]. Mice were treated for 4 weeks with two rounds of pumps containing vehicle control, imatinib, or IODVA1. At the end of the 4-week treatment, surviving mice were kept in their cages without any additional treatment. As expected, p210 (T315I) mice did not respond to the TKI as all imatinib-treated mice died by day 22, before the end of the treatment (FIG. 2A). 80% of IODVA1-treated mice survived until day 65, or 37 days post treatment withdrawal. 60% of IODVA1-treated mice survived till day 80, or 52 days post treatment withdrawal (FIG. 2A). Counts of $EGFP^+$/$B220^+$ leukemic progenitor cells from the T315I-leukemic mice peripheral blood indicated that treatment with IODVA1 alone significantly decreased leukemic progenitor levels by 24% by week two, by 84% by week 5, and by 91% by week 10 (FIG. 2B). Even though treatment had ended by week 4, counts of leukemic progenitor cells kept decreasing in IODVA1 treated mice.

Figure 6A:
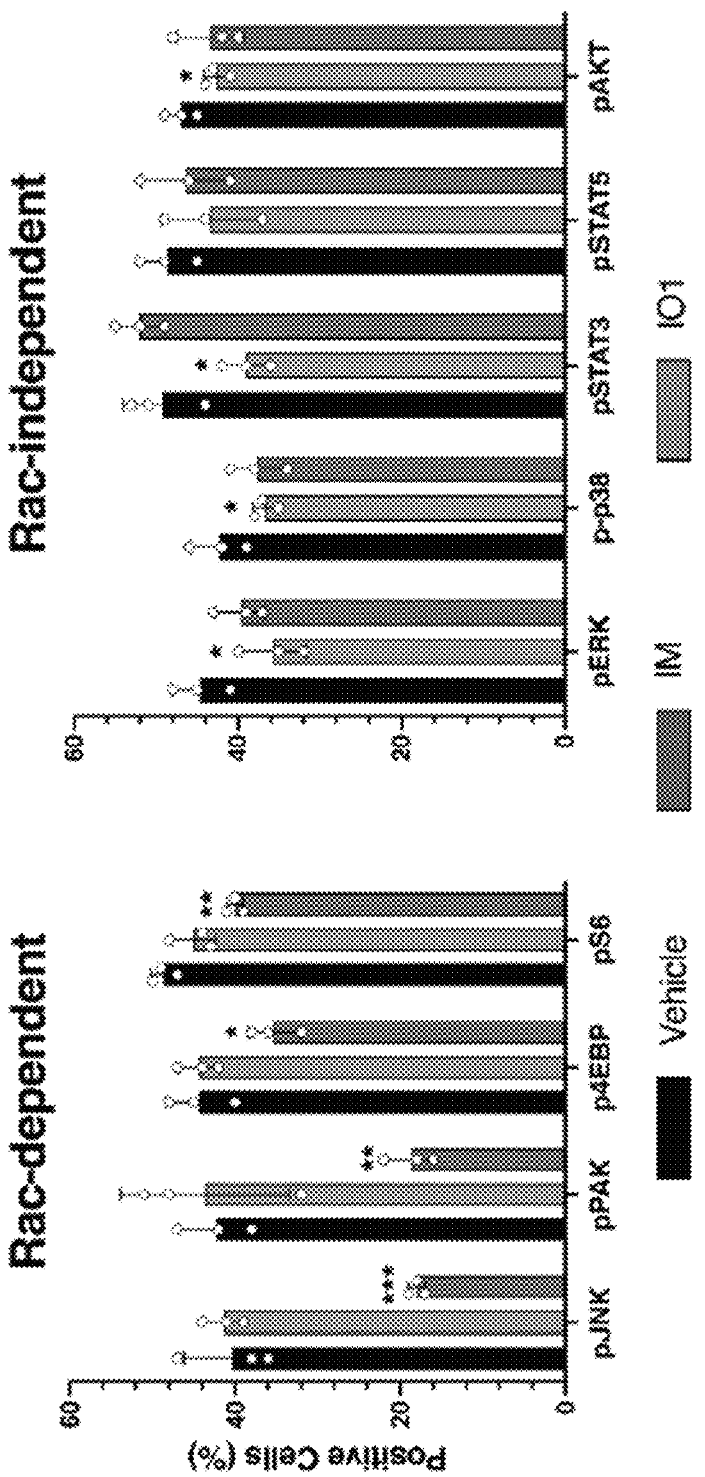
FIGS. 6A-6C depict data showing that IODVA1 decreases the VAV3/RAC signaling pathway in vivo. (6A) Bar graphs of pharmacodynamic assessment of leukemic progenitor cells (%) from the 2-week treated mice with vehicle control (black), imatinib (gray), or IODVA1 from FIG. 2A using phospho-flow cytometry of the indicated RAC-dependent and -independent effectors. *p≤0.05, p≤0.01, *p≤0.001 using One-way ANOVA with Dunnet's multiple comparison test. (6B) $CD34^+$ cells or anti-human $CD19^+/CD45^{dim}$ sorted cells from the indicated PDX specimen (see Table 1) were incubated in the presence of vehicle or IODVA1 (1 μM) for 30 min and processed for immunoblotting analysis for phospho- and total-VAV3, -PAK1 and phospho-VAV1. Phospho-proteins band densities were normalized to the total protein (pVAV3 and pPAK) or GAPDH (pVAV1) and quantified relative to their respective vehicle treatments. (6C) Bone marrow aspirates from vehicle-treated mice at time of death (day 32) or IODVA1+ponatinib-treated mice from PDX 2018-136 and PDX 2017-129 at the end of treatment (day 50) and the last day post-relapse from FIGS. 2C & 2D were subjected to phospho-PAK1 analysis by flow cytometry (bar graph) or resolved by SDS-PAGE, blotted for pVAV3, and normalized to GAPDH (immunoblot). Mice were randomly pooled into two groups of 3 labeled 1 & 2. n.s.—not significant, *p≤0.05; **p≤0.01 based on One-way ANOVA with Tukey's multiple comparisons test.

To assess signaling pathways affected by IODVA1, $EGFP^+/B220^+$ LDBM cells were isolated from two-week treated p210 (T315I) mice, stained with phospho-antibodies against the pro-proliferative RAC-dependent effectors JNK, PAK1/3, 4EBP, and S6 and the RAC-independent effectors ERK1/2, STAT3, STAT5, p38, and AKT, and analyzed by flow cytometry. IODVA1 resulted in significant decreases in pJNK by 55% (p=0.003), pPAK1/3 by 56% (p=0.008), p4EBP by 20.3% (p=0.026), and pS6 by 17.8% (p=0.002), respectively (FIG. 6A). Phosphorylation levels of ERK, p38, STAT3, STAT5, and AKT were not affected by IODVA1. Interestingly, imatinib had the opposite effect, it decreased the levels of pERK, p-p38, pSTAT3, and pAKT but did not affect the phosphorylation levels of the RAC-dependent effectors. Taken together, IODVA1 not only overcomes TKI-resistance but also eliminates TKI-resistant leukemic stem/progenitor cells likely by acting on imatinib-independent growth signaling pathways that involve RAC effectors.

Figure 3A:
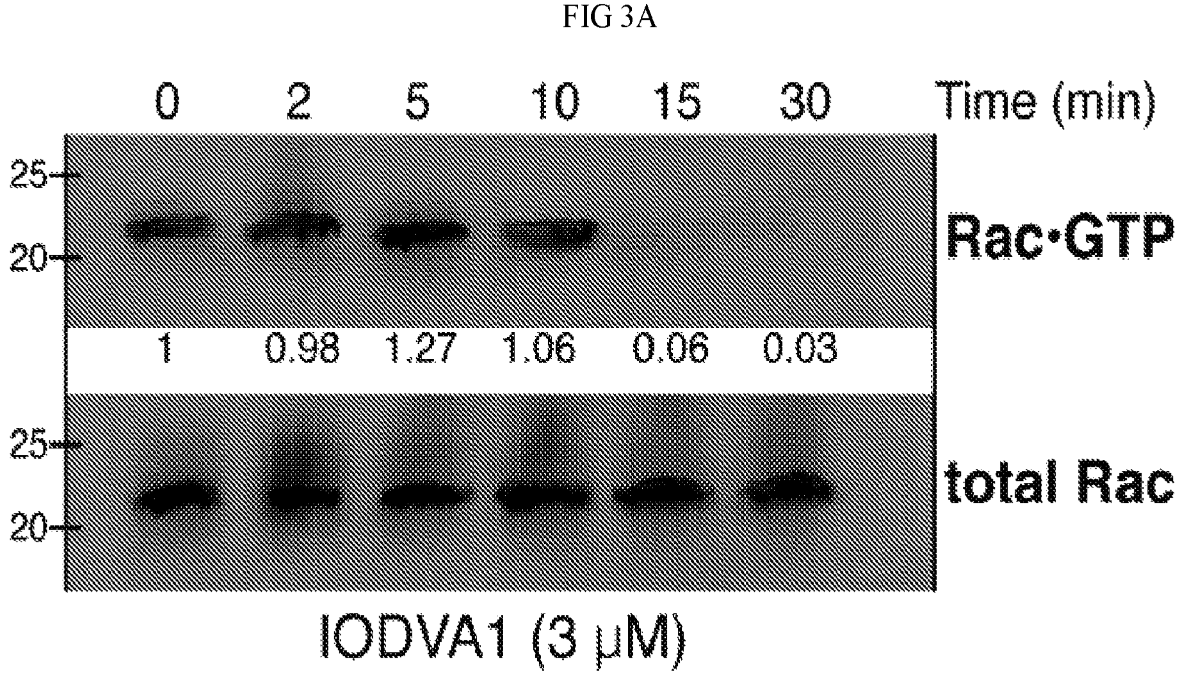
FIGS. 3A-3D depict data showing that IODVA1 targets RAC activation and signaling. (3A) Effect on active RAC (RAC·GTP) in p190-BCR-ABL1 expressing Ba/F3 cells treated with IODVA1 (3 μM) as indicated. Active RAC levels were assessed by pull-down using GST-PAK-GBD, followed by immunoblotting and densitometric quantification. Results are representative of two independent experiments. (3B) Bar graph of results of the phospho-flow cytometry analysis of pJNK, pS6, p4EBP, pPAK1, and pAKT of Ba/F3 cells expressing empty vector or p190-BCR-ABL1 and treated with vehicle control or IODVA1 (3 μM) for 30 min. (3C) Bar graph of a representative cell cycle analysis of p190-BCR-ABL1-Ba/F3 cells treated with vehicle control or IODVA1 (1, 3, and 10 μM) for 20 h. (3D) Quantification of the average number of colonies of bone marrow wild-type and $Rac1^{\Delta/\Delta}$+$Rac2^{-/-}$ p190-BCR-ABL1 leukemic cells treated with vehicle control or IODVA1 (IO1, 1 μM). ns—not significant, *p≤0.05, p≤0.01, *p≤0.001, **p≤0.0001 using One-(3B and 3D) or Two-way ANOVA (3**C) with Tukey's multiple comparison test.

IODVA1 decreases RAC activity and downstream signaling. Applicant has previously shown that IODVA1 prevents formation of actin suprastructures, such as lamellipodia and circular dorsal ruffles, within minutes of cell incubation and decreases RAC activation and PAK1/2 phosphorylation in MDA-MB-231 breast cancer cells[11]. RAC is a major regulator of lamellipodia formation and of JNK and TORC1 activities [28,29] and is required for circular dorsal ruffle formation and is also activated downstream of BCR-ABL1. Applicant thus tested if IODVA1 inhibits RAC activation and measured levels of RAC-GTP during treatment using PAK-GBD (GTPase-binding domain) in BCR-ABL1-transformed cells. Incubation of p190-BCR-ABL1 transformed Ba/F3 cells with IODVA1 (3 μM, FIG. 3A) substantially decreased levels of active RAC within 10-15 minutes. IODVA1 is specific to RAC (IC50=1 μM) and is less effective on CDC42 and not at all on RHOA (FIGS. 11A & 11B), consistent with previous observations in MDA-MB-231 cells [11].

Figure 3B:
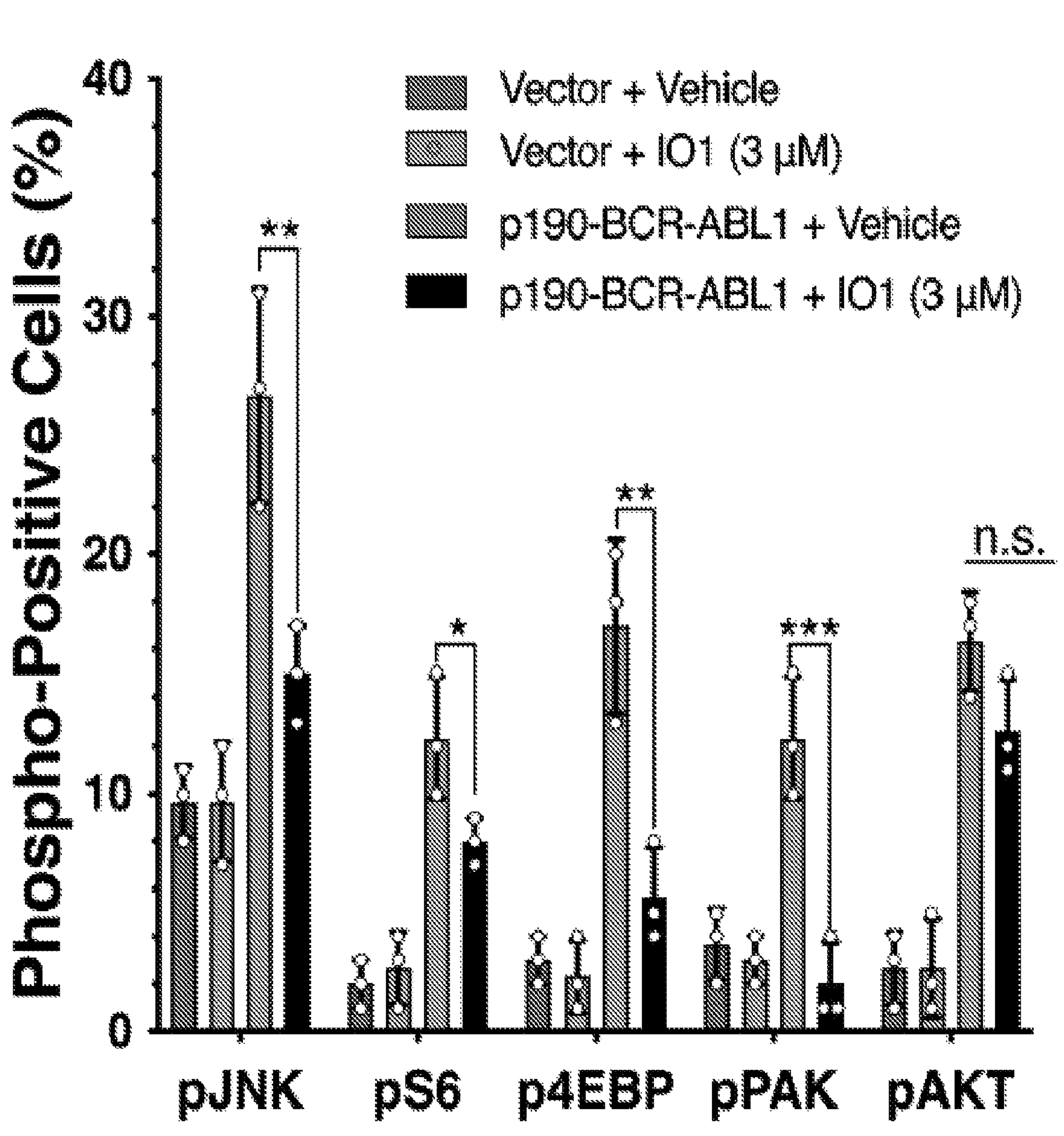

To test if the decrease in RAC activation is translated into a decrease in its downstream signaling in vitro as was observed with xenograft-derived TKI-resistant p210 (T315I) cells (FIG. 6A), Applicant analyzed vehicle- and IODVA1-treated p190-BCR-ABL1 or empty vector expressing Ba/F3 cells by phospho-flow cytometry. Expression of BCR-ABL1 increases the phosphorylation levels of JNK, S6, 4EBP, PAK1/2, and AKT by more than 2.5 times (FIG. 3B, gray bars). IODVA1 decreases the phosphorylation levels of JNK by 1.8 (p=0.004), S6 by 1.5 (p=0.046), 4EBP by 3.0 (p=0.001), and PAK by 6.1 (p=0.0005) fold, respectively (black bars). IODVA1-induced decrease in the phosphorylation levels of effectors is specific to BCR-ABL1- but not empty vector-expressing cells. IODVA1 did not affect the phosphorylation levels of AKT regardless of the BCR-ABL1 status (FIG. 3B). The decrease in JNK, S6, and 4EBP activity in IODVA1-treated Ba/F3 cells mirrors the decrease observed in LDBM cells from IODVA1-treated p210 (T315I) mice in pharmacodynamics studies (FIG. 6A). Together, in vitro and in vivo data are consistent with IODVA1 targeting activation of RAC and its downstream signaling in leukemic models.

Figure 3C:
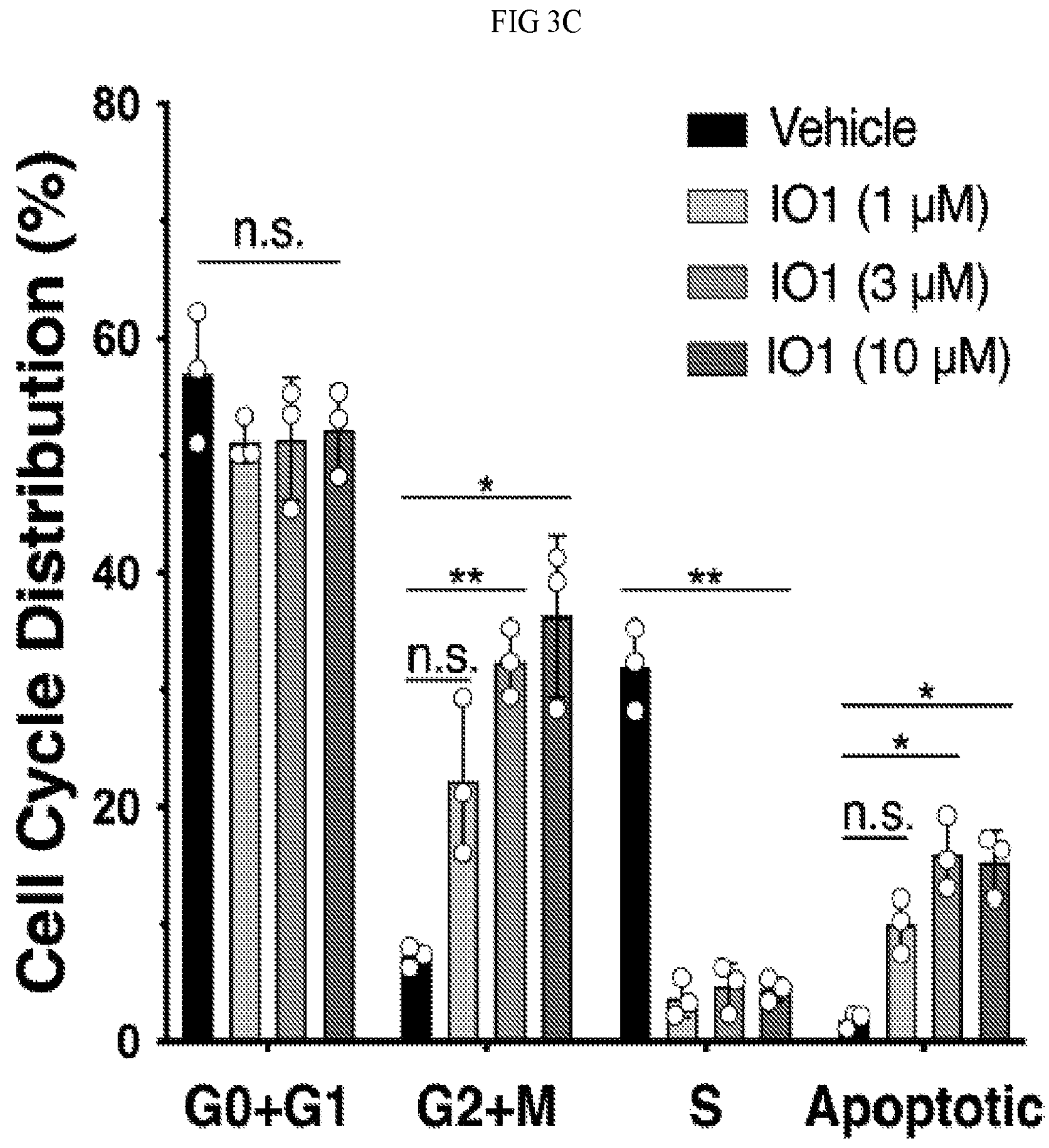

IODVA1 decreases RAC downstream pro-survival PAK and decreases inhibitory phosphorylation of pro-apoptotic BAD Ser136 activities within minutes of cell exposure (FIG. 11C). The decrease in PAK and BAD phosphorylation suggests that IODVA1 promotes reduction in survival and induction of apoptosis. To further test this hypothesis, Applicant analyzed the cell cycle of p190-BCR-ABL1 leukemic progenitor cells ($EGFP^+/B220^{dim}$) incubated with vehicle control or IODVA1 (1-10 μM) for 20 h, followed by in vitro BrdU incorporation and flow cytometry analysis (FIG. 3C). IODVA1 did not affect the G0+G1 phase but significantly changed the distribution of the G2+M, S, and apoptotic phases. It increased the percentage of cells in the G2+M phases from 7±1% (SEM, N=3) in the presence of vehicle control to 22±6.6, 32±3, and 36±7% (SEM, N=3) at 1, 3, and 10 μM, respectively. At 1 μM, it reduced the S-phase 8-fold (p=0.005) and increased apoptosis by at least 5.3-times. Therefore, IODVA1 increases percentage of cells in G2/M phase, induces S-phase arrest and increases apoptosis.

Figure 3D:
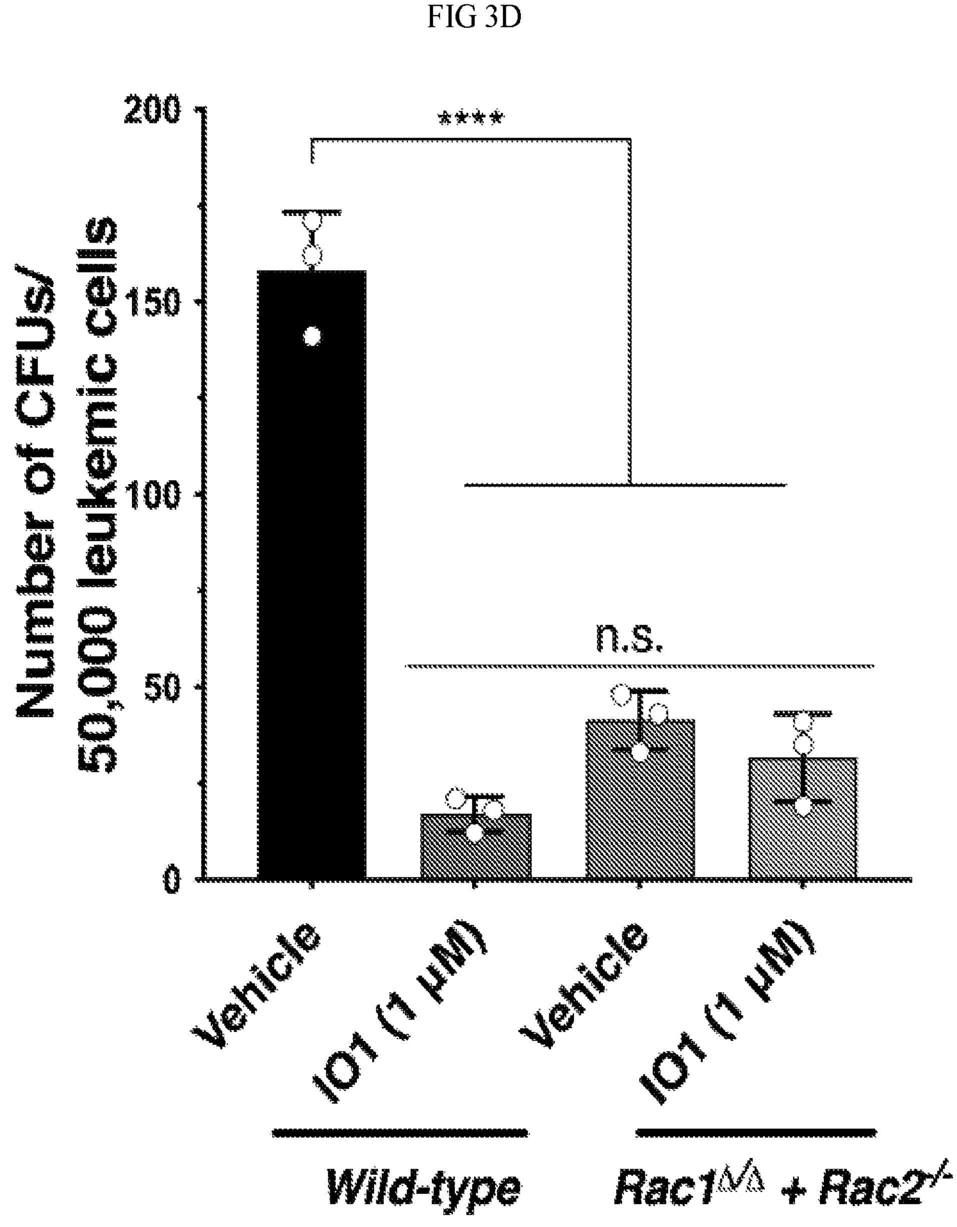
Figure 10A:
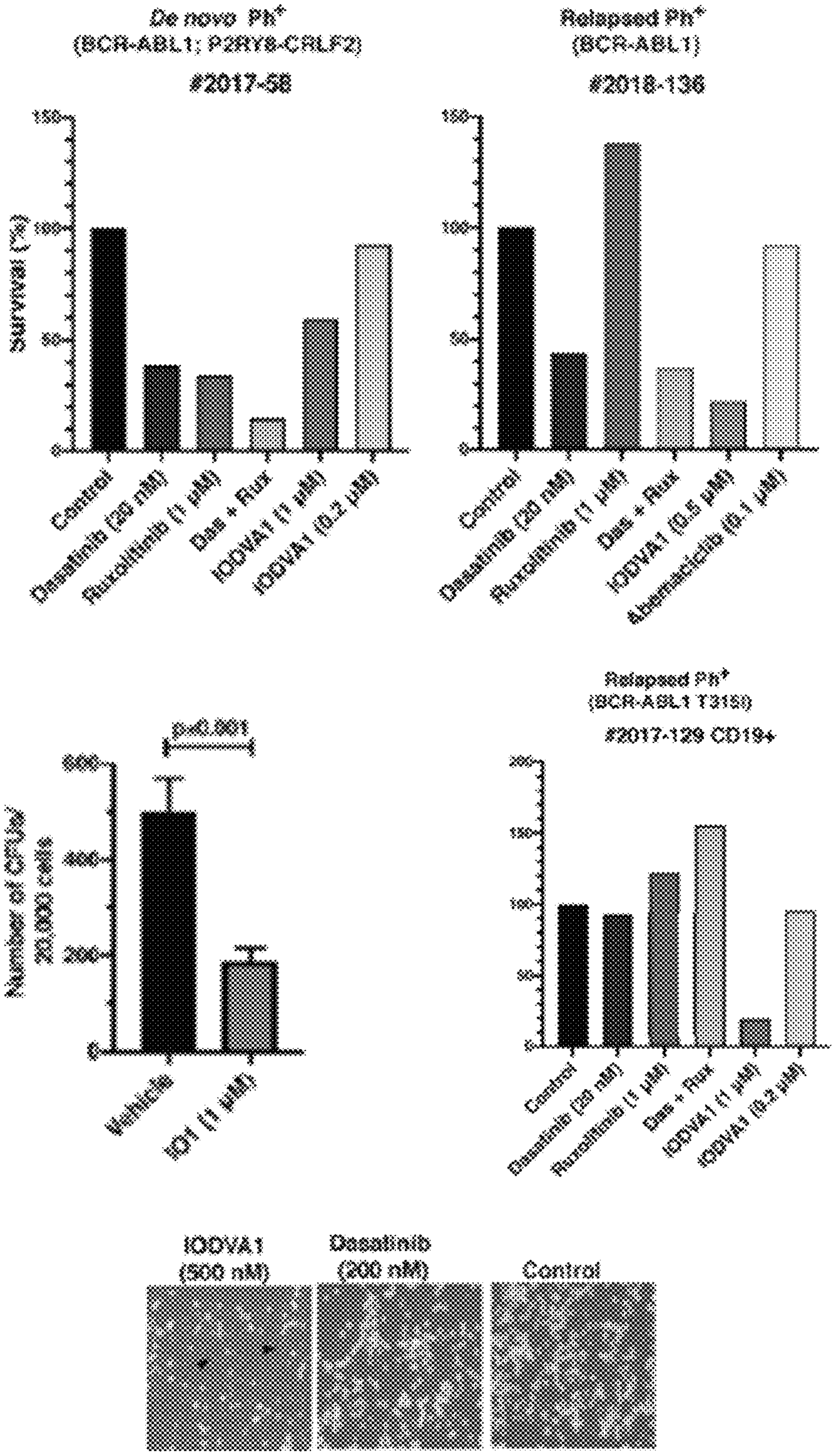
FIGS. 10A-10D depict data showing that IODVA1 reduces survival of leukemic cells derived from relapsed and de novo $Ph^+$, Ph-like and MLL pediatric patients. Patient derived xenograft (PDX) cells were co-cultured ex vivo on MS-5 or OP-9 stromal cells and treated with dasatinib (Das, ABL1-inhibitor), ruxolitinib (Rux, JAK-inhibitor), combination of dasatinib and ruxolitinib (Das+Rux), abemaciclib (CDK inhibitor), or IODVA1 at the indicated concentrations and assessed for survival using flow cytometry. (10A) Representative survival of leukemic cells from patients with $Ph^+$ rearrangements. Cells from sample #2018-136 were also subjected to clonogenic assay. Also note example image from #2017-129 cells treated with control, dasatinib or IODVA1 showing no effect on cells of normal stroma (black arrows). (10B) Leukemic cells from patients with de novo Ph-like leukemia. (10C) Leukemic cells from MLL/AF9 and relapsed MLL/AF1q patients. (10D) Cells from PDX Ph-like cells 2016-79 and 2018-132 with the same (IGH-CRLF2; JAK2) rearrangement were incubated with IODVA1 (1 μM) for 4 h, lysed, and immunoblotted for pVAV3 and VAV3; GAPDH was used as loading control.
Figure 10B:
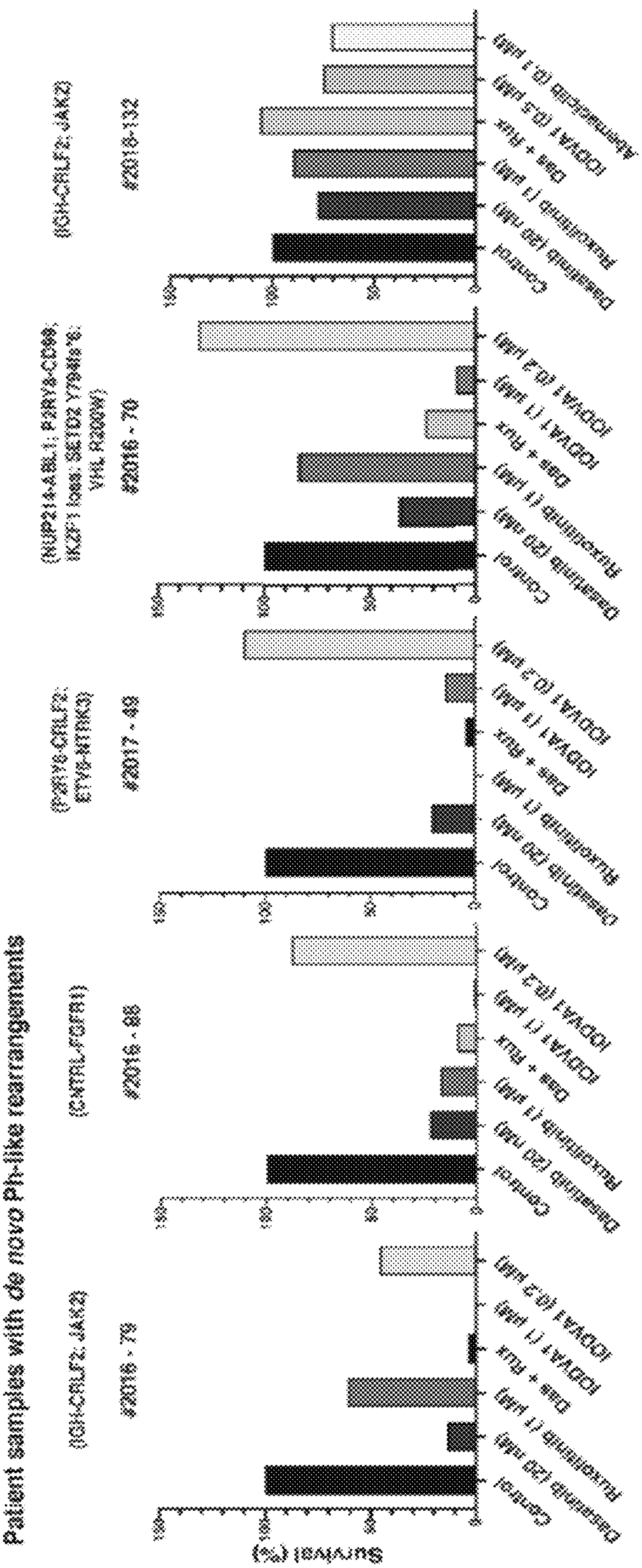
Figure 10C:
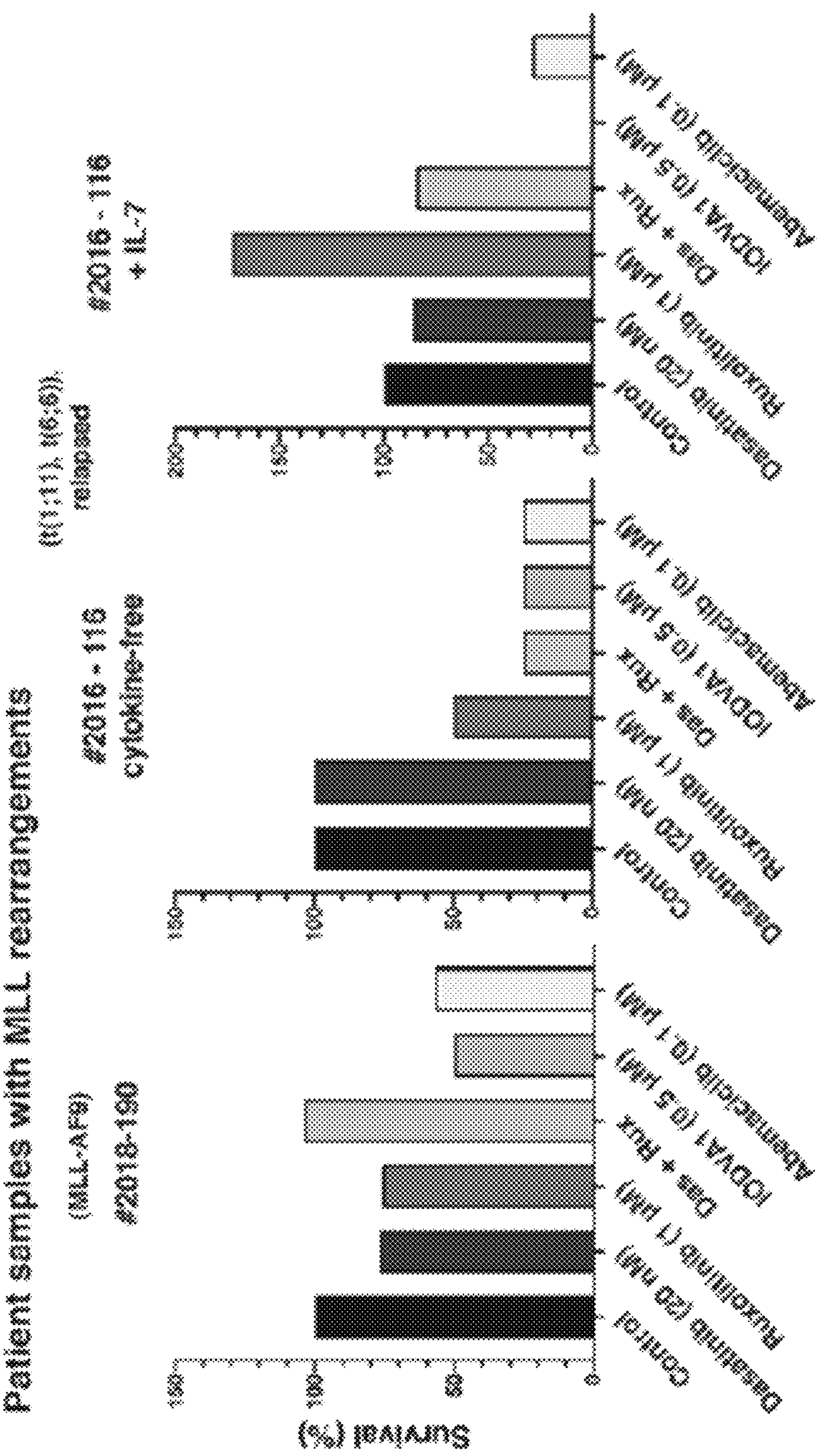
Figure 10D:
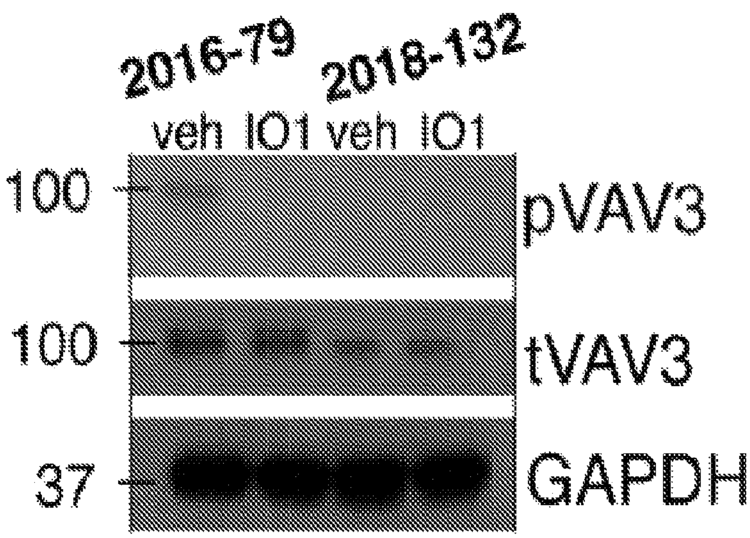

RAC-deficient cells do not respond to IODVA1. To confirm that IODVA1 targets RAC-dependent pathways, Applicant assessed its effects in a RAC2-null background. $RAC1^{\Delta/\Delta}+RAC2^{-/-}$-murine leukemic cells show severe reduction in RAC1 expression and are deficient in RAC2 (FIG. 10D). $RAC1^{\Delta/\Delta}+RAC2^{-/-}$ or wild-type murine leukemic cells expressing p190-BCR-ABL1 [30] were tested for clonogenic ability in the presence of IODVA1 (FIG. 3D). $RAC1^{\Delta/\Delta}+RAC2^{-/-}$-leukemic cells formed 3.8-times less colonies than wild-type leukemic cells. IODVA1 significantly decreased the ability of wild-type cells to form colonies but did not alter the number of colonies formed by $RAC1^{\Delta/\Delta}+RAC2^{-/-}$-cells, suggesting that they are insensitive to IODVA1. $RAC1^{\Delta/\Delta}+RAC2^{-/-}$-leukemic cells treated with vehicle or IODVA1 formed 2.4-times more colonies than wild-type cells treated with IODVA1. Combined with the biochemical data, these data support the idea that IODVA1 targets RAC activity in leukemic models and thus inhibits its downstream pro-survival signals.

Figure 4A:
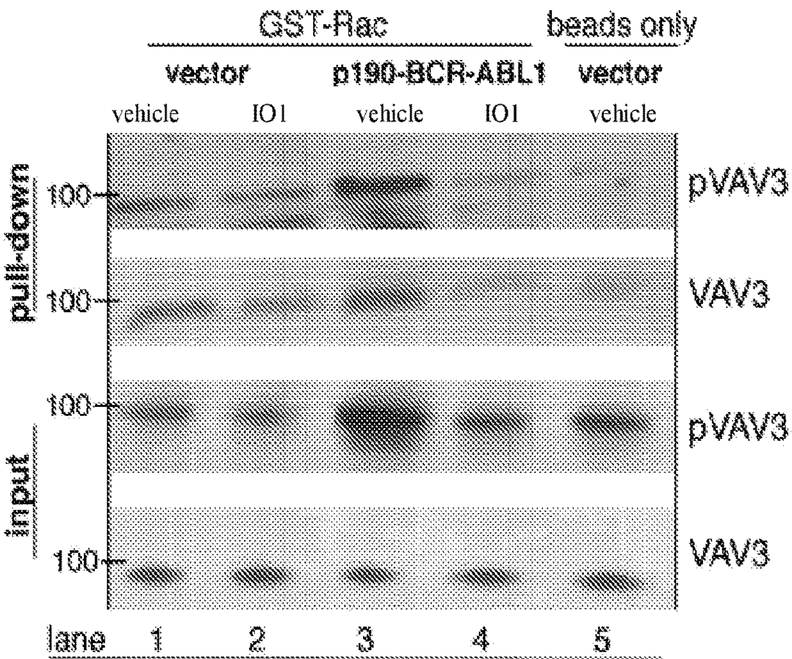
FIGS. 4A-4E depict data showing that IODVA1 targets VAV3 in vitro and in vivo. (4A) Results of GST-RAC pull-down from empty vector- and p190-BCR-ABL1-Ba/F3 cells treated with vehicle control or IODVA1 (IO1, 3 μM) for 30 min. Bead-bound protein complexes were washed, separated on SDS-PAGE, and immunoblotted for phospho- and total VAV3 and quantified. Input total (VAV3) and phospho (pVAV3) were used as reference. Quantification against total VAV3 is shown. Results are representative of at least two independent experiments. (4B) Binding affinity ($K_d$) between IODVA1 and VAV3 (green), LARG (brown), or RAC·GDP (blue). The microscale thermophoresis signal expressed as fractional occupancy was plotted against IODVA1 (0.1 nM-20 μM) and fitted to yield $K_d$. Results are shown as mean±SD of three independent experiments. (4C) Results of biotinylated-IODVA1 pull-down from PDX $Ph^+$ B-ALL 2018-136 and p190-BCR-ABL1-Ba/F3 cell lysates and from recombinant N-VAV3. Neutravidin bead-bound protein complexes were washed, separated on SDS-PAGE, and immunoblotted for VAV3 and quantified. Results are representative of at least two independent experiments. (4D) Quantification of the average number of colonies made by bone marrow wild-type and $Vav3^{-/-}$ p190-BCR-ABL1 leukemic cells treated with vehicle control or IODVA1 (IO1, 1 and 3 μM). Experiments were performed in triplicates. (4E) Bar graph summarizing representative cell cycle analysis experiment of wild-type and Vav3-p190-BCR-ABL1-bone marrow cells and treated with vehicle control or IODVA1 (IO1, 3 μM) for 20 h, performed in triplicates. n.s.—not significant, *p≤0.05; p≤0.01; **p≤0.0001 based on One-(4D) or Two-way (4E) ANOVA with Tukey's multiple comparisons test.
Figure 4A:
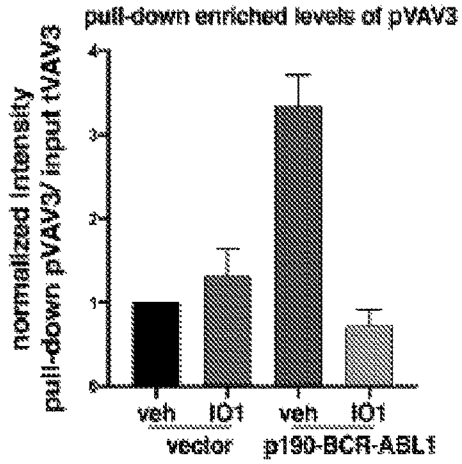
Figure 4A:
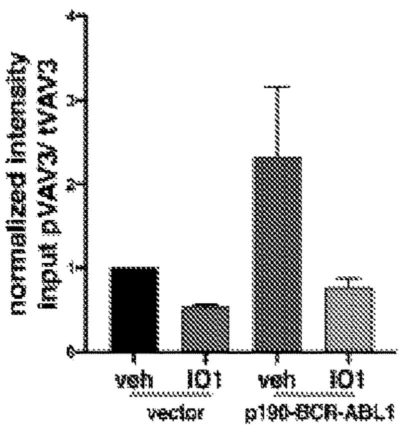

IODVA1 is an inhibitor of the RacGEF VAV3. RAC activity and signaling is regulated by GAPs, GDIs, and RacGEFs. Applicant hypothesized that the decrease in RAC activity might be caused by IODVA1 targeting one RAC regulator. Using biochemical assays, Applicant found that IODVA1 does not stimulate the activity of the RAC negative regulators p50GAP and RhoGDI1 (FIG. 10E-11G). Applicant next turned to positive regulators GEFs and posited that IODVA1 inhibits one RAC-specific GEF leading to its inactivation. While several RacGEFs have been associated with leukemogenesis [31-37], VAV3 was shown to play an important role in leukemogenesis[23]. Applicant thus focused on VAV3 and tested if IODVA1 inhibits VAV3 binding to RAC. Ba/F3 cells expressing either p190-BCR-ABL1 or empty vector were incubated with IODVA1 (3 μM) or vehicle control for 30 min and subjected to GST-RAC pull-down. The pull-down protein complex was separated on SDS-PAGE and immunoblotted for pVAV3 and VAV3 and quantified (FIG. 4A). There was no significant change in levels of VAV3 or pVAV3 bound to RAC in empty vector expressing Ba/F3 cells regardless of the treatment (FIG. 4A, lanes 1 & 2) suggesting that IODVA1 did not affect VAV3 activity or its ability to bind to RAC in cells not expressing the oncogene. Consistent with previous studies[23], expressing p190-BCR-ABL1 increased levels of pVAV3 by 3.2-fold in vehicle treated cells (FIG. 4A, input lane 3). The increased VAV3 activation resulted in stronger binding between pVAV3 and RAC (FIG. 4A, pull-down lane 3). IODVA1 treatment of cells expressing p190-BCR-ABL1 decreased levels of overall pVAV3 by 4-fold (FIG. 4A, input lane 4). This decrease is accompanied by a reduced binding of pVAV3/VAV3 to RAC (FIG. 4A, pull-down lane 4). Thus, the data suggests that IODVA1 inhibits overall VAV3 activation leading to a decreased binding to and activation of RAC in BCR-ABL1 expressing cells.

Figure 4B:
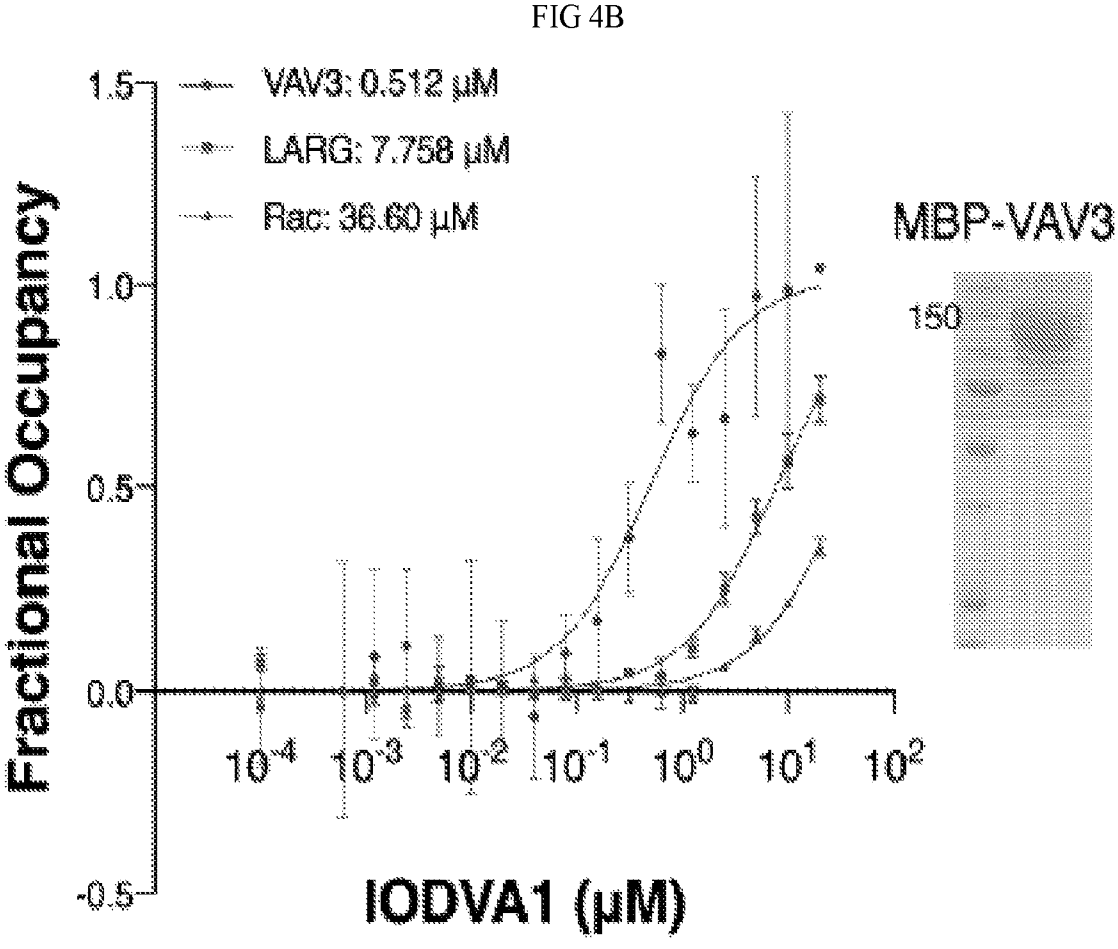

IODVA1 can inhibit VAV3-phosphorylation by inhibiting the activity of the SRC-like kinases responsible for VAV3 phosphorylation. However, this is unlikely as IODVA1 is not a kinase inhibitor[11]. Alternatively, IODVA1 binds to VAV3 and prevents its binding to SRC kinases. To test this hypothesis, Applicant measured its binding affinity ($K_d$) to recombinant VAV3 and RAC1 using microscale thermophoresis (MST); the catalytic domain (DH/PH) of the Leukemia Associated RhoGEF (LARG) served as negative control. Applicant used LARG for two reasons. First, if RHO-activation is not affected by IODVA1 (FIG. 4B), binding between LARG and IODVA1 should not be detected. Second, like VAV3, LARG contains a DH/PH domain responsible for the exchange activity such that any non-specific binding to this domain should be detected. The MST signal for VAV3 reaches saturation at 10 μM IODVA1 and beyond (FIG. 4B). The MST signal for RAC1 and LARG showed no saturation at the highest IODVA1 concentration tested. Fitting of the MST titration data shows that IODVA1 binds to VAV3 in a 1:1 molar ratio with a $K_d$ of 512 nM. The best estimate for the $K_d$ for RAC and LARG is 36.6 and 7.7 UM, respectively. Thus, IODVA1 binds tightly to VAV3.

Figure 4C:
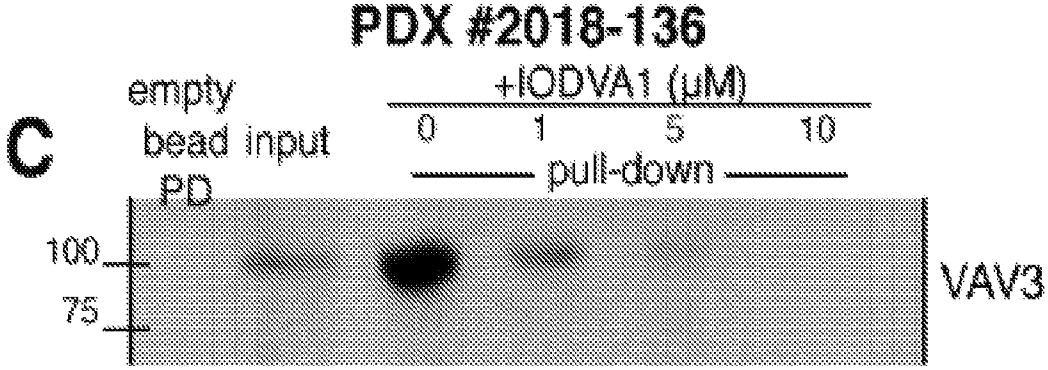
Figure 4C:
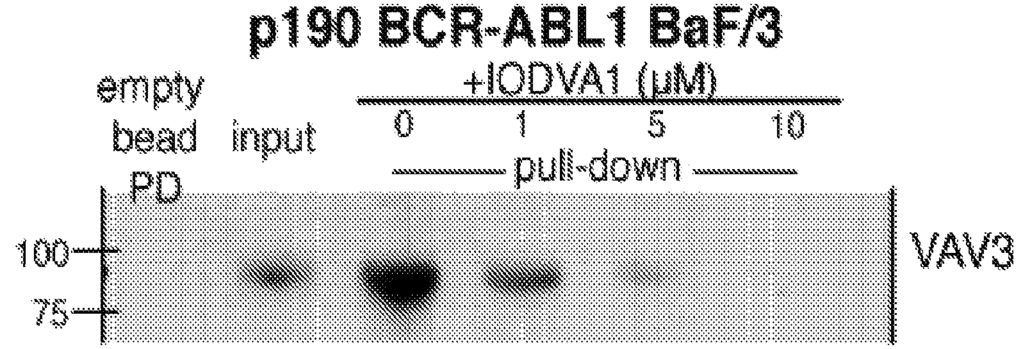
Figure 4C:
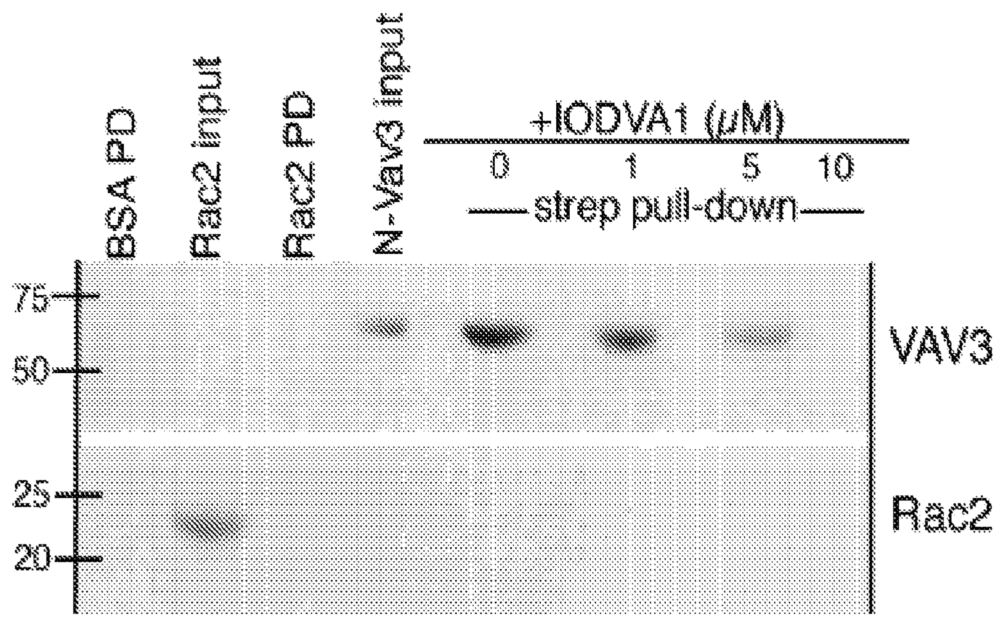

To further confirm that IODVA1 binds to VAV3, Applicant synthesized a biotinylated analog of IODVA1, incubated it with lysates from p190-BCR-ABL1-expressing Ba/F3 cells or cells from $Ph^+$ B-ALL patient 2018-136, and performed an avidin pull-down assay using NeutrAvidin beads. Cell lysates incubated with neutravidin beads alone served as background control. The bead-protein complexes were separated on SDS-PAGE and immunoblotted for VAV3 (FIG. 4C). Both cell lysates contained detectable levels of VAV3 that was concentrated 5 to 7 folds on biotinylated-IODVA1 while the empty beads did not bind any VAV3 (lanes 1-3). Free IODVA1 (1-10 μM) was able to compete VAV3 binding to the biotinylated immobilized IODVA1 in a dose-dependent manner (lanes 4-6). Next, the same experiment was repeated but with recombinant N-VAV3 lacking the C-terminus SRC-homology domains. Biotinylated IODVA1 but not empty beads pulled N-VAV3 and the addition of IODVA1 dissociated N-VAV3 from the conjugated beads (FIG. 4C). Together, these data further confirm that IODVA1 binds to VAV3 and that the C-terminus SH2/SH3 domains are not required for binding.

Figure 4D:
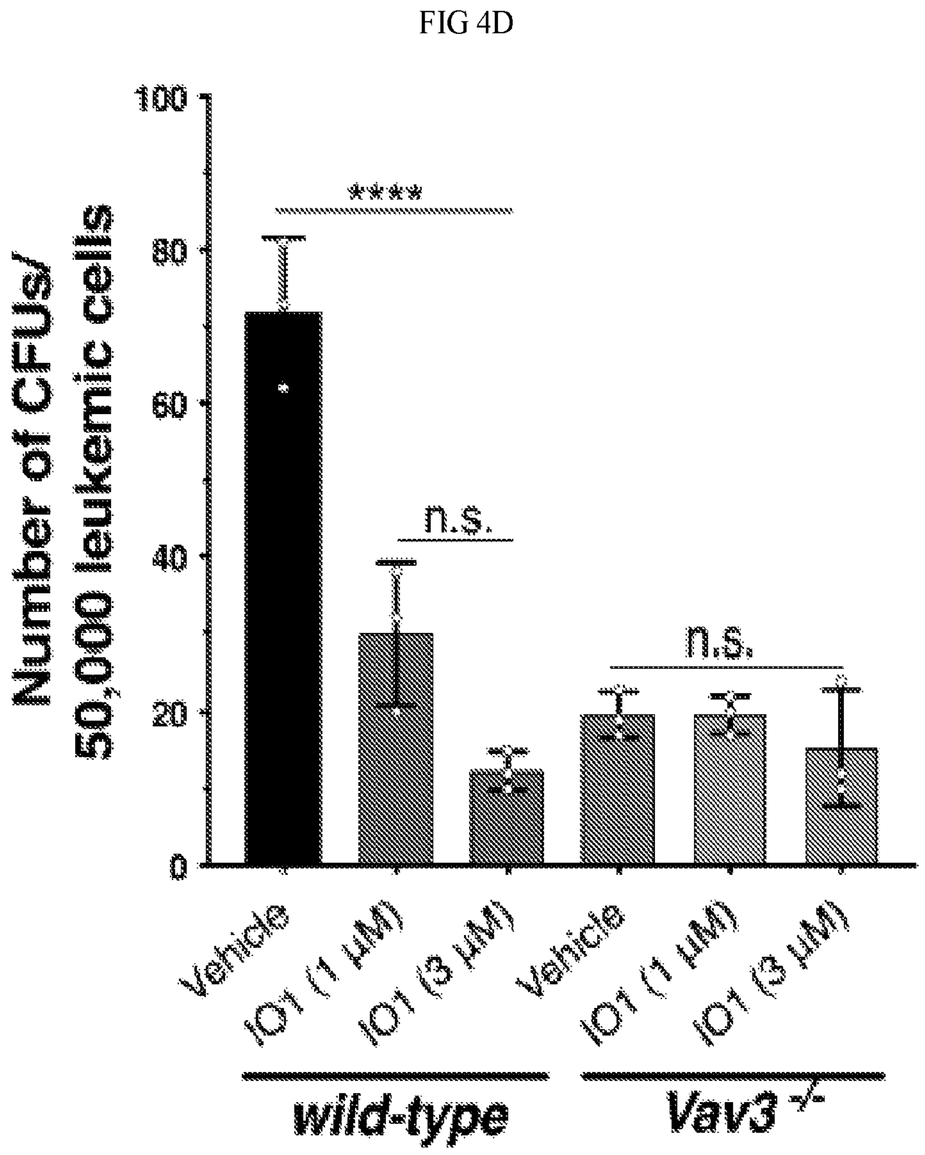
Figure 4E:
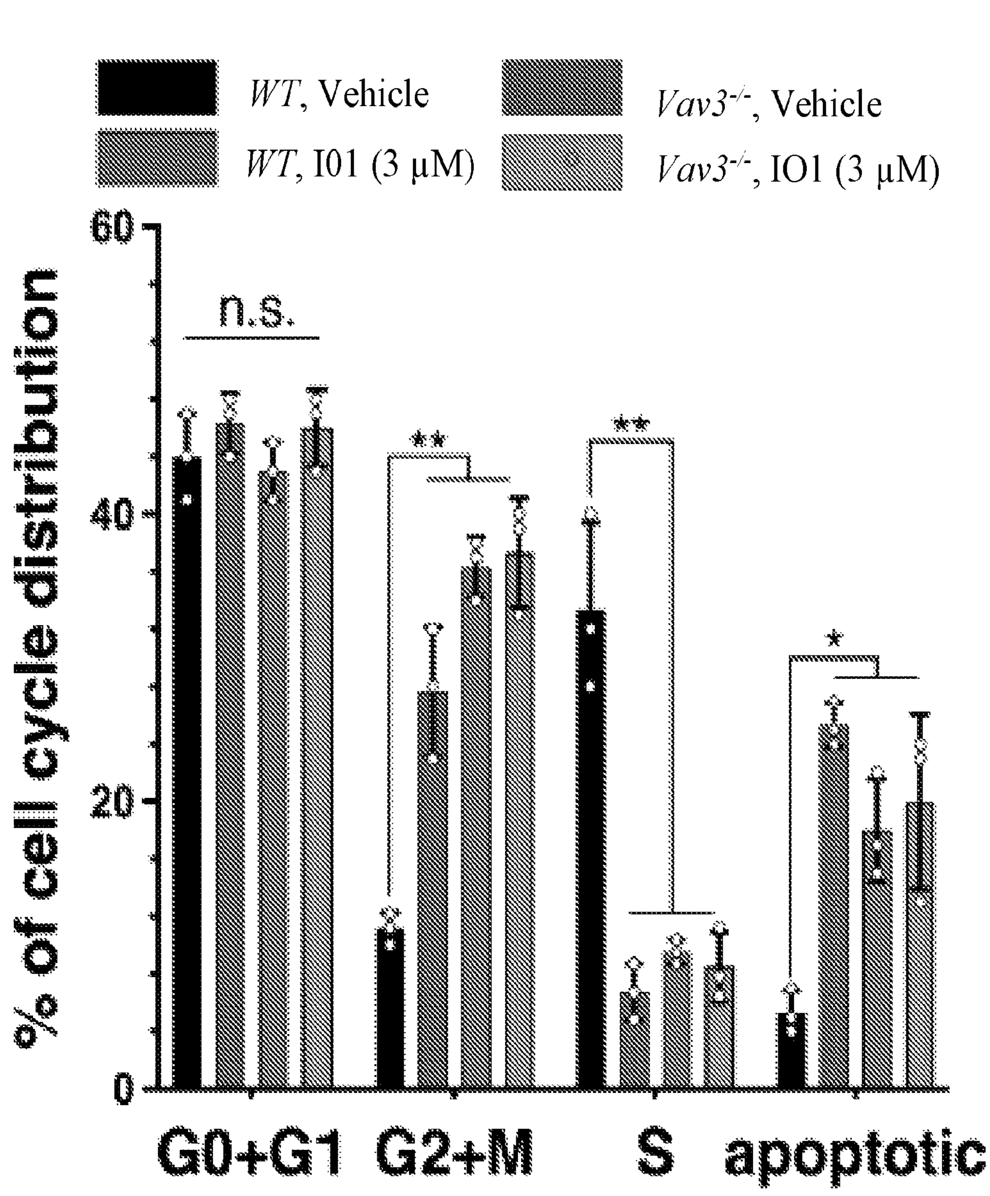

VAV3-deficient leukemic cells do not respond to IODVA1 in vitro and in vivo. To further validate VAV3 as target of IODVA1 and to test its specificity in a leukemic model, Applicant studied the effects of IODVA1 on leukemic cells from VAV3 knockout ($VAV3^{-/-}$) mice [4,23]. Applicant proposed that if IODVA1 targets VAV3, then VAV3-cells should be less sensitive to IODVA1. Wild-type or $VAV3^{-/-}$ murine BM leukemic cells expressing p190-BCR-ABL1 ($EGFP^+$/$B220^+$) were tested in colony formation assay in the presence of IODVA1 (FIG. 4D). The number of colonies formed by wild-type leukemic cells expressing VAV3 (mean±SD of 72±9.5) decreased on average by 2.4- and 7-fold in the presence of 1 and 3 μM IODVA1 (30±9.2 and 12±2.5), respectively. $VAV3^{-/-}$ leukemic BM cells on the other hand formed similar number of colonies when grown in the presence of vehicle control (20±3.1) or IODVA1 (20±2.5 and 15±7.5) suggesting they lost sensitivity to the drug. Applicant did not observe significant difference in the number of colonies formed by $VAV3^{-/-}$ leukemic cells and by IODVA1-treated wild-type leukemic cells. Similarly, cell cycle analysis shows that $VAV3^{-/-}$ cells expressing p190-BCR-ABL1 were not affected by IODVA1 (FIG. 4E). Taken together, the data suggest specificity of IODVA1 to VAV3 as wild-type leukemic cells respond to IODVA1 while VAV3-leukemic cells are unresponsive and mimic IODVA1-treated wild-type VAV3 leukemic cells.

Figure 5A:
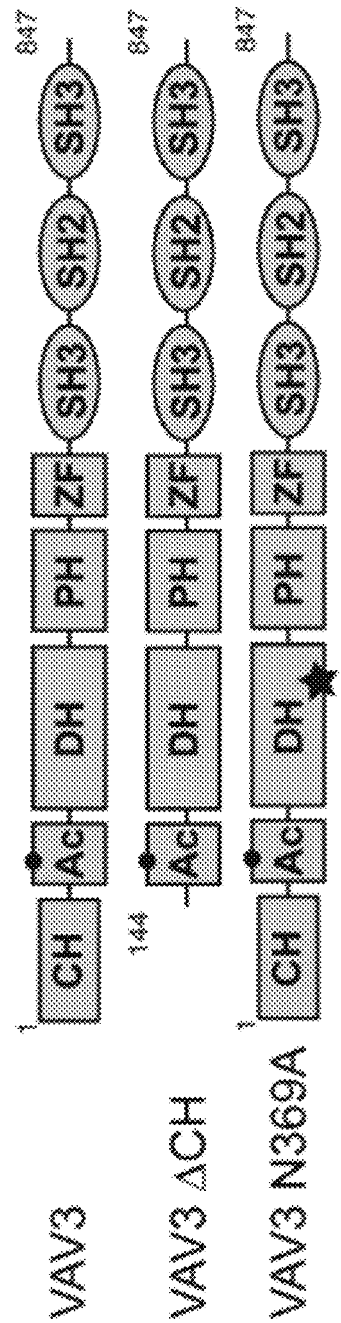
FIGS. 5A, 5B and 5C depict data showing that: Expression of transgenic VAV3 re-sensitizes Vav3-deficient cells to IODVA1.
Figure 5B:
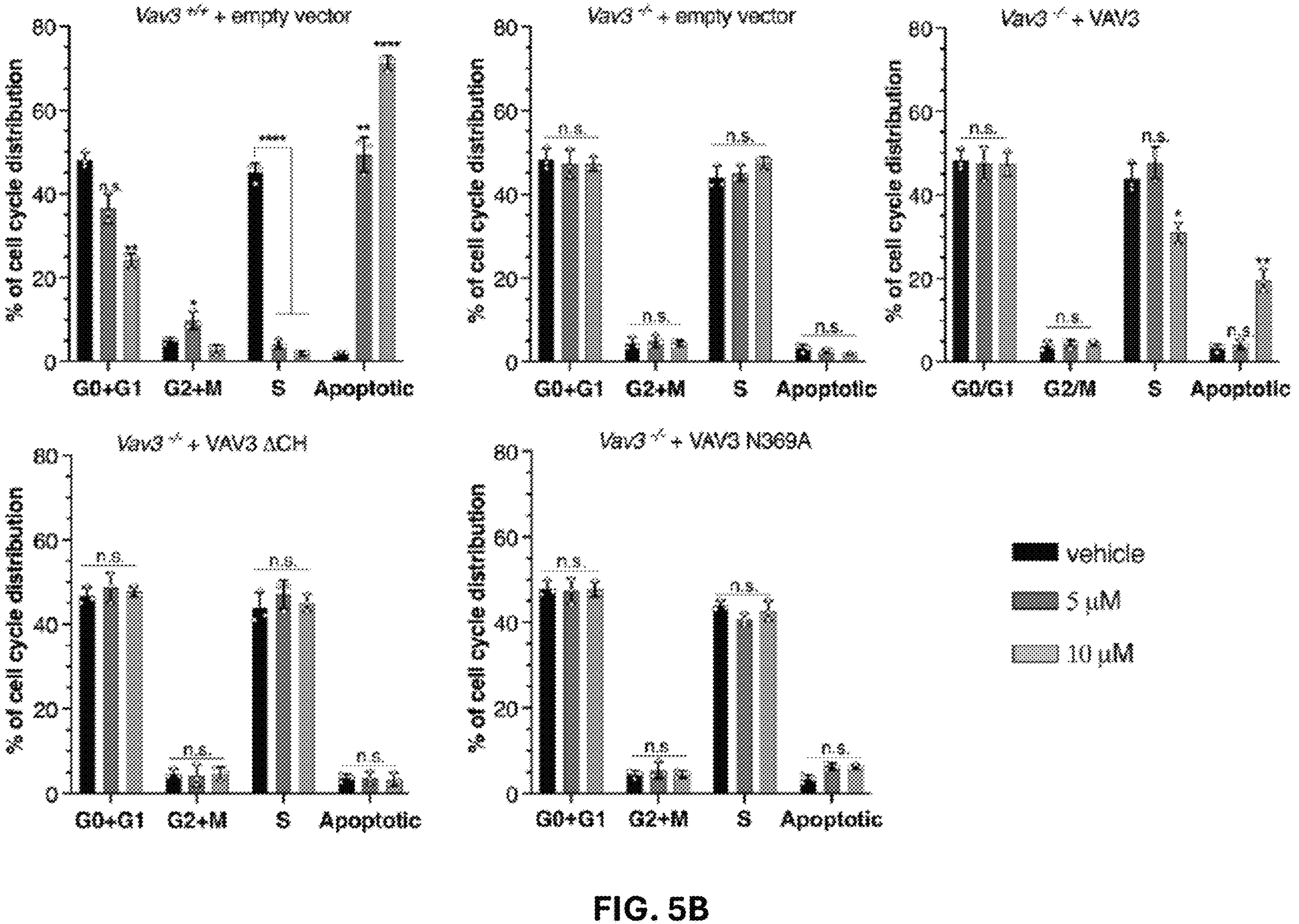

Next, it was reasoneded that if IODVA1 targets VAV3, rescuing $VAV3^{-/-}$ leukemic cells by expressing exogenous VAV3 should re-sensitize those cells to IODVA1. Applicant expressed full-length VAV3, the dominant active ΔCH-mutant or the N369A exchange deficient mutant[38] (FIG. 5A) in $VAV3^{-/-}$ p190-BCR-ABL1-transformed murine bone marrow leukemic cells and analyzed changes in cell cycle 18 h post-treatment with vehicle control or IODVA1 (FIG. 5B). Introducing full-length VAV3 but not the empty vector re-sensitized the $VAV3^{-/-}$ BM leukemic cells to IODVA1 as shown by a 5.8-fold increase in apoptosis (p=0.008) and a 15% decrease (p=0.02) in cells in the S-phase at 10 μM. Expressing the ΔCH-mutant or the GEF-activity deficient mutant did not re-sensitize $VAV3^{-/-}$ leukemic cells to IODVA1 even at the highest concentration while the GEF-deficient N369A mutant had no effect.

Figure 5C:
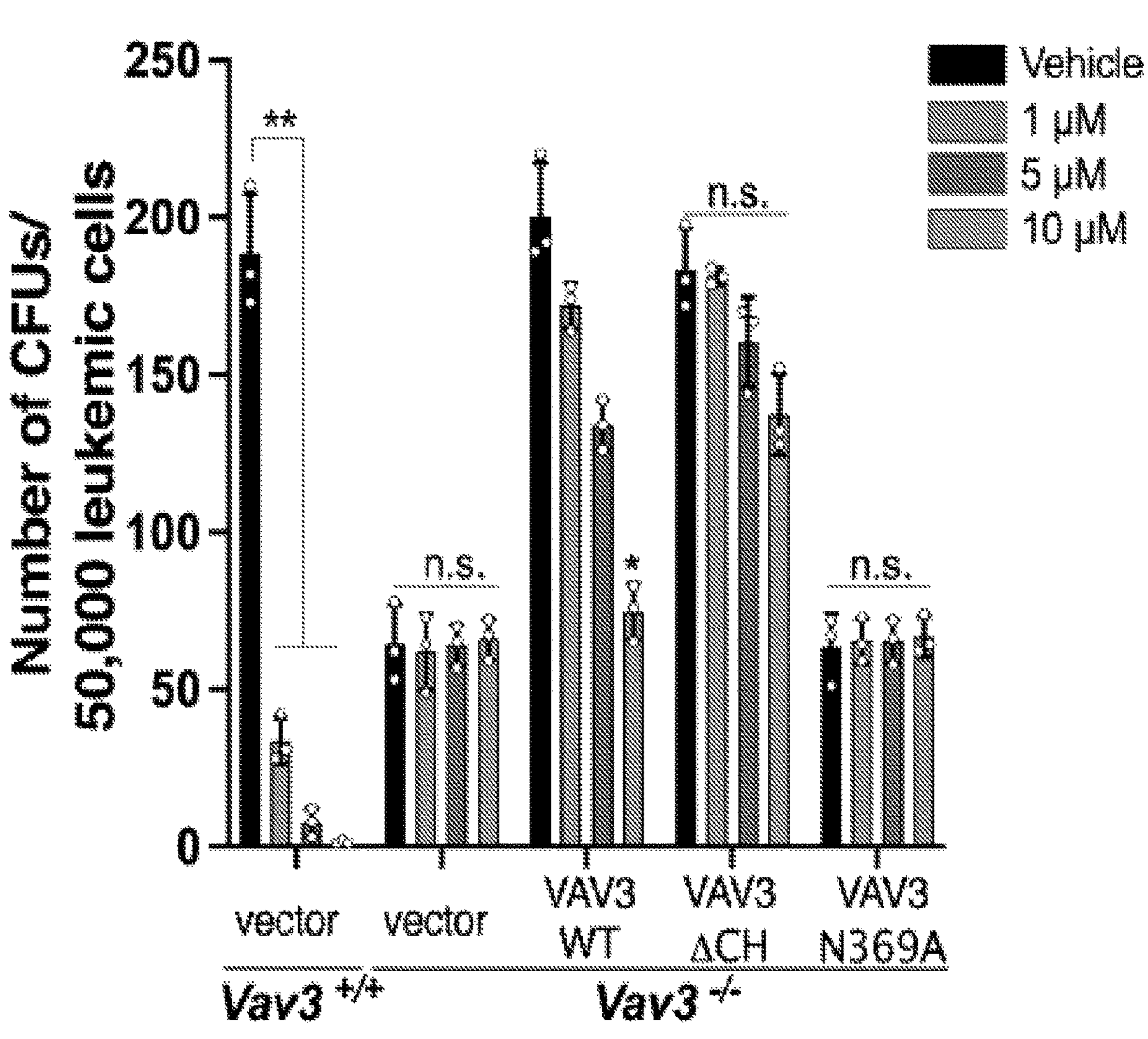

To test if the results of the previous rescue experiments hold in proliferation assays, Applicant subjected the VAV3 full-length and ΔCH- and GEF-deficient mutant expressing $VAV3^{-/-}$ leukemic cells to colony formation assays in the presence of IODVA1 (1, 5, and 10 μM) or vehicle control (FIG. 5C). Re-introducing full-length or ΔCH VAV3 results in similar number of colonies as with wild-type BM leukemic cells (black bars, mean of 200.3 and 183.3 vs 188.3, respectively), a 3-fold increase from $VAV3^{-/-}$ leukemic cells expressing the empty vector (mean=64.3 colonies). Re-introducing the GEF-deficient mutant has no effect on the colony formation ability of $VAV3^{-/-}$ leukemic cells (mean=63.3 colonies). Importantly, $VAV3^{-/-}$ leukemic cells expressing VAV3 respond to IODVA1 in a dose dependent manner. At 10 μM IODVA1, the number of colonies made by $VAV3^{-/-}$ cells expressing full-length VAV3 is reduced by a third and becomes similar to that made by $VAV3^{-/-}$ expressing empty vector (gray bars, 75 vs 66 colonies). Interestingly, ΔCH expressing leukemic cells are less sensitive to IODVA1 while the GEF-deficient mutant leukemic cells were insensitive to IODVA1 even at the highest concentration. Taken together, the cell cycle and proliferation experiments show that exogenous expression of VAV3 in $VAV3^{-/-}$ leukemic cells increases their dependency on VAV3 GEF-dependent proliferative pathways and re-sensitizes them to IODVA1. The reduced sensitivity of the ΔCH mutant to IODVA1 suggests that this domain is part of its binding site on VAV3.

Figure 11A:
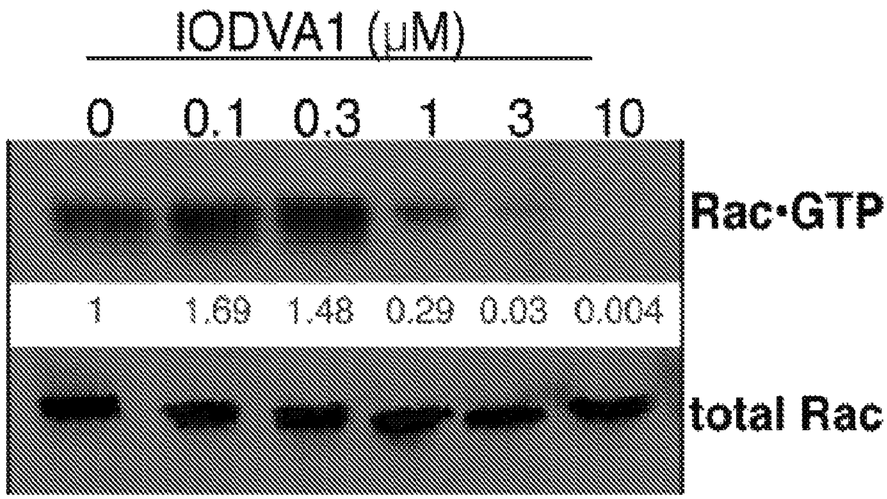
Figure 11D:
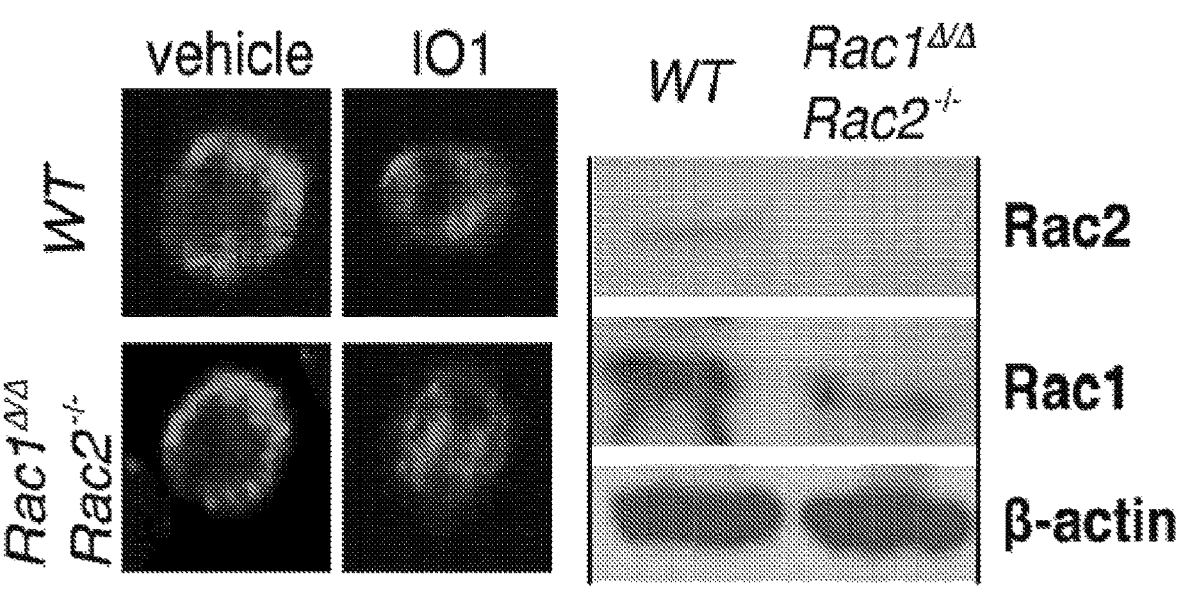
Figure 11E:
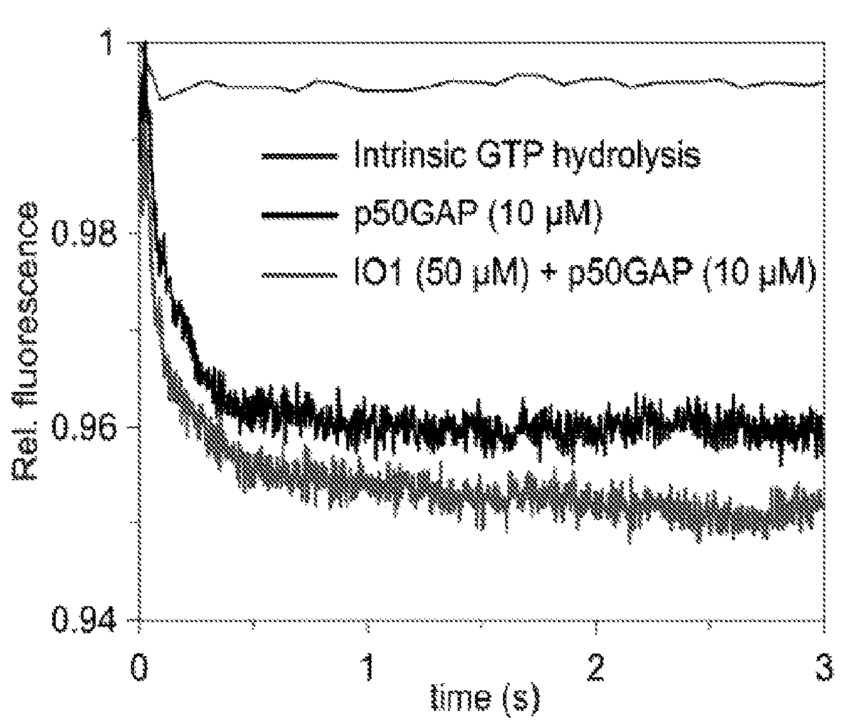
Figure 11F:
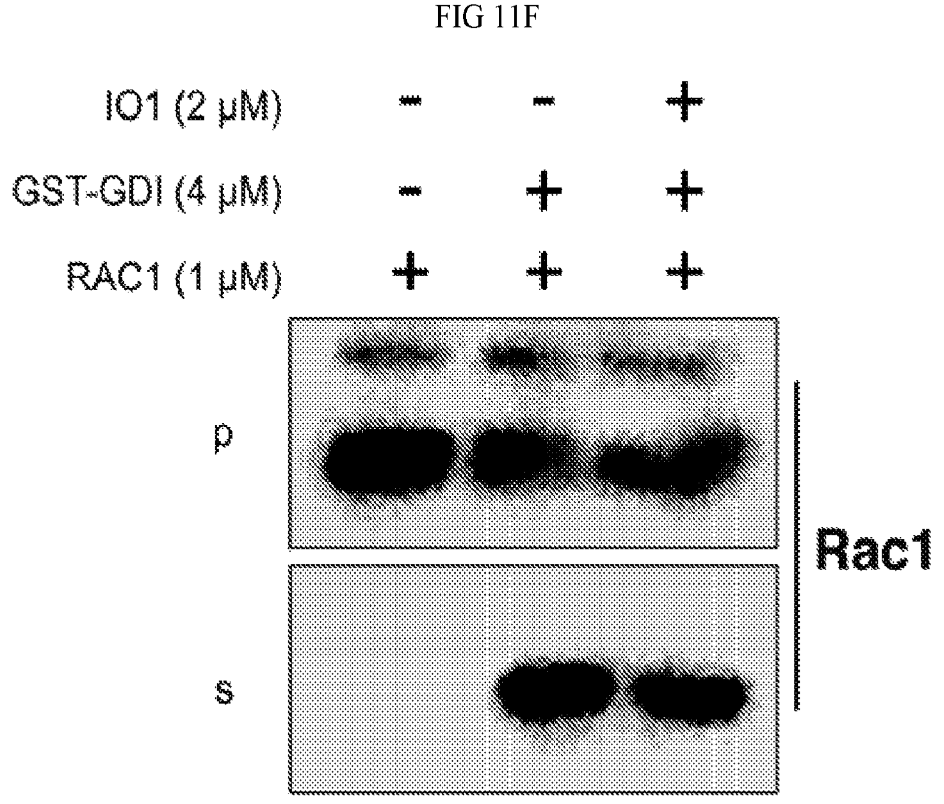
Figure 11G:
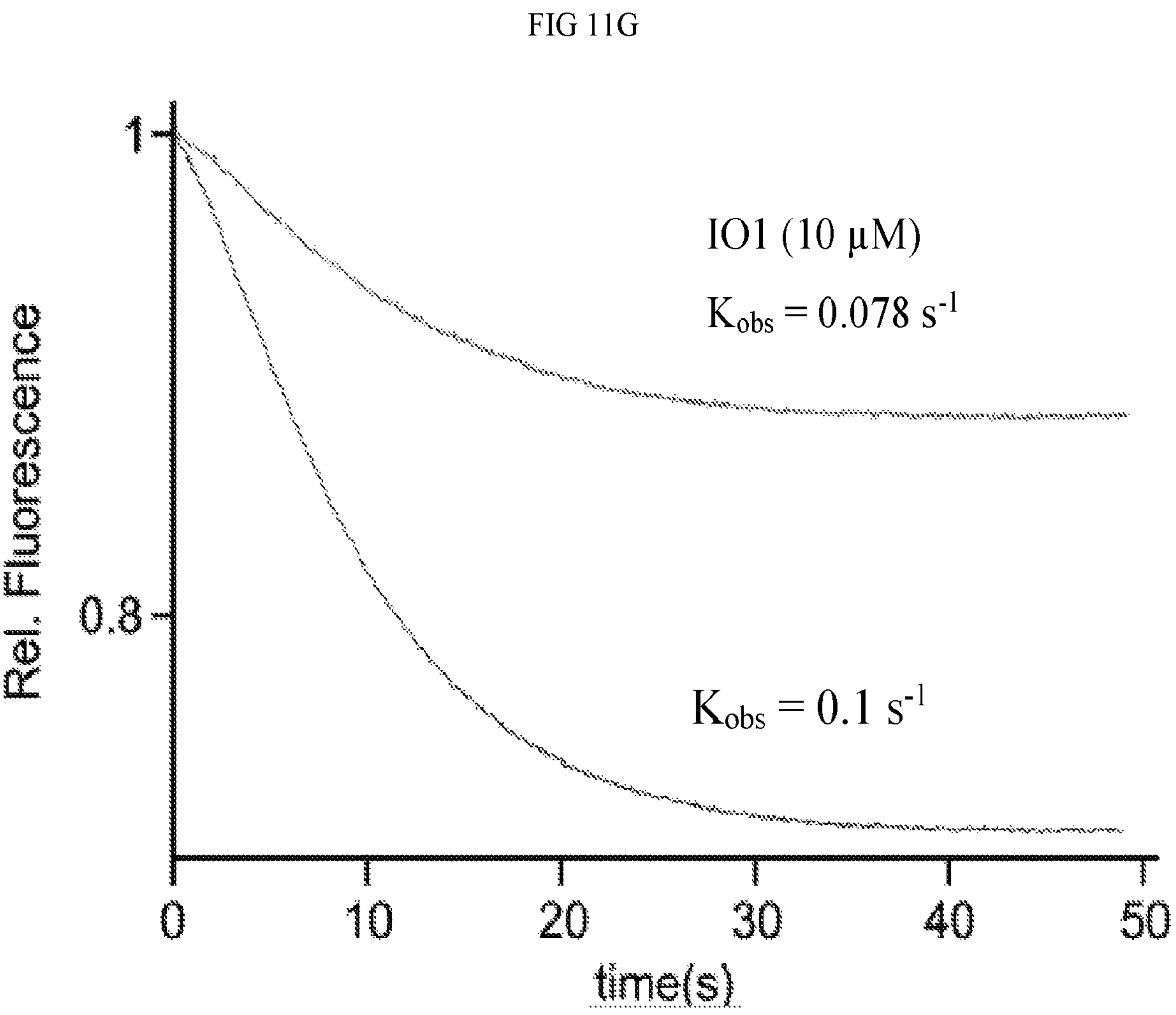

Next, Applicant determined if the lack of response to IODVA1 by $VAV3^{-/-}$ cells holds in vivo. Applicant transplanted wild-type or $VAV3^{-/-}$ LDBM cells transduced with p190-BCR-ABL1 into lethally irradiated C57BL/6 mice, waited for the leukemia to develop, and treated the mice with either vehicle control or IODVA1 administered through mini-osmotic pumps as before. $VAV3^{-/-}$ leukemic mice did not respond to IODVA1 supporting the hypothesis that VAV3 is IODVA1's target in vivo (FIG. 11A). Taken together, the data show that VAV3-deficient leukemia progenitor cells do not respond to IODVA1 in cellular and in vivo assays while re-introducing VAV3 re-sensitize them to IODVA1. The weaker response of the VAV3 ΔCH mutant to IODVA1 suggests that the calponin homology domain regulates IODVA1's activity. Applicant's data are consistent with the idea that VAV3 is IODVA1's target in vivo and in vitro. The persistence of leukemia in vivo in $VAV3^{-/-}$ chimeras suggests that $VAV3^{-/-}$ BCR-ABL1 leukemia has evolved mechanisms of escape relying on RAC-independent pathways such as AKT and STAT3 signaling pathways (FIG. 11B-11C).

Figure 7A:
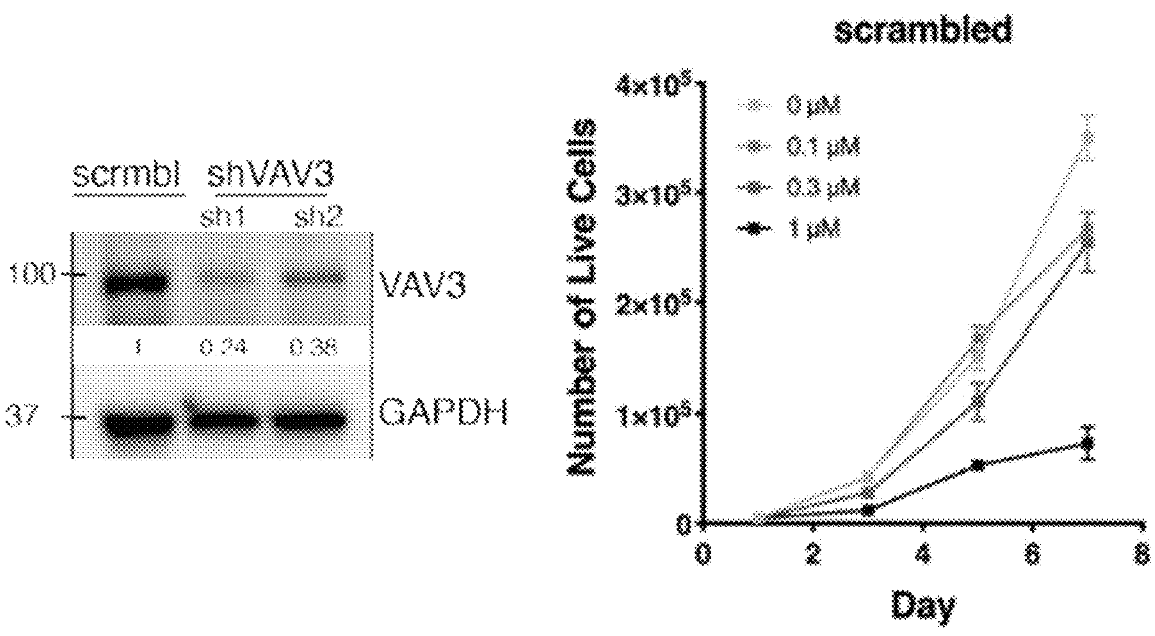
FIGS. 7A-7C depict data showing that IODVA1 decreases levels of pVAV3 in in vitro and in vivo models of triple negative breast cancer. (7A) Immunoblot—efficiency of shRNA-mediated VAV3 knockdown in MDA-MB-231 triple negative breast cancer. Graphs—summary of trypan blue exclusion viability assay on knockdown cell lines in the presence of IODVA1 (0-1 μM) at the indicated timepoints. (7B) Levels of phosphorylated VAV3 (pY173) in MDA-MB-231 cells were assessed by immunoblotting post-15 min incubation with IODVA1 (3 μM). (7C) Immunohistochemical staining of phosphorylated VAV3 in tissue derived from MDA-MB-231 xenografts treated with vehicle control or IODVA1.
Figure 7A:
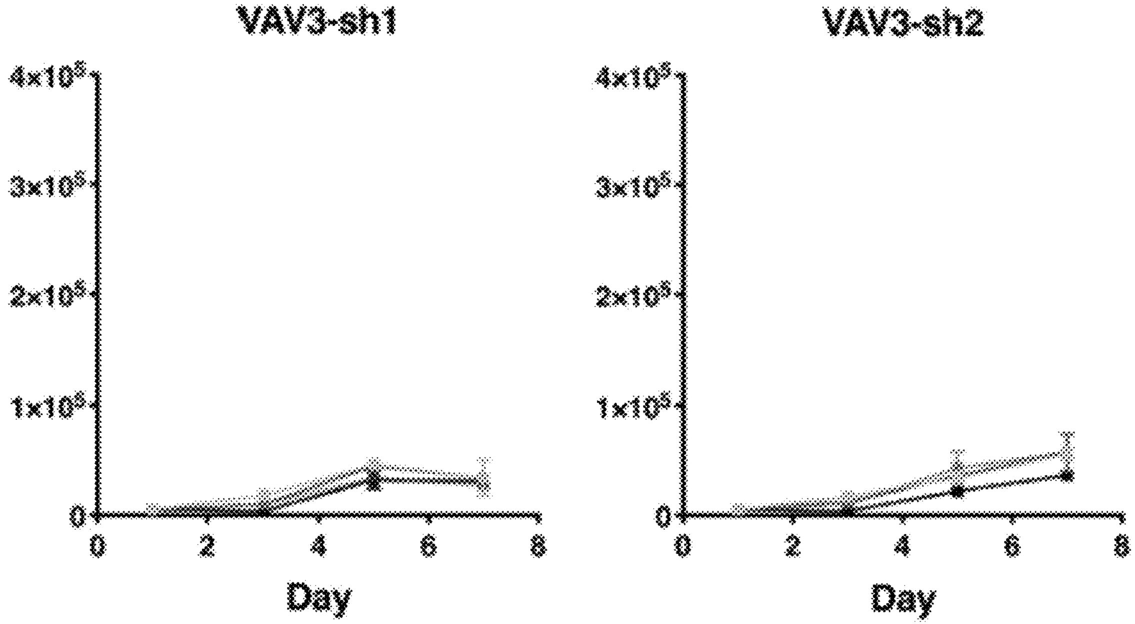
Figure 7B:
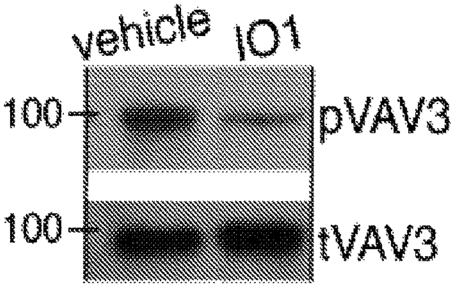

IODVA1 targets VAV3 in MDA-MB-231 cells and xenograft tumors. Next, Applicant tested if IODVA1 is effective in a non-leukemia solid tumor model of VAV3-dependent cancer. Applicant chose MDA-MB-231 triple negative breast cancer cells because these cells express high endogenous levels of VAV3[39] and because VAV3 is an acknowledged target in breast cancer[39-43]. In addition, Applicant has shown that these cells are sensitive to IODVA1 and that IODVA1 decreases RAC activity and halts tumor growth and induces apoptosis in MDA-MB-231 xenograft mice[11]. First, Applicant found that reduction in VAV3 expression levels by targeting shRNA severely reduces proliferation of MDA-MB-231 cells. IODVA1 (0.1-1 μM) reduces, in a dose-dependent manner, the viability and proliferation of scrambled MDA-MB-231 but has no effect on the shVAV3 expressing cells (FIG. 7A). Second, Applicant incubated MDA-MB-231 cells with IODVA1 (3 μM) for 15 min and analyzed the levels of phosphorylated VAV3 (pY173) by immunoblotting. IODVA1 treatment results in a significant decrease in pY173 signal (FIG. 7B). Since phosphorylation of Tyr173 is indicative of VAV3 activation, it is concluded that IODVA1 inhibits VAV3 activity shortly after exposure.

Figure 7C:
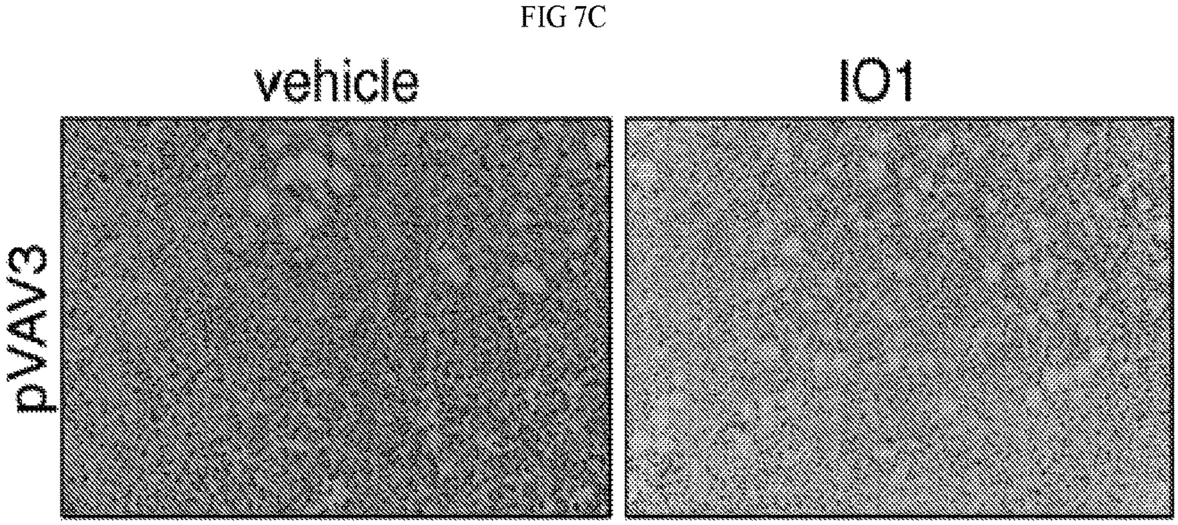

To test if IODVA1 inhibits VAV3 in vivo, MDA-MB-231 xenograft tumors generated [11] were stained by immunohistochemistry for pVAV3. Comparison of pVAV3 stained tumor sections treated with vehicle control and with IODVA1 shows significant decrease in pVAV3 staining for tumors treated with IODVA1 than with vehicle control (FIG. 7C). Thus, IODVA1 also inhibits VAV3 in vitro and in vivo in solid tumor models and in cell-independent manner.

Figure 6B:
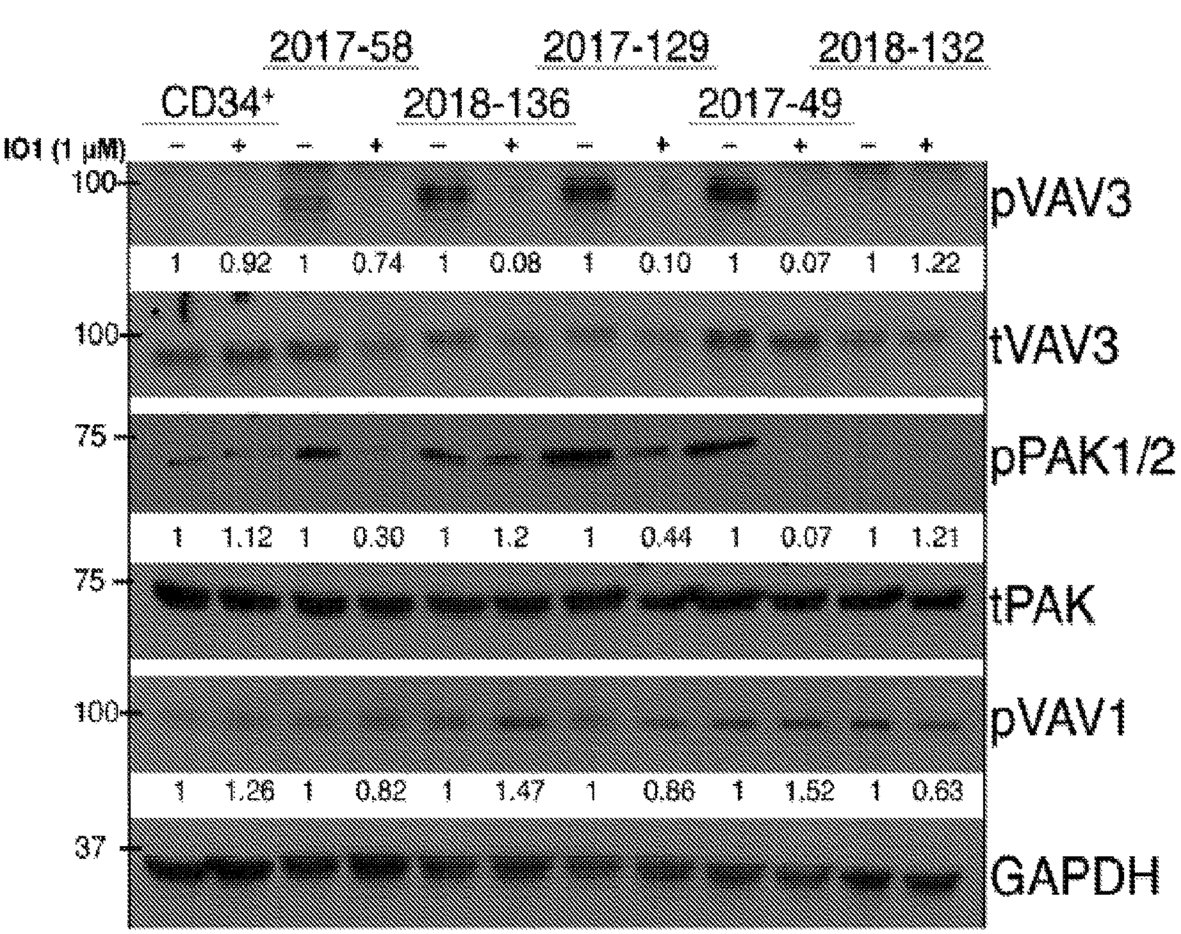

IODVA1 decreases survival of patient-derived leukemia cells in vitro and in vivo. Consistent with Applicant's findings with peripheral human blood $CD34^+$ BCR-ABL1 cells (FIG. 1A-1B), cells from PDX models representing pediatric $Ph^+$, Ph-like, and MLL-rearranged B-ALL patients including patients with TKI-resistant BCR-ABL (T315I) mutation (Table 1) were found in general to be highly sensitive to IODVA1 ex vivo (FIG. 10A-10C). To test if responses of PDX cells to IODVA1 correlate with VAV3 status, Applicant incubated IODVA1-sensitive $Ph^+$ PDX 2018-136 and 2017-129 cells and Ph-like PDX 2017-49 cells and less sensitive $Ph^+$ PDX 2017-58 cells, Ph-like PDX 2018-132 cells with IODVA1 (1 μM) or vehicle control for 30 min and measured levels of pVAV3 (pTyr173), pPAK1 (pThr423), and pVAV1 (pTyr174) by immunoblotting. Human cord blood $CD34^+$ cells were used as negative control as they were not sensitive to IODVA1 and do not have high levels of pVAV3. Levels of pVAV3 were high in vehicle treated PDX sensitive cells and decreased by 90% following IODVA1 treatment (FIG. 6B). In general, pPAK1 followed the same trend. Levels of pVAV3 and pPAK1 were not detectable in weakly responsive $Ph^+$ PDX cells 2017-58 and Ph-like 2018-132 cells regardless of the treatment. pVAV1 levels on the other hand were unchanged by IODVA1 in any of the patient samples tested.

TABLE 1

List of ALL patients with samples available through the Pediatric Leukemia Avatar Program at CCHMC, including those with cytokine receptor, tyrosine kinase (TK), or Ras pathway mutations. Clinical history of TKI treatment is indicated with the TKI received. All samples have confirmed patient-derived xenografts (PDXs) with disease latency as noted. Shown samples indicate those selected for Ph+/Ph-like cohort. Patient samples that have established in vitro culture are marked (*). Next-Gen Sequencing (NGS) was performed using the FoundationOne Heme Panel (Cambridge, MA). Other abbreviations: relapsed or refractory (R/R), busulfan (BU), Philadelphia chromosome ($Ph^+$), Philadelphia-like (Ph-like), minimal residual disease (MRD), bone marrow transplant (BMT).

PDX ALL models

| Patient # | Sample ID | Disease Stage | Mutations/Group | TKI History |
|---|---|---|---|---|
| ALL-09 | 2016-116* | R/R | T(1; 11), t(6; 6) | — |
| ALL-011 | 2016-79 | De Novo | Ph-like (IGH-CRLF2; JAK2) | Ruxolitinib |
| ALL-012 | 2016-88 | De Novo | Ph-like (CNTRL-FGFR1) | — |
| ALL-014 | 2017-49 | De Novo | Ph-like (P2RY8-CLRF2; ETV6-NTRK3) | Larotrectinib |
| ALL-015 | 2017-58* | De Novo | Ph+ (BCR-ABL1); Ph-like (P2RY8-CRLF2) | Dasatinib |
| ALL-017 | 2017-129* | R/R | Ph+ (BCR-ABL1, T315I) | Ponatinib |
| ALL-019 | 2018-132 | De Novo | Ph-like (IGH-CRLF2; JAK2) | — |
| ALL-004 | 2018-136 | De Novo | Ph+ (BCR-ABL1) | — |
| ALL-032 | 2018-190 | R/R | B-ALL (MLL/AF9) | — |
| ALL-011 | 2016-70 | De Novo | Ph-like (NUP214/ABL1, IKZF-1, P2RY8/CD99, SETD2, VHL) | — |

Figure 2C:
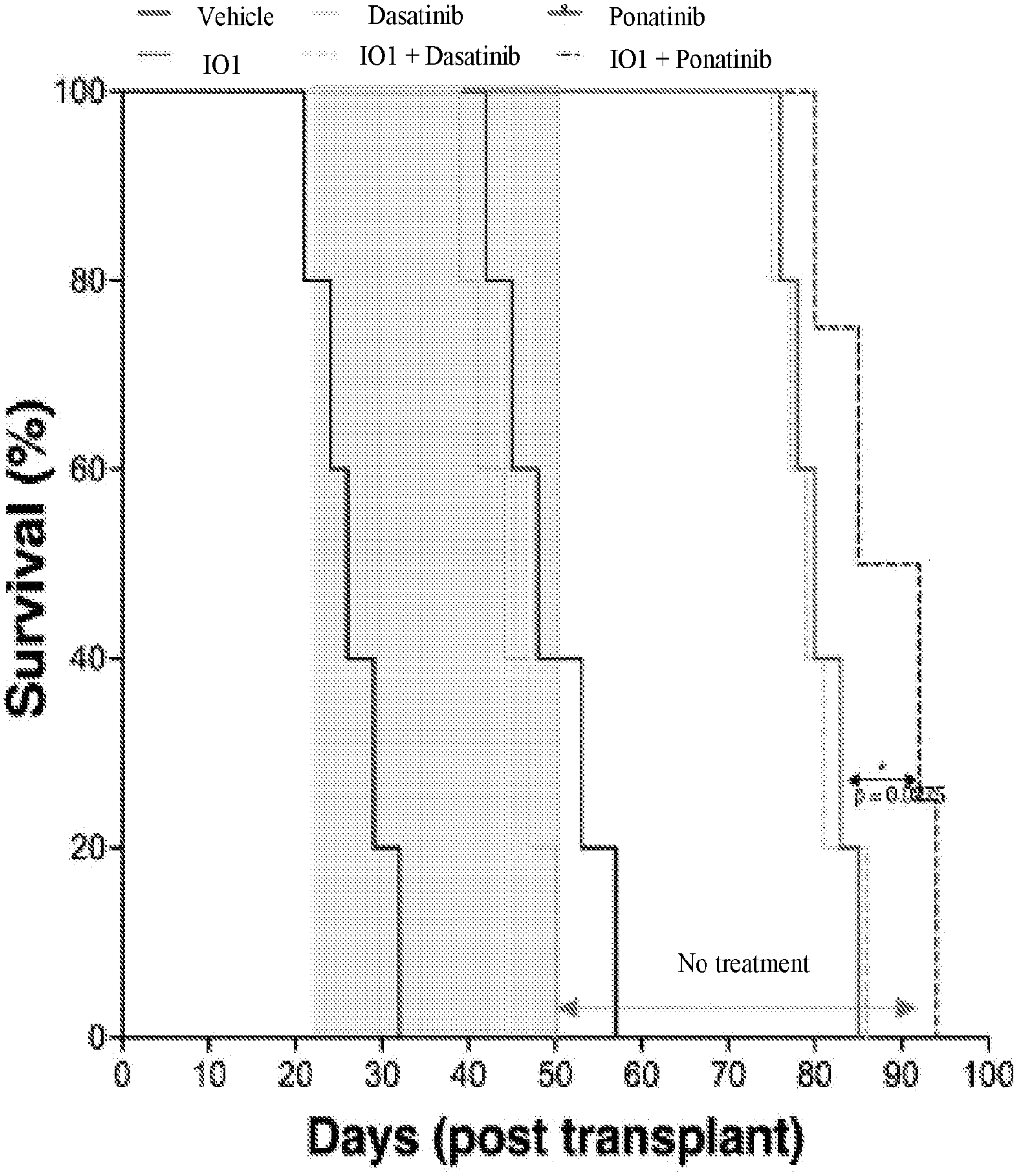
Figure 2D:
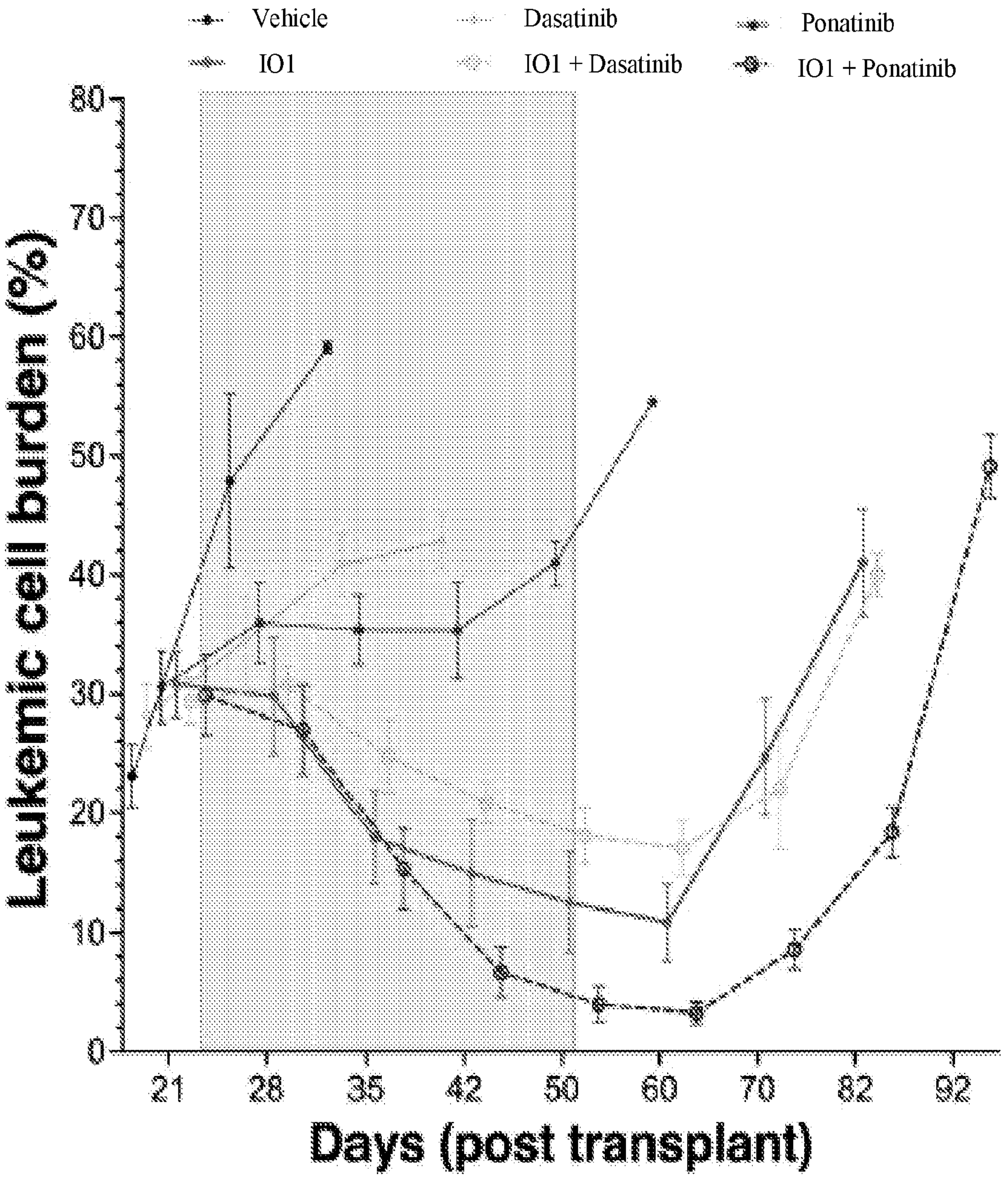

To validate ex vivo survival results in vivo, Applicant transplanted cells from patient 2018-136 with $Ph^+$ (BCR-ABL1), IKZF1, ΔCDKN2A/B, and ΔPAX5 into NOD/SCID/IL2λ-receptor null (NSG) mice and waited 21 days for the leukemia to develop. Mice were stratified into 6 groups (5 mice per group) and administered either PBS vehicle control, IODVA1 (4 mM), dasatinib or ponatinib (0.5 mM), and the combinations IODVA1+dasatinib or IODVA1+ponatinib in subcutaneous osmotic pumps for 4 weeks after which treatment was stopped. Kaplan-Meier survival plots show that all control group mice died at day 32, or 10 days post administration of the vehicle control (FIG. 2C, black line). The dasatinib- and ponatinib-treated mice died by day 50 and 57, or 28 and 35 days after treatment began, respectively. Mice treated with IODVA1 survived until day 85, or 35 days post treatment withdrawal. There was no difference in survival between IODVA1 or IODVA1+dasatinibtreated mice. The IODVA1+ponatinib treated mice survived till day 94 or 44 days post treatment withdrawal. Statistical analysis shows that the later treatment combination is superior to IODVA1 alone (p=0.0275). Counts of $CD19^+/CD45^+$ leukemic progenitor cells from the 2018-136 leukemic mice peripheral blood indicated that the IODVA1 monotherapy significantly decreased leukemic progenitor levels from 30.8±2.8% at the beginning of the treatment (day 22) to 12.5±4.2% at the end of the treatment (day 50, FIG. 2D) better than dasatinib or ponatinib. This level was unchanged at day 60 but steadily increased after that to reach 41±4.5% at day 82. The IODVA1+ponatinib combination therapy was the most efficient at decreasing the leukemic progenitor levels to 4.0±1.5% at the end of the treatment (day 50). This level kept decreasing to 3.3±1%

10-days post treatment arrest (day 60) but steadily increased albeit at a lower rate to reach 49.1±2.6% at day 92.

Figure 12A:
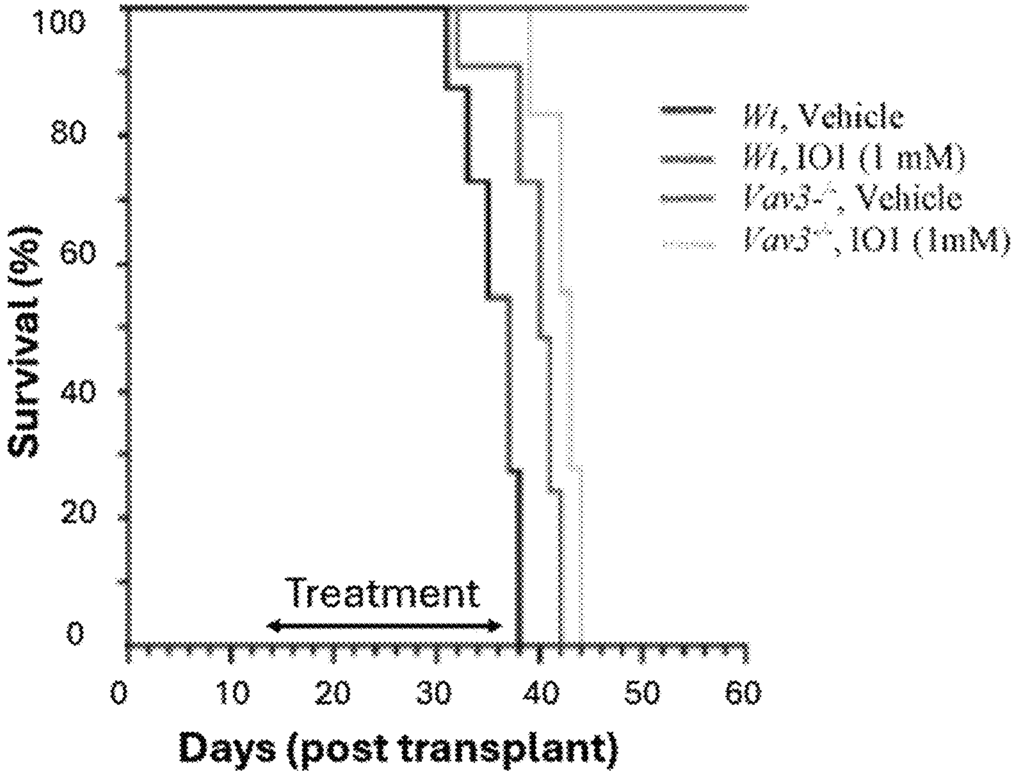
FIGS. 12A-12G depict data showing that VAV3-deficient leukemia is not responsive to IODVA1. (12A) Kaplan-Meier plot showing survival of wild-type or Vav34-p190-BCR-ABL1 leukemic mice post-treatment with osmotic pumps implanted subcutaneously and carrying vehicle control or IODVA1 (IO1, 1 mM). N=5 mice per treatment group. (12B) Count (% leukemic progenitors in peripheral blood) of residual leukemic ($EGFP^+$-BCR-ABL1) cells at week 1 and 2 post-treatment for mice from (12A). (12C) Bar graph of pharmacodynamic assessment of leukemic progenitor cells (%) from wild-type or $Vav3^{-/-}$ mice with p190-BCR-ABL1 leukemia and treated with vehicle control (black and light grey) or IODVA1 (IO1) following 2-week treatment using phospho-flow analysis of the indicated effectors. (12D) Bar graph summarizing results of the phospho-flow cytometric analysis of the indicated signaling molecules in the leukemic progenitor bone marrow aspirates of wild-type or $Vav3^{-/-}$ mice treated with IODVA1. (12E) IODVA1-dependent survival curves of empty vector-(black lines), wild type full length VAV3- or ΔCH-mutant of VAV3-expressing Ba/F3 cells in the empty vector- or p190-BCR-ABL1-transduced background. (12F) Results of biotinylated-IODVA1 pull-down from PDX $Ph^+$ B-ALL 2018-136 and p190-BCR-ABL1-Ba/F3 cell lysates. Neutravidin bead-bound protein complexes were washed, separated on SDS-PAGE, and immunoblotted for PREX1, VAV3, and VAV1. Results are representative of at least two independent experiments. (12G) pVAV3 levels in the bone marrow aspirates of PDX 2018-136 engrafted mice treated with vehicle control or dasatinib at the time of sacrifice or IODVA1 (IO1) at the end of treatment. Representative blot of two experiments, n=3 mice per group. $*p \le 0.05$; $p \le 0.01$, $*p \le 0.001$, $****p < 0.0001$ using One-way ANOVA with Tukey's multiple comparison test.
Figure 12B:
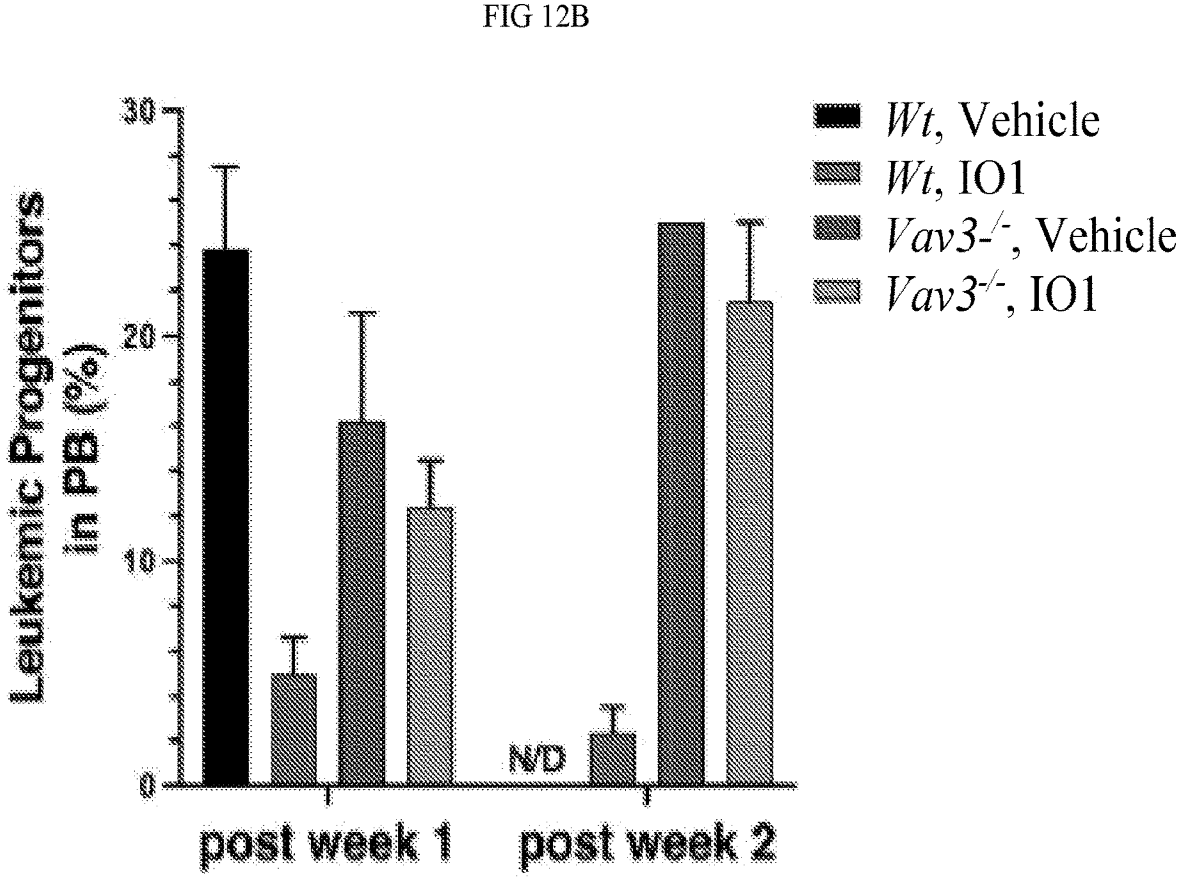
Figure 12C:
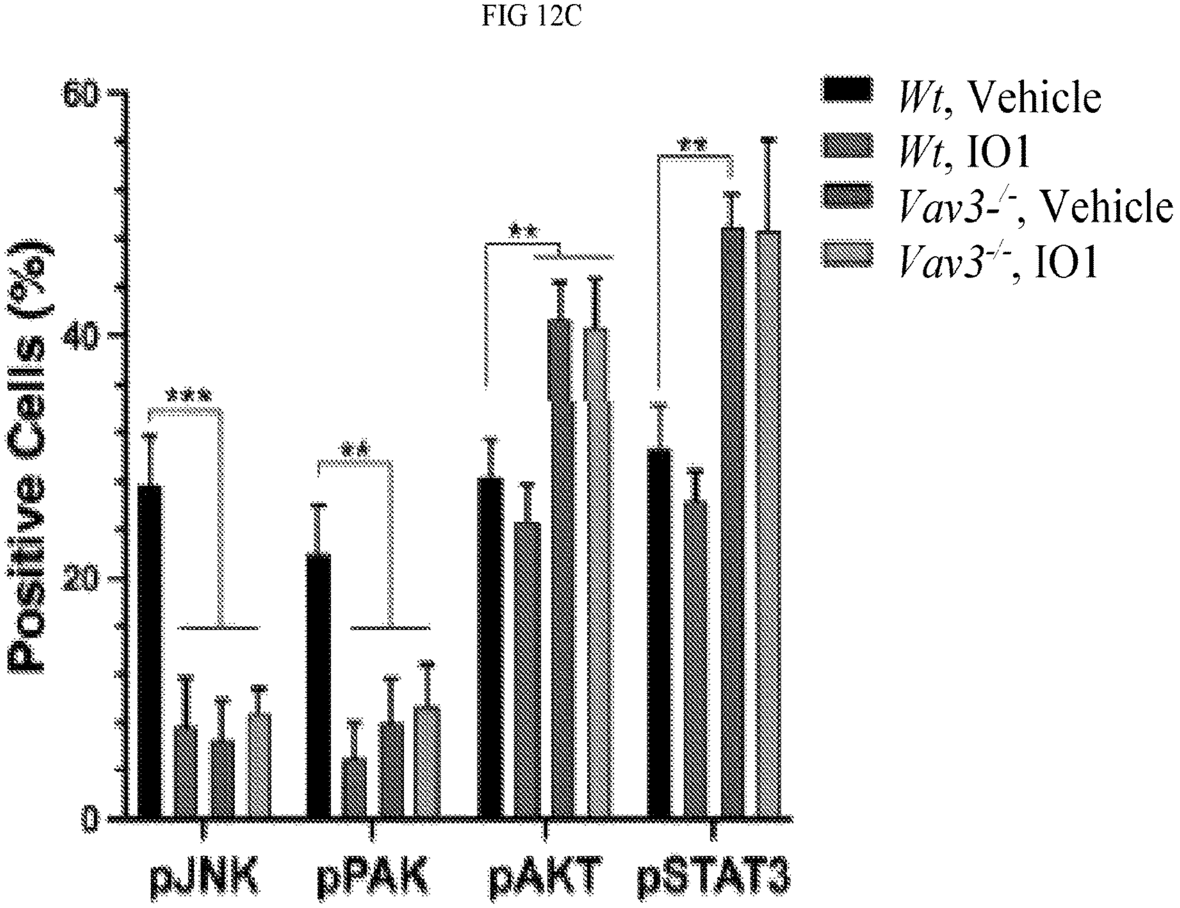
Figure 12D:
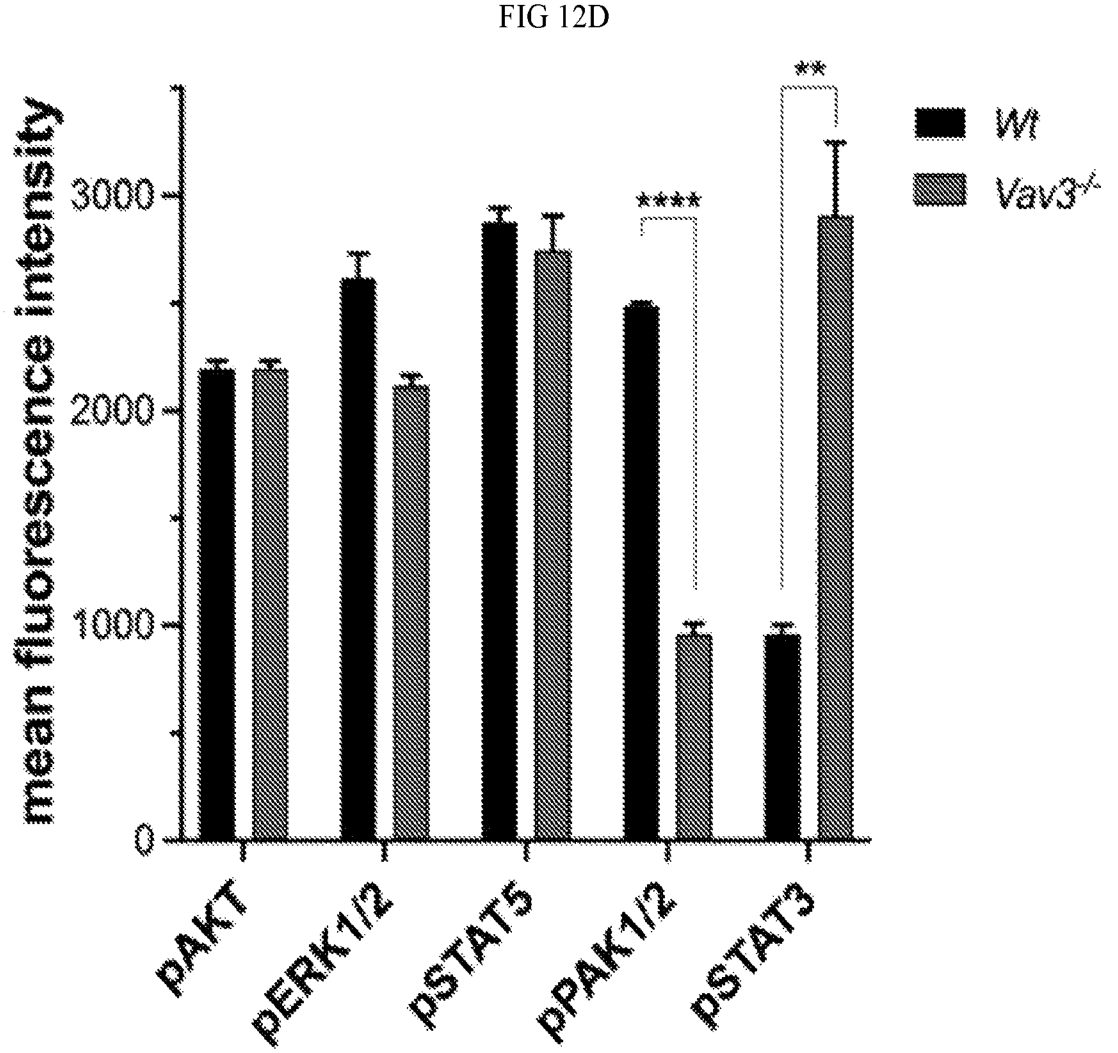
Figure 12E:
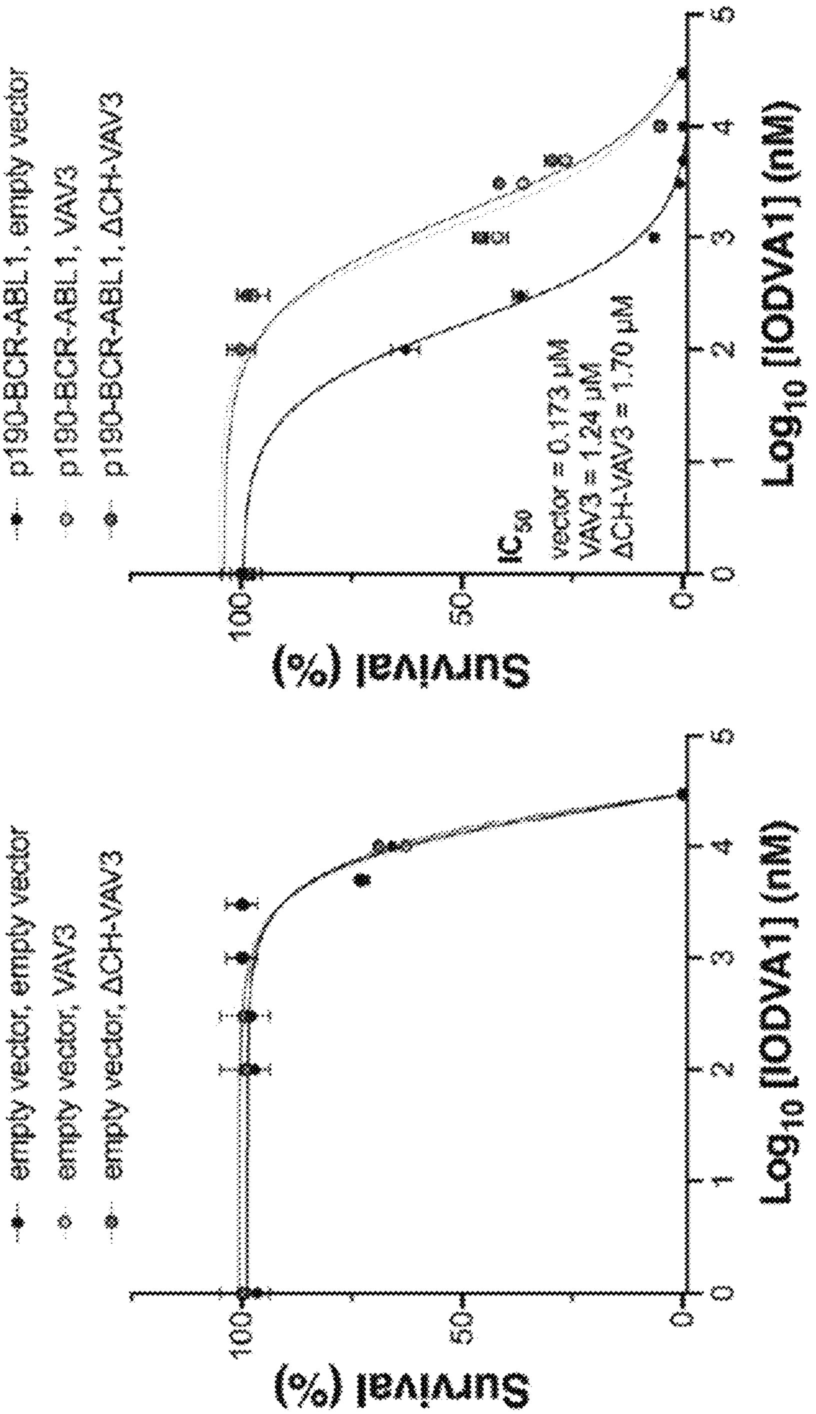
Figure 12F:
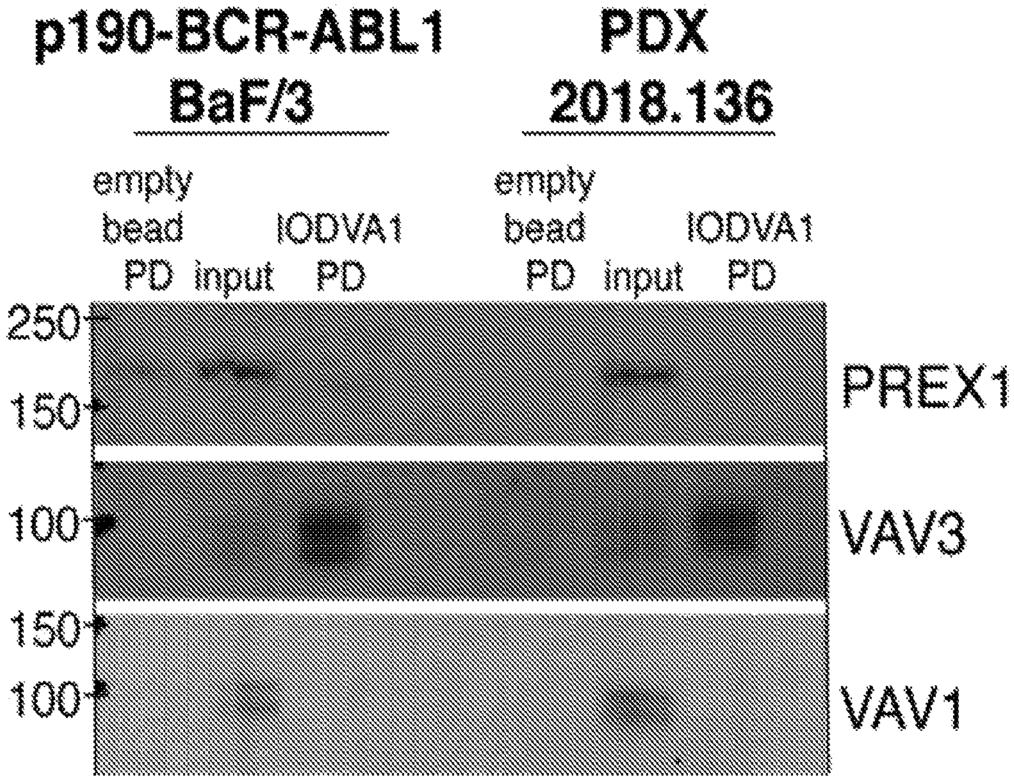
Figure 12G:
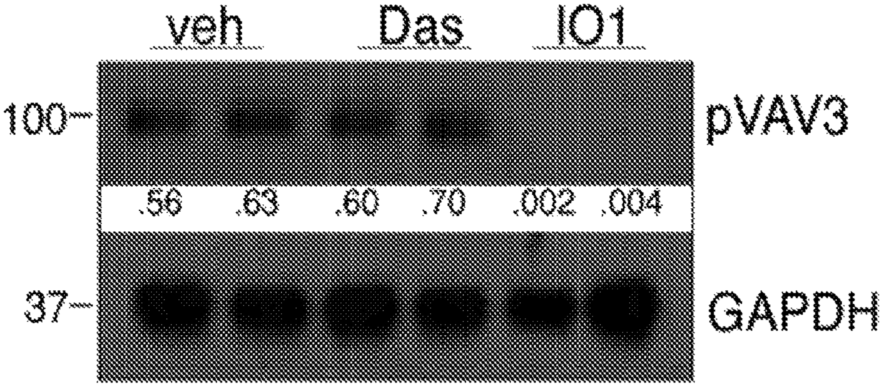

The observation that IODVA1 is superior to dasatinib prompted Applicant to check the ability of the ABL1-TKI to inhibit VAV3 phosphorylation. Applicant posited that dasatinib, an inhibitor of BCR-ABL1 and SRC-kinase family involved in VAV3 activation, should inhibit VAV3. Applicant compared levels of pVAV3 in BM of PDX 2018-136 mice treated with dasatinib and IODVA1 (FIG. 12G). IODVA1, but not dasatinib significantly decreased VAV3 activation. Thus, the effect of IODVA1 on prolonging the survival of PDX mice correlates with its superior ability at inhibiting VAV3 activation.

Figure 2E:
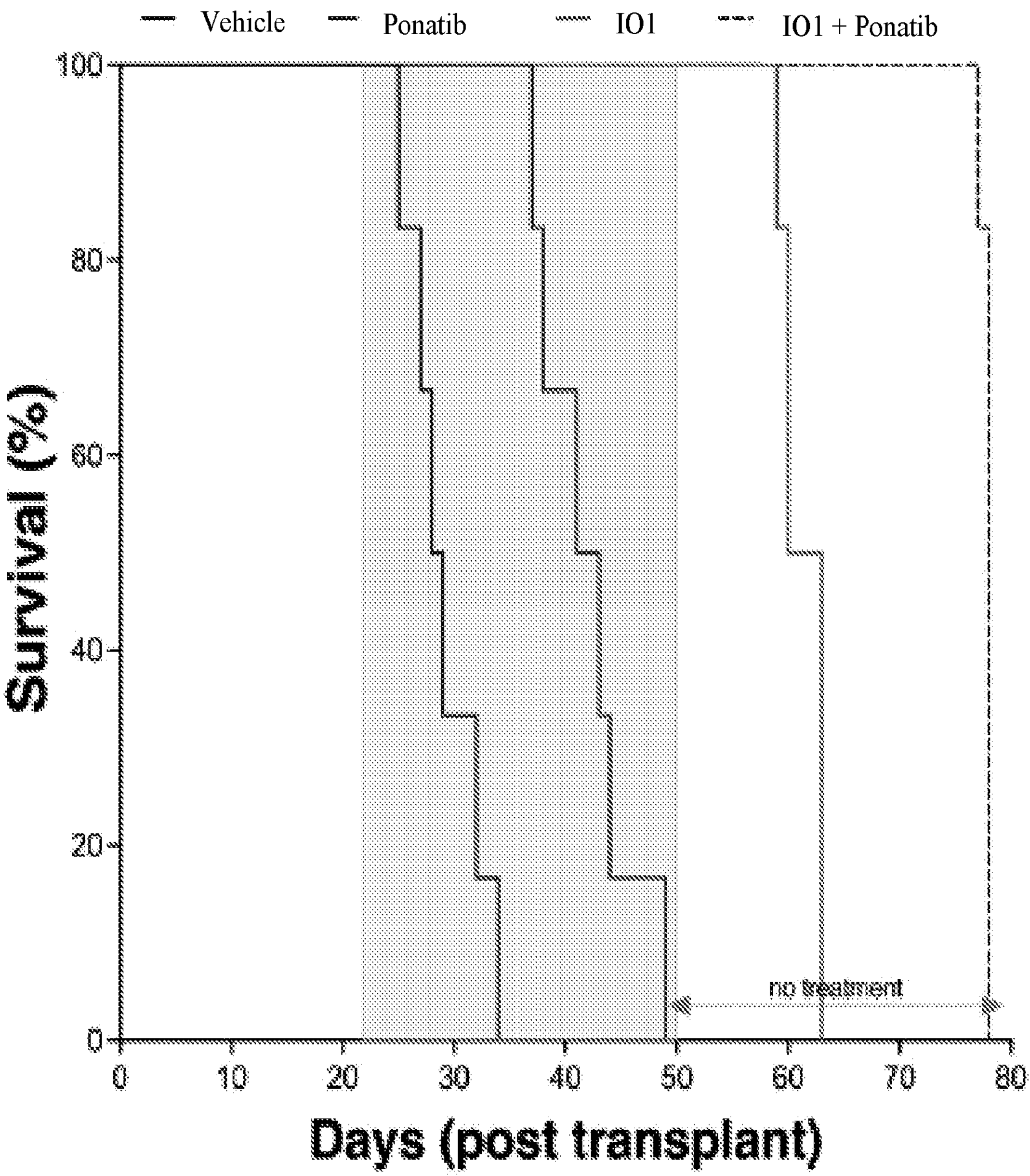
Figure 2F:
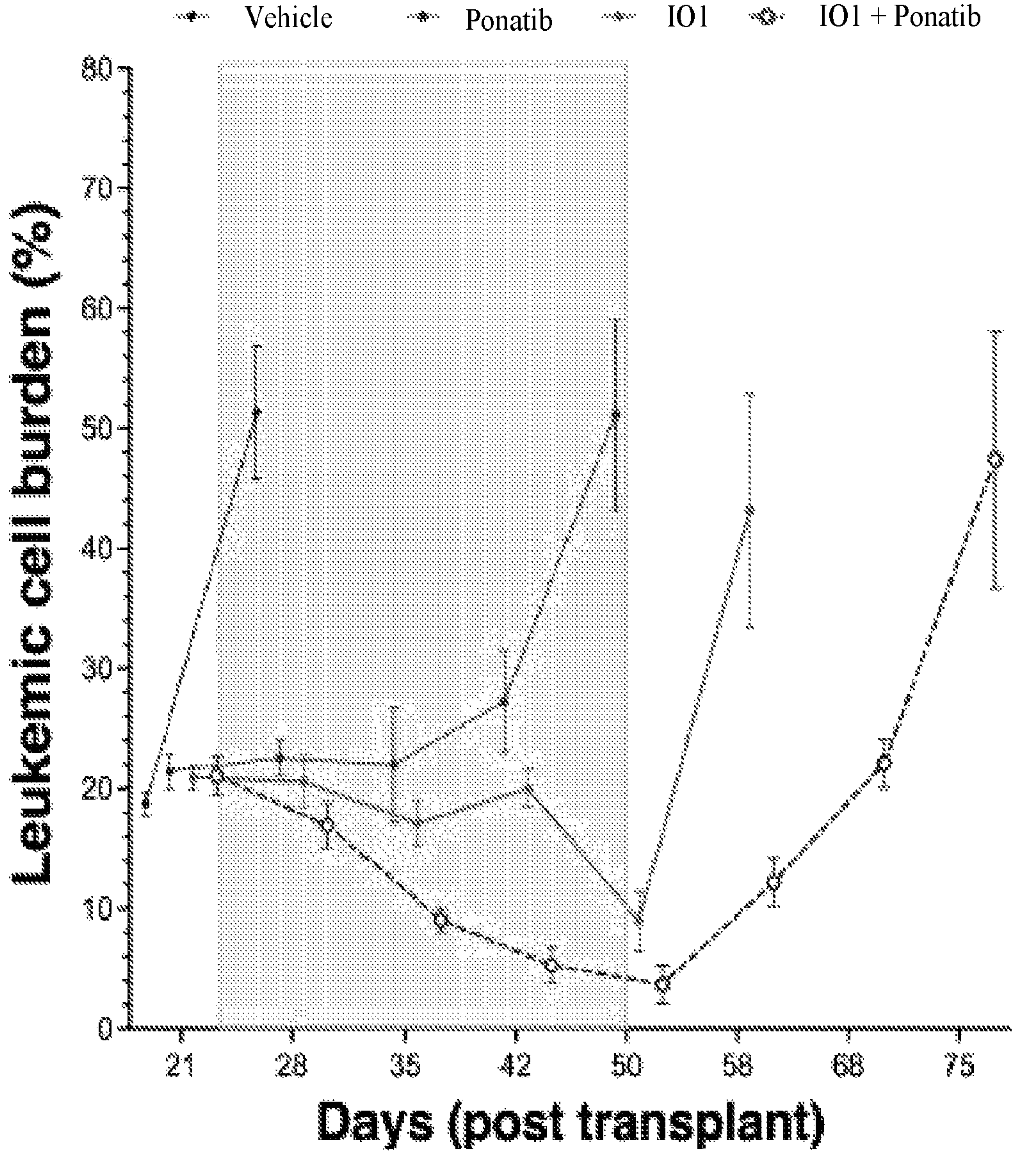

Next, to confirm that IODVA1 overcomes TKI-resistance in vivo using a patient sample, Applicant used NSG mice engrafted with cells from patient 2017-129 with $Ph^+$ (BCR-ABL1; T315I) and mutated SETD2, SF3B1, and TP53 with disease relapse after initial treatment. Mice were stratified into 4 groups of 6 mice each and administered either PBS vehicle control, IODVA1 (4 mM), ponatinib (0.5 mM), and the IODVA1+ponatinib combination in subcutaneous osmotic pumps for 4 weeks after which treatment was stopped (FIG. 2E). Vehicle-treated mice died between day 25 and 34. Ponatinib-treated mice survived significantly longer but died before treatment ended between day 37 and 49. IODVA1-treated mice died between day 59 and 63, or 9 to 13 days after treatment ended. The combo treatment increased leukemic mice survival the most as they died between day 77 and 78 or 27 and 28 days after treatment ended. Leukemic cell burden analysis (FIG. 2F) shows that ponatinib does not decrease the levels of leukemic cells in the peripheral blood. IODVA1 on the other hand decreases the leukemic burden by 57%, from 21.0±1.0% at the beginning of the treatment (day 21) to 9.0±2.5% at the end of the treatment (day 50). However, the IODVA1 mice still die from leukemia as the leukemic burden increases to 43.1±9.7% 8 days after treatment ended. The combo treatment decreased the leukemic burden 5.7-fold, from 21±1.6% to 3.7±1.6%, at the end of the treatment (day 50). However, the residual leukemic burden increased with time, eventually leading to death.

Figure 6C:
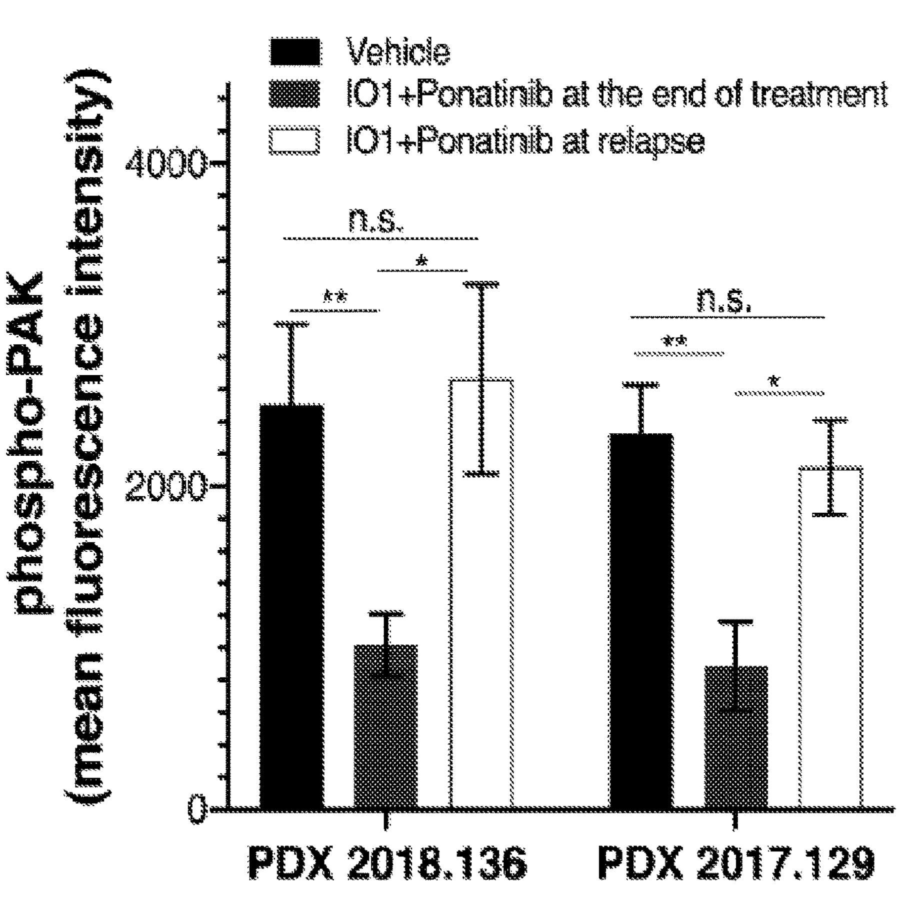
Figure 6C:
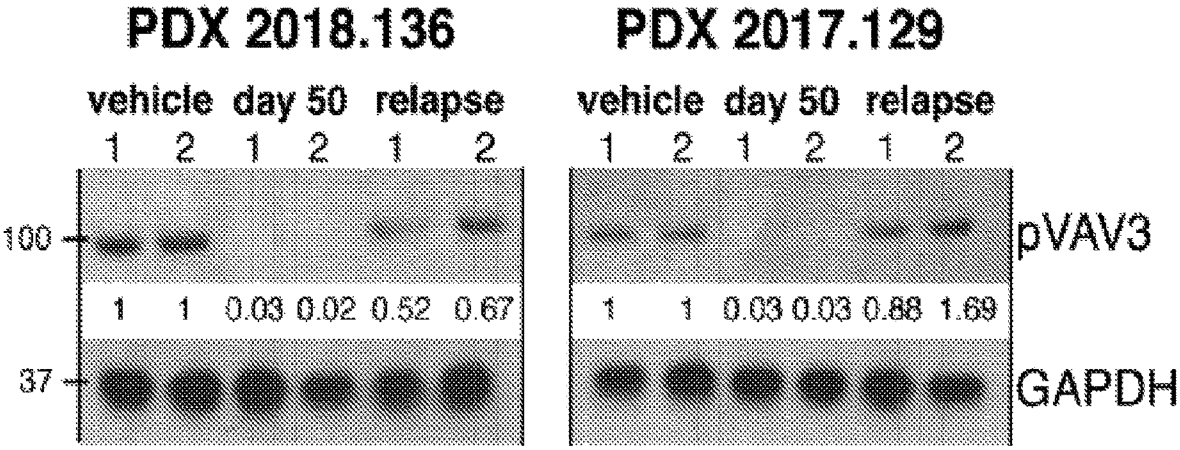

To test if IODVA1 targets the VAV3/RAC/PAK pathway in vivo, Applicant checked levels of pVAV3 and pPAK1/2 by immunoblotting or phospho-flow, respectively, in BM cell aspirates of vehicle and IODVA1+ponatinib treated mice from the two previous PDX models. pVAV3 levels are high in vehicle treated mice at the time of death but pVAV3 was hardly detectable in IODVA1+ponatinib treated mice at the end of treatment (day 50). Ending the combo treatment increased pVAV3 levels as a pVAV3 band is obvious at the time of animal sacrifice, days 10 and 92 or 78, respectively (FIG. 6C). pPAK1/2 follows the same pattern.

Taken together, in vivo PDX data show that IODVA1 is superior to standard-of-care drugs dasatinib and ponatinib and that IODVA1 and ponatinib synergize to prolong survival even after treatment has stopped. Consistent with Applicant's proposed MoA, IODVA1 decreases VAV3 activity in vitro and in vivo thus decreasing signaling through the RAC/PAK pathway and leading to leukemic progenitor stem cells death. However, if IODVA1 alone or in combination with ponatinib decreases residual leukemic disease even post treatment arrest, it does not completely eliminate it following 4 weeks treatment.

Discussion

VAV3 is a multi-domain tyrosine phosphorylation-dependent RacGEF that functions downstream of several different signaling molecules including immune response receptors, G-protein-coupled receptors (GPCRs), protein tyrosine kinases and integrins and is a critical component of BCR-ABL1 induced RAC activation[23,44]. Thus far, no small molecule inhibitor of VAV3 has been reported. If the small molecule EHop-016 was shown to inhibit the VAV1/RAC1 interaction it is not clear if it targets VAV1 directly[33]. Small molecule inhibitors of the RhoGEFs LARG, AKAP13, DOCK2, and DOCK5[45-49] have been identified in in vitro and cellular assays however, these molecules work at high concentrations and both their mechanism of action and their potential drug-likeness is questionable[50].

This study in cellular, murine models of the chimeric BCR-ABL1 oncoprotein, and in PDX models of $Ph^+$ B-ALL demonstrates that inhibitor of oncogene-driven VAV3 activation, IODVA1, binds tightly to VAV3 ($K_d$=512 nM, FIGS. 4B & 4C), prevents its activation, and the activation of RAC in vitro and in vivo. In accordance with this MoA, IODVA1 significantly decreased the levels of active VAV3 in xenograft tumors of triple negative breast cancer mouse model (FIG. 7C) and decreases the survival of various PDX B-ALL cells in a VAV3-dependent manner (FIGS. 10A-10D, & 6B) suggesting that IODVA1's inhibition of VAV3 is not model dependent. One can argue that IODVA1 inhibits BCR-ABL1 or the transmembrane or cytosolic protein tyrosine kinases such as SYK, Janus, TEK, ABL1/2, and SRC family kinases responsible for VAV3 phosphorylation [44] however, this is unlikely since IODVA1 is not a kinase inhibitor [11] and BCR-ABL1 phosphorylation levels are not affected by IODVA1 (FIG. 9). IODVA1 binds tightly to VAV3 and this binding seems specific as it does not bind RAC or LARG, does not interfere with the actions of p50GAP or RhoGDI1 and has no effect on $VAV3^{-/-}$ cells in vitro or in vivo. The possibility that IODVA1 inhibits the homologous VAV1/2 exists but based on the loss of IODVA1's efficacy in $VAV3^{-/-}$ models (FIG. 4D-4E) and its inability to affect VAV1 phosphorylation levels in primary patient cells (FIG. 6B), this inhibition is unlikely. Significantly, IODVA1 has no effect on $VAV3^{-/-}$ murine bone marrow leukemic cells and does not affect the survival of a mouse model of $VAV3^{-/-}$ p190-BCR-ABL1-induced leukemia. In addition, IODVA1 has no effect on $RAC1^{\Delta/\Delta}$+$RAC2^{-/-}$ leukemic cells (FIG. 3D). These in vivo and in vitro results are relevant because if IODVA1 had off-targets with a contribution to BCR-ABL1-driven leukemia, an increase in mouse survival and in cell proliferation would have been detected, which is not the case.

In vitro cell cycle and colony formation data indicate that IODVA1's pharmacological action on leukemic cells mimics the genetic deletion of VAV3 (FIGS. 4D & 4E) consistent with no off-target effects. The IODVA1-triggered increase in apoptosis (FIGS. 3C & 4E) is also in line with the increase in apoptosis observed in $VAV3^{-/-}$ leukemic cells [23]. Results from the colony formation assays with the $RAC1^{\Delta/\Delta}$+$RAC2^{-/-}$ leukemic cells (FIG. 3D) and from viability of shVAV3 MDA-MB-231 cells (FIG. 7A) are also consistent with this idea. $RAC1^{\Delta/\Delta}$+$RAC2^{-/-}$ leukemic cells resulted in higher number of colonies than cells treated with IODVA1. This can be explained by residual RAC1 (FIG. 11D), which is pro cell-proliferation or by the RAC-independent pathways regulated by VAV3 that are not inhibited by IODVA1. Likewise, there is a noticeable difference between IODVA1's pharmacological action, which increases survival of leukemic mice and VAV3 genetic deletion, which results in premature leukemic mice death (FIG. 12A). Phospho-flow cytometric data show however, that in the background of $VAV3^{-/-}$, BCR-ABL1 leukemic cells increase signaling through the pro-survival and VAV3/RAC-independent effectors AKT and STAT3 (FIG. 12C). This mechanism of adaptation is likely responsible for the proliferation of LSCs and the death of $VAV3^{-/-}$ leukemic mice (see also [23]).

IODVA1 decreases RAC activation and the activity of several of its downstream effectors such as PAK1, JNK, S6, and 4EBP in vitro and in vivo. The decrease in PAK1 activity leads to dephosphorylation and therefore activation of BAD. BAD activation prevents its association with Bcl2/Bcl-xL and promotes cell apoptosis. IODVA1-driven induction of apoptosis of BCR-ABL1 expressing cells is supported by cell cycle analysis in vitro and in vivo (FIGS. 3C & 4D). Most relevant to this MoA is the decrease in levels of pJNK, pPAK1, pS6, and p4EBP following IODVA1 administration to TKI-resistant BCR-ABL (T315I) leukemia model and the associated decrease in leukemic burden (FIG. 6A).

The expression of BCR-ABL1 in B-ALL confers a much poorer prognosis compared to other cytogenetic or molecular abnormalities [51]. Treatment with ABL1-TKIs has proven to be only partly effective in $Ph^+$ B-ALL patients. The relative failure of TKI therapy in these types of ALL is due to, among others, the development of resistance-inducing mutations such as ABL1-T315I and primary resistance of leukemic stem cells to TKI therapy [52]. In studies of patients with high-risk treatment-refractory B-cell ALL, a high frequency of recurrent somatic alterations was found in key signaling pathways such as the RAS/ERK, PI3K/AKT, B-cell development and differentiation, RAC/PAK, and Janus kinases [53,54]. An emerging concept to overcome TKI-shortcomings is to target leukemic stem cells (LSCs), which are responsible for disease initiation and propagation. Whereas imatinib alone does not eradicate LSCs in vivo, deletion of RAC2 in p210-BCR-ABL-transduced hematopoietic cells prolonged the survival of leukemic mice [4,5,22,30]. Similarly, genetic deficiency of VAV3 but not of VAV1/VAV2 delays leukemogenesis by p190-BCR-ABL1 and phenocopies the effect of RAC2 deficiency [23] suggesting that VAV3 and RAC GTPases are targets in BCR-ABL1 LSCs. IODVA1 eliminates residual leukemic stem/progenitor cells responsible for BCR-ABL1 B-ALL disease relapse in secondary transplant mice better than imatinib (FIG. 1D) and overcomes resistance to ABL1-TKI (FIG. 2). In PDX models of $Ph^+$ and TKI-resistant $Ph^+$ B-ALL with mutations commonly occurring in pediatric patients[55], Applicant found that IODVA1 fares better than standard of care dasatinib and ponatinib and that the IODVA1/ponatinib combination is a superior therapy. It reduces leukemic burden in peripheral blood even after treatment stopped but does not totally eliminate residual disease (FIGS. 2D & 2F) unlike what Applicant observed with models of BCR-ABL1 (FIGS. 1D & 2B). This discrepancy is likely due to the additional clonal evolution in relapsed patients. A longer IODVA1 treatment or more optimized drug combination may be used to address this outcome. Additional genetic lesions in relapsed patients may hinder the ability of dasatinib to indirectly inhibit VAV3 as efficiently as IODVA1 (FIG. 12G).

IODVA1 reduces the viability of primary cells from pediatric patients with $Ph^+$ B-ALL including TKI-resistant BCR-ABL1 (T315I), Ph-like, and MLL-rearrangements with superior potency than currently administered therapies (FIG. 12). Ph-like lymphoblastic leukemias are known to depend largely directly or indirectly on JAK-STAT tyrosine kinase signaling activation [56]. Data using pre-clinical models of CLRF2 mutant B-ALL (FIG. 10), the most frequent mutation in Ph-like B-ALL which induces activation downstream of IL7R through the JAK/STAT signaling pathway illustrates the effect of IODVA1 in an alternative tyrosine kinase receptor signaling pathway. On the other hand, MLL-rearranged lymphoblastic leukemias have been shown to have high expression of and exquisite dependence on FLT3, a tyrosine kinase receptor signaling in many[57], but not all[58] cases, which probably illustrates the heterogeneity of results observed in the responses to IODVA1 in primary human ALL specimens. The specificity of IODVA1 to the oncoprotein expressing cells (FIG. 1A) explains its low toxicity in vivo. IODVA1 is thus well-suited to treat $Ph^+$ and probably other leukemias with a superior suppression of growth and survival.

VAV3 can be roughly divided into two halves: (1) a catalytic N-terminal half responsible for RAC binding and activation and (2) an adaptor C-terminal half involved in protein-protein interactions (FIG. 5A). The nucleotide exchange activity of VAV3 is subject to tight regulation. It is accepted that upon cell stimulation, phosphorylation of conserved Tyr-residues (e.g. Tyr173) releases an autoinhibitory mechanism by the N-terminus calponin-homology CH-domain and acidic stretch (Ac) and the C-terminal SH3 domain, thus allowing GTPase access to the DH domain [10]. Based on biochemical data (FIGS. 4A & 6B), IODVA1 may inhibit VAV3 phosphorylation by preventing the access of tyrosine residues in the Ac-stretch to SRC kinases. IODVA1 likely locks VAV3 into the autoinhibitory state, thus preventing RAC from accessing the DH domain for activation. Consistent with this picture, rescue data with the ΔCH-mutant of VAV3, which unlike full-length VAV3, lost its sensitivity to IODVA1 (FIG. 5B-5C). These data suggest that the VAV3 calponin homology domain is part of IODVA1 binding site. The pulldown with biotinylated-IODVA1 (FIG. 4C) suggest that the C-terminal SH2/SH3 domains are dispensable for IODVA1 binding.

In conclusion, pharmacological inhibition of VAV3 by IODVA1 is therapeutically superior to inhibiting upstream kinases and thus an attractive therapeutic strategy to treat $Ph^+$ and TKI-resistant $Ph^+$ B-ALL, and may benefit other malignancies where VAV3 is a target. In addition, IODVA1 constitutes an exceptional tool to dissect the VAV3/RAC signaling axis. Broadly, RhoGEFs are multi-domain proteins that are regulated by autoinhibition. Consequently, small molecules that stabilize the autoinhibited conformation of RhoGEFs and inhibit their activity may be useful drugs to treat human cancers.

Methods

Plasmids, cell line, and reagents used in this work as well as viral particle production, transduction and transplantation, preparation for flow cytometry analysis, and SDS-PAGE, pull-down assays and immunoblotting are described in the Supplemental Methods section.

Recombinant Protein Cloning, Expression and Purification: For bacterial expression, full-length VAV3 was cloned as an MBP-fusion protein into pMalX (E) vector with N-terminal AAAA (SEQ ID NO: 1), AAAASEF (SEQ ID NO: 2) or AAAASEFGS (SEQ ID NO: 3) linkers using HiFi assembly (NEB). N-VAV3 (aa 1-575) was cloned as a His6-tagged protein into pProEx-HTB vector. All constructs were verified using Sanger sequencing using CCHCM DNA Core. To minimize aggregation and improve on quality of purified protein, the expression clones were tested with chaperone plasmids according to the manufacturer's protocol (Takara).

For production of recombinant full-length and truncated VAV3, plasmids were co-transformed with chaperone plasmid Gro7 groEL-groES in BL21 (DE3) or T7 Express. Cultures were grown in LB, supplemented with metal mix.

Protein was purified using Ni-IMAC chromatography, followed by size-exclusion gel filtration (HiLoad Superdex 200 16/60). Post SDS-PAGE analysis, fractions containing VAV3 were pooled, concentrated to ~10 mg/mL and flash frozen in liquid nitrogen. Final yield was 10-20 mg per 6 L of culture. Recombinant LARG (DH/PH) was purified as His6-MBP-fusion protein using IMAC, followed by size-exclusion gel filtration as above.

Microscale Thermophoresis (MST): Purified VAV3, LARG or RAC (1 μM) were incubated with the indicated concentrations of IODVA1 at room temperature for 30 min. Samples were loaded into Zero Background MST Premium Coated capillaries and binding events were measured on Monolith NT.LabelFree (NanoTemper Technologies). Binding data were analyzed using Thermophoresis or Thermophoresis with Temperature Jump analysis. Data were normalized using fraction-bound binding. The 95% confidence interval for $K_d$ values was 0.27 to 0.98 μM for VAV3, 5.9 to 10.37 μM for LARG, and 19.6 to 105.8 μM for RAC.

Animals and in vivo Drug Administration: VAV3-deficient mice [59] and $RAC1^{\Delta/\Delta}$+RAC2-deficient [4] mice have been described previously. C57Bl/6 and NSG (NOD/SCID/$IL2RG^{-/-}$) mice were commercially obtained (The Jackson Laboratory and Harlan Laboratories) and used as donors and/or recipients of transduction/transplantation models under a protocol approved by The Cincinnati Children's Hospital Medical Center Institutional Animal Care and Use Committee. For in vivo drug administration, Alzet implantable osmotic pumps (Model 2002, Durect) were used according to the manufacturer's protocol and implantation was done as described previously[4].

Primary PDX samples: Primary patient specimens were obtained from patients at CCHMC according to Institutional Review Board Approved protocols (#2008-0021 and #2008-0658). Samples were subjected to RBC lysis and the isolated WBCs were mixed with OKT3 anti-CD3 antibody to eliminate the potential for xenogenic Graft Versus Host Disease before injection into busulfan conditioned NSG or NRG mice[60].

For analysis of proliferation during drug treatment, spleen preparations from mice successfully engrafted with B-ALL were co-cultured with MS-5 or OP9 stroma in MEMα media supplemented with 20% FBS and 10 ng/mL recombinant human SCF (Kit-L), Flt3L, and IL-7 (KF7). Drug treatment was started 24 h after initial seeding. Co-cultures were collected by trypsinization after 7 days and cell counts were performed with trypan blue. Flow cytometry was performed with mCD45-APC-Cy7 (BD), hCD45-FITC (BD), hCD19-VioBlue (Miltenyi Biotech), and 7-AAd (for viability) to determine percentage of human ALL in the cultures. Total absolute ALL cell numbers were determined by multiplying cell counts by percentage human ALL cells.

For in vivo drug treatments, cells isolated from PDX 2018-136 and 2017-129 were transplanted into lethally irradiated NSG mice and treated as described above in Animals and in vivo Drug Administration and in Supplemental Info.

Histology: Embedded tissues were cut into 4 μm sections then immunohistochemically stained using the Mouse on Mouse kit (MoM kit, Vector Laboratories). Tissue sections were subjected to sodium citrate antigen retrieval, pretreated with 0.3% hydrogen peroxide, blocked according to kit directions, and incubated with an antibody to phosphorylated VAV3 (Abcam) and HRP-conjugated anti-rabbit secondary (Vector Laboratories). Staining was completed with the DAB Peroxidase kit (Vector Laboratories) and counterstained with hematoxylin. Tissue sections were coverslipped with Cytoseal 60 and images acquired with a Nikon Eclipse Ci microscope.

CFU-proB Assay: B-cell lineage colony-forming units (CFU-proB) were quantified post 9-day culture of leukemic BM cells or sorted for p190-BCR-ABL1-expressing B-cell progenitors in M3134 methylcellulose (StemCell Technologies) supplemented with 30% FBS (for mouse B lymphoid colony forming cells; StemCell Technologies), 2 mM L-glutamine and 1% penicillin-streptomycin (Invitrogen), 100 μM β-mercaptoethanol (Fisher-Scientific), 1% BSA (Sigma-Aldrich), 20 ng/mL of recombinant mIL-7 and 100 ng/ml of recombinant mSCF (PeproTech).

Cell Cycle Analysis: Cell cycle was analyzed via in vitro BrdU incorporation (BD Pharmingen, Cat #552598). Briefly, leukemic progenitors were incubated with 1 mM BrdU solution for 45 minutes, cells were further fixed and permeabilized. DNAse treatment was done according to the instructions and stained with anti BrdU and apoptosis was analyzed by 7-AAD staining through flow cytometry analysis.

Statistical Analysis: Statistical analyses were performed in GraphPad Prism v.8. Additionally, *Essential Statistics for the Pharmaceutical Sciences* (Philip Rowe) was consulted to choose appropriate statistical tests. Comparison of two groups was carried out using Student's t-test, comparison of datasets with more than two groups was carried out using One- or Two-way ANOVA, as appropriate, with recommended multiple comparisons tests. Alpha was set to 0.05.

REFERENCES

1. Etienne-Manneville, S. & Hall, A. Rho GTPases in cell biology. *Nature* 420, 629-35 (2002).
2. Mack, N. A., Whalley, H. J., Castillo-Lluva, S. & Malliri, A. The diverse roles of Rac signaling in tumorigenesis. Cell Cycle 10, 1571-81 (2011).
3. Qiu, R. G., Chen, J., Kirn, D., McCormick, F. & Symons, M. An essential role for Rac in Ras transformation. *Nature* 374, 457-9 (1995).
4. Thomas, E. K. et al. Rac guanosine triphosphatases represent integrating molecular therapeutic targets for BCR-ABL-induced myeloproliferative disease. *Cancer Cell* 12, 467-78 (2007).
5. Sengupta, A., Arnett, J., Dunn, S., Williams, D. A. & Cancelas, J. A. Rac2 GTPase deficiency depletes BCR-ABL+leukemic stem cells and progenitors in vivo. *Blood* 116, 81-4 (2010).
6. Mizukawa, B. et al. Inhibition of Rac GTPase signaling and downstream prosurvival Bcl-2 proteins as combination targeted therapy in MLL-AF9 leukemia. *Blood* 118, 5235-45 (2011).
7. Mulloy, J. C. et al. Rho GTPases in hematopoiesis and hemopathies. *Blood* 115, 936-47 (2010).
8. Cardama, G. A. et al. Relevance of small GTPase Rac1 pathway in drug and radio-resistance mechanisms: Opportunities in cancer therapeutics. *Crit Rev Oncol Hematol* 124, 29-36 (2018).
9. Barreira, M. et al. The C-terminal SH3 domain contributes to the intramolecular inhibition of Vav family proteins. *Sci Signal* 7, ra35 (2014).
10. Yu, B. et al. Structural and energetic mechanisms of cooperative autoinhibition and activation of Vav1. *Cell* 140, 246-56 (2010).
11. Gasilina, A. et al. IODVA1, a guanidinobenzimidazole derivative, targets Rac activity and Ras-driven cancer models. *PLOS One* 15, e0229801 (2020).

12. Arrigoni, E. et al. Concise Review: Chronic Myeloid Leukemia: Stem Cell Niche and Response to Pharmacologic Treatment. *Stem Cells Transl Med* 7, 305-314 (2018).

13. Hamilton, A. et al. Chronic myeloid leukemia stem cells are not dependent on Bcr-Abl kinase activity for their survival. *Blood* 119, 1501-10 (2012).

14. Rizo, A. et al. BMI1 collaborates with BCR-ABL in leukemic transformation of human CD34+ cells. *Blood* 116, 4621-30 (2010).

15. Mullighan, C. G. et al. Genome-wide analysis of genetic alterations in acute lymphoblastic leukaemia. *Nature* 446, 758-64 (2007).

16. Mullighan, C. G. et al. BCR-ABL1 lymphoblastic leukaemia is characterized by the deletion of Ikaros. *Nature* 453, 110-4 (2008).

17. Churchman, M. L. et al. Efficacy of Retinoids in IKZF1-Mutated BCR-ABL1 Acute Lymphoblastic Leukemia. *Cancer Cell* 28, 343-56 (2015).

18. Williams, R. T. & Sherr, C. J. BCR-ABL and CDKN2A: a dropped connection. *Nat Rev Cancer* 8, 563; author reply 563 (2008).

19. Figueroa, M. E. et al. Integrated genetic and epigenetic analysis of childhood acute lymphoblastic leukemia. *J Clin Invest* 123, 3099-111 (2013).

20. Cilloni, D. & Saglio, G. Molecular pathways: BCR-ABL. Clinical cancer research: an official journal of the American Association for Cancer Research 18, 930-7 (2012).

21. Roberts, K. G. et al. Genetic alterations activating kinase and cytokine receptor signaling in high-risk acute lymphoblastic leukemia. *Cancer Cell* 22, 153-66 (2012).

22. Skorski, T. et al. BCR/ABL-mediated leukemogenesis requires the activity of the small GTP-binding protein Rac. *Proc Natl Acad Sci USA* 95, 11858-62 (1998).

23. Chang, K. H. et al. Vav3 collaborates with p190-BCR-ABL in lymphoid progenitor leukemogenesis, proliferation, and survival. *Blood* 120, 800-11 (2012).

24. Cho, Y. J. et al. Generation of rac3 null mutant mice: role of Rac3 in Bcr/Abl-caused lymphoblastic leukemia. *Mol Cell Biol* 25, 5777-85 (2005).

25. Milojkovic, D. & Apperley, J. Mechanisms of Resistance to Imatinib and Second-Generation Tyrosine Inhibitors in Chronic Myeloid Leukemia. *Clin Cancer Res* 15, 7519-7527 (2009).

26. Bixby, D. & Talpaz, M. Mechanisms of resistance to tyrosine kinase inhibitors in chronic myeloid leukemia and recent therapeutic strategies to overcome resistance. *Hematology Am Soc Hematol Educ Program,* 461-76 (2009).

27. Gorre, M. E. et al. Clinical resistance to STI-571 cancer therapy caused by BCR-ABL gene mutation or amplification. *Science* 293, 876-80 (2001).

28. Minden, A., Lin, A., Claret, F. X., Abo, A. & Karin, M. Selective activation of the JNK signaling cascade and c-Jun transcriptional activity by the small GTPases Rac and Cdc42Hs. Cell 81, 1147-57 (1995).

29. Saci, A., Cantley, L. C. & Carpenter, C. L. Rac1 regulates the activity of mTORC1 and mTORC2 and controls cellular size. *Mol Cell* 42, 50-61 (2011).

30. Thomas, E. K., Cancelas, J. A., Zheng, Y. & Williams, D. A. Rac GTPases as key regulators of p210-BCR-ABL-dependent leukemogenesis. *Leukemia* 22, 898-904 (2008).

31. Biswas, M. et al. MBD3/NuRD loss participates with KDM6A program to promote DOCK5/8 expression and Rac GTPase activation in human acute myeloid leukemia. *FASEB J* 33, 5268-5286 (2019).

32. Chatterjee, S. S., Biswas, M., Boila, L. D., Banerjee, D. & Sengupta, A. SMARCB1 Deficiency Integrates Epigenetic Signals to Oncogenic Gene Expression Program Maintenance in Human Acute Myeloid Leukemia. *Mol Cancer Res* 16, 791-804 (2018).

33. Martin, H. et al. Pak and Rac GTPases promote oncogenic KIT-induced neoplasms. *J Clin Invest* 123, 4449-63 (2013).

34. Lyons, R. et al. The RAC specific guanine nucleotide exchange factor Asef functions downstream from TEL-AML1 to promote leukaemic transformation. *Leuk Res* 34, 109-15 (2010).

35. Reuther, G. W. et al. Leukemia-associated Rho guanine nucleotide exchange factor, a Dbl family protein found mutated in leukemia, causes transformation by activation of RhoA. *J Biol Chem* 276, 27145-51 (2001).

36. Rouard, H., Tamasdan, S., Fridman, W. H. & Teillaud, J. L. Vav and SLP-76 recruitment by cross-linking of FcgammaRIIa1 in promyelocytic HL-60 cells. *Immunol Lett* 68, 347-53 (1999).

37. Bourgoin, S., Harbour, D., Desmarais, Y., Takai, Y. & Beaulieu, A. Low molecular weight GTP-binding proteins in HL-60 granulocytes. Assessment of the role of ARF and of a 50-kDa cytosolic protein in phospholipase D activation. *J Biol Chem* 270, 3172-8 (1995).

38. Hilfenhaus, G. et al. Vav3-induced cytoskeletal dynamics contribute to heterotypic properties of endothelial barriers. *J Cell Biol* 217, 2813-2830 (2018).

39. Chen, X. et al. Vav3 oncogene is upregulated and a poor prognostic factor in breast cancer patients. *Oncol Lett* 9, 2143-2148 (2015).

40. Lee, K. et al. Vav3 oncogene activates estrogen receptor and its overexpression may be involved in human breast cancer. *BMC Cancer* 8, 158 (2008).

41. Aguilar, H. et al. VAV3 mediates resistance to breast cancer endocrine therapy. *Breast Cancer Res* 16, R53 (2014).

42. Citterio, C. et al. The rho exchange factors vav2 and vav3 control a lung metastasis-specific transcriptional program in breast cancer cells. *Sci Signal* 5, ra71 (2012).

43. Lorenzo-Martin, L. F. et al. Vav proteins maintain epithelial traits in breast cancer cells using miR-200c-dependent and independent mechanisms. *Oncogene* 38, 209-227 (2019).

44. Bustelo, X. R. Vav family exchange factors: an integrated regulatory and functional view. *Small GTPases* 5, 9 (2014).

45. Shang, X. et al. Small-molecule inhibitors targeting G-protein-coupled Rho guanine nucleotide exchange factors. *Proc Natl Acad Sci USA* 110, 3155-60 (2013).

46. Diviani, D. et al. Small-Molecule Protein-Protein Interaction Inhibitor of Oncogenic Rho Signaling. *Cell Chem Biol* 23, 1135-1146 (2016).

47. Nishikimi, A. et al. Blockade of inflammatory responses by a small-molecule inhibitor of the Rac activator DOCK2. *Chem Biol* 19, 488-97 (2012).

48. Vives, V. et al. The Rac1 exchange factor Dock5 is essential for bone resorption by osteoclasts. *J Bone Miner Res* 26, 1099-110 (2011).

49. Bouquier, N. et al. A cell active chemical GEF inhibitor selectively targets the Trio/RhoG/Rac1 signaling pathway. *Chem Biol* 16, 657-66 (2009).

50. Gray, J. L., von Delft, F. & Brennan, P. Targeting the Small GTPase Superfamily through their Regulatory Proteins. *Angew Chem Int Ed Engl* (2019).

51. Arico, M. et al. Outcome of treatment in children with Philadelphia chromosome-positive acute lymphoblastic leukemia. *The New England journal of medicine* 342, 998-1006 (2000).

52. Corbin, A. S. et al. Human chronic myeloid leukemia stem cells are insensitive to imatinib despite inhibition of BCR-ABL activity. *The Journal of clinical investigation* 121, 396-409 (2011).

53. Hunger, S. P. & Mullighan, C. G. Redefining ALL classification: toward detecting high-risk ALL and implementing precision medicine. *Blood* 125, 3977-87 (2015).

54. Zhang, J. et al. Key pathways are frequently mutated in high-risk childhood acute lymphoblastic leukemia: a report from the Children's Oncology Group. *Blood* 118, 3080-7 (2011).

55. Waanders, E. et al. Mutational landscape and patterns of clonal evolution in relapsed pediatric acute lymphoblastic leukemia. *Blood Cancer Discov* 1, 96-111 (2020).

56. Tran, T. H. & Loh, M. L. Ph-like acute lymphoblastic leukemia. *Hematology Am Soc Hematol Educ Program* 2016, 561-566 (2016).

57. Furuichi, Y. et al. Fms-like tyrosine kinase 3 ligand stimulation induces MLL-rearranged leukemia cells into quiescence resistant to antileukemic agents. *Cancer Res* 67, 9852-61 (2007).

58. Stam, R. W. et al. Targeting FLT3 in primary MLL-gene-rearranged infant acute lymphoblastic leukemia. *Blood* 106, 2484-90 (2005).

59. Fujikawa, K. et al. Vav1/2/3-null mice define an essential role for Vav family proteins in lymphocyte development and activation but a differential requirement in MAPK signaling in T and B cells. *J Exp Med* 198, 1595-608 (2003).

60. Wunderlich, M. et al. OKT3 prevents xenogeneic GVHD and allows reliable xenograft initiation from unfractionated human hematopoietic tissues. *Blood* 123, e134-44 (2014).

SupplementalResults

IODVA1 specifically targets BCR-ABL1 B-ALL cells in vitro. Applicant tested the efficacy of IODVA1 in two commonly used $Ph^+$ cell models, Ba/F3 cells transduced with p190- or p210-BCR-ABL1 and NALM-1 cells. Ba/F3 cells are bone marrow-derived, IL-3 dependent, murine pro-B cells widely used in studying the mechanism of leukemia initiation and progression and targeted therapy discovery[1]. NALM-1 are human lymphoblastic cells that express p190-BCR-ABL1 but not Ikaros (IKZF1)[2]. Applicant treated Ba/F3 cells transduced with retrovirus encoding either p190- or p210-BCR-ABL1 or Mieg3 empty vector[3] control as before. Cells were grown in suspension in the presence of IL-3 and IODVA1 and counted daily for 3 days by trypan blue exclusion. At 3 μM, IODVA1 reduced the viability of p190- and p210-BCR-ABL1 expressing cells by 75±4% (SEM, N=9) at day 1; viability of Mieg3 empty vector expressing cells was not affected (FIG. 8, A). Plot of the concentration-dependent cell survival at the 72-hour time point shows that IODVA1 inhibits survival of p190-BCR-ABL1-Ba/F3 cells grown in the presence of IL-3 with a half maximal effective concentration (EC50) of 380 nM (95% CI 302 to 473 nM). IL-3 withdrawal renders p190-BCR-ABL1 BaF/3 cells more sensitive to IODVA1 (EC50 of 9 nM). Survival of empty vector expressing Ba/F3 cells was not affected by IODVA1 up to 5 μM and was reduced by 25.5% at 20 μM (FIG. 8, B). Similarly, IODVA1 decreases survival of NALM-1 cells with EC50 of 677 nM (95% CI 600 to 767.5 nM).

Figure 8A:
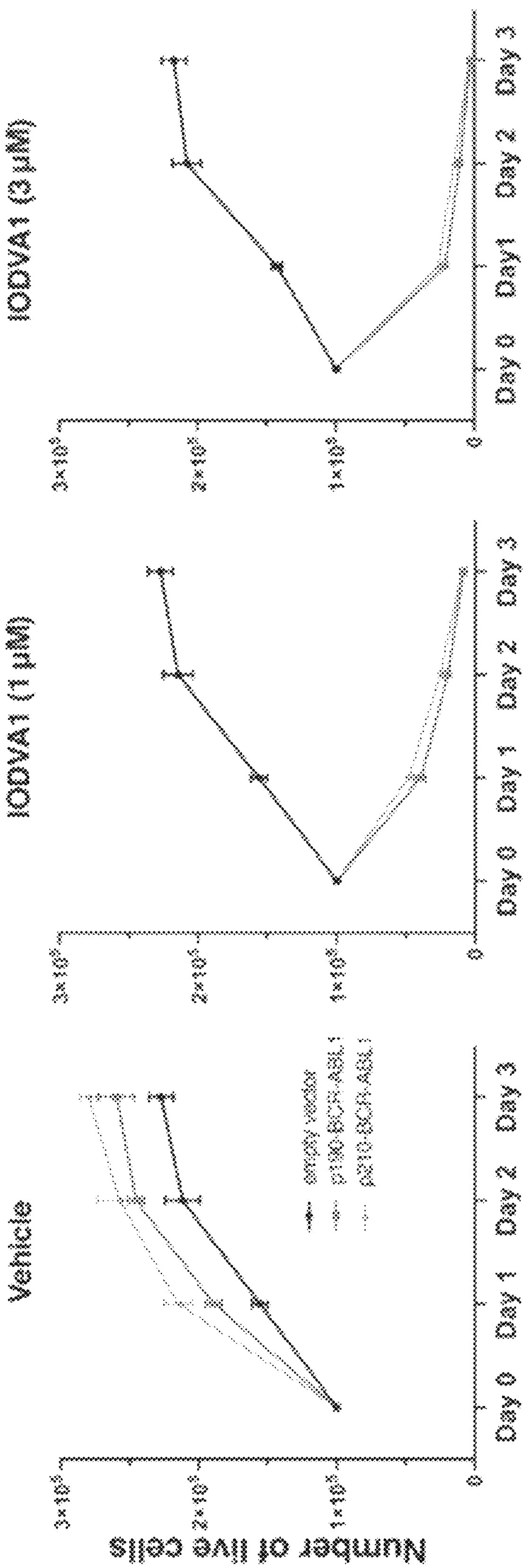
FIGS. 8A-8J depict data showing that IODVA1 inhibits the proliferation and survival of BCR-ABL1 expressing cells in vitro and in vivo and eradicates leukemia-propagating cells in secondary transplants. (8A) Ba/F3 cells transduced with p190-BCR-ABL1 (squares), p210 -BCR-ABL1 (triangles), or empty vector (black circles) were grown in the presence of vehicle control or IODVA1 at 1 and 3 μM and counted daily for 3 days using trypan blue exclusion. Mean±SD of a representative experiment done in triplicates is shown. (8B) IODVA1-dependent survival curves of empty vector (black circles), p190-BCR-ABL1 expressing Ba/F3 cells grown in the absence (orange circles) or presence (circles) of IL-3 and of Nalm-1 cells. Fitting of the data was done in Prism version 8.4. Combined mean±SEM of all experiments is shown. (8C) p190-BCR-ABL1 expressing Ba/F3 cells were allowed to grow for 1 day, treated with IODVA1 (IO1, 1 μM) for 1 day, and washed. Cells were counted for 7 days using trypan blue exclusion. Mean±SD of a representative experiment done in triplicates is shown. (8D) Ba/F3 cells stably expressing p190-BCR-ABL1 were subjected to colony formation assay in soft agar in the presence of DMSO or IODVA1 (1 or 10 μM). Colonies were allowed to form for 10 days then stained with iodonitrotetrazolium. Data shown are representative of three independent experiments done in triplicates. Note the smaller colony size in 1 μM IODVA1 treatment group. (8E) Leukemic burden (%) of treated mice before treatment and at the indicated treatment time was analyzed by flow cytometry of bone marrow aspirates as population containing $B220^+/CD43^+$ pro-B cells. N=3 mice per group. (8F) Count (%) of residual leukemic ($EGFP^+$-BCR-ABL1) cells in peripheral blood at weeks 3 and 5 for the secondary transplant mice from FIG. 1D. (8G) Kaplan-Meier survival plot of secondary mice transplants with the $0.3\times10^6$ cell-dilution. (8H) Count (%) of residual leukemic ($EGFP^+$-BCR-ABL1) cells in peripheral blood at weeks 3 and 5 for the secondary transplant mice from (8G). (8I & 8J) like 8G & 8H but with the $0.1\times10^6$ cell-dilution. N=5 mice per group in 8F-8J. *p≤0.05 using One-way ANOVA with Tukey's multiple comparison test.
Figure 8B:
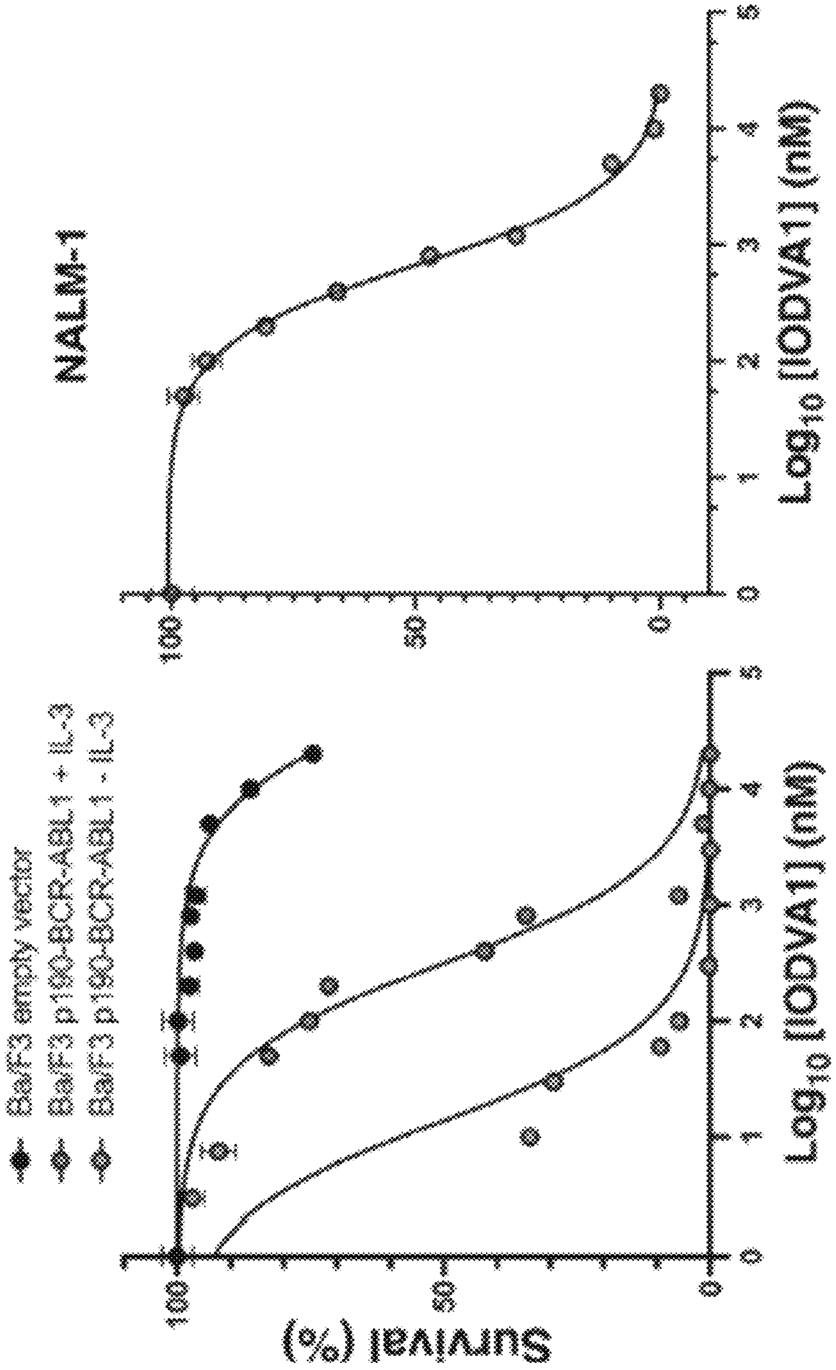
Figure 8C:
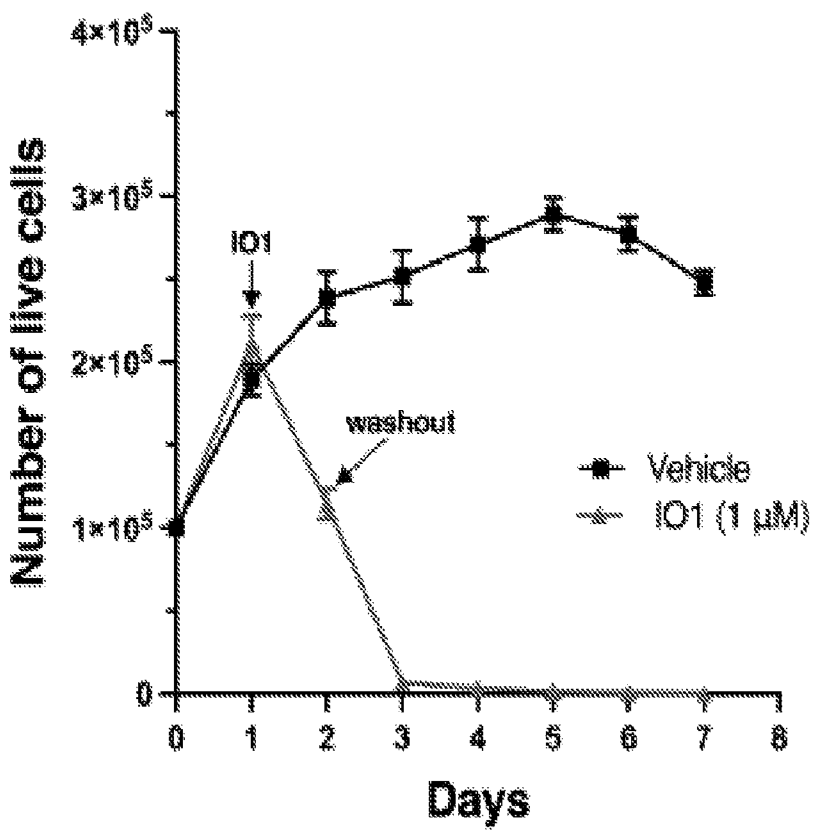

To test if the action of IODVA1 is reversible, Applicant incubated p190-BCR-ABL1 expressing Ba/F3 cells with IODVA1 (1 μM) for 24 h then washed the cells with media and counted them for 6 additional days (FIG. 8C). As expected, p190-BCR-ABL1 Ba/F3 cells started dying following IODVA1 incubation and kept dying even after IODVA1 removal (washout, arrow). By day 3, allowing for one round of cell division, all cells were dead suggesting that IODVA1 triggers an irreversible cell death program.

Figure 8D:
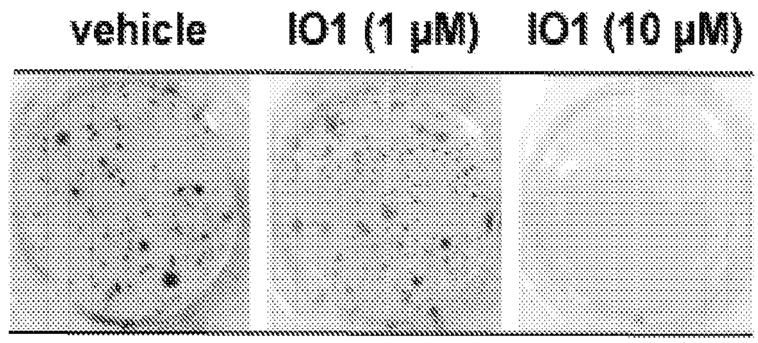
Figure 8E:
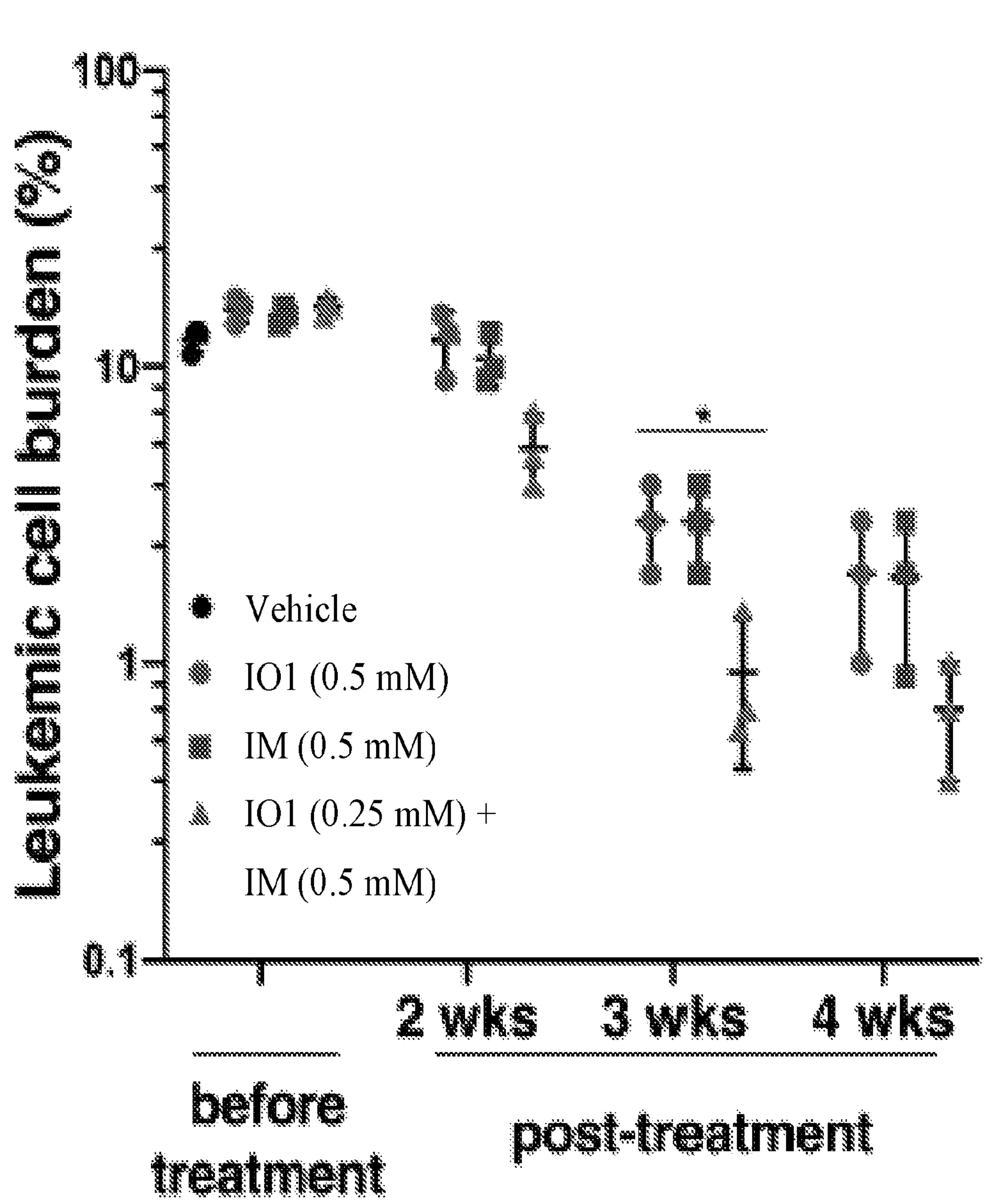

Applicant tested the ability of IODVA1 to inhibit the clonogenic ability of BCR-ABL1 expressing Ba/F3 cells in soft agar. At 10 μM, IODVA1 completely abolished colony formation of Ba/F3 cells transduced with p190-BCR-ABL1 vector (FIG. 8D). Colonies are noticeable at 1 μM albeit they are smaller than vehicle DMSO control probably indicative of slowed cell division rate.

IODVA1 prevents leukemia-related death and significantly decreases the leukemia burden in BCR-ABL1-induced leukemic murine model. To check if IODVA1 decreases the leukemia burden, Applicant analyzed by flow cytometry the residual p190-BCR-ABL1 expressing leukemic progenitor B-cells ($EGFP^+/B220^+$) from peripheral blood of vehicle- and drug-treated mice. All groups had comparable levels of circulating blasts between 12 and 16% at the start of the treatment (FIG. 8E). As the treatment progressed, the number of $EGFP^+/B220^+$ cells decreased to reach 1 to 2% at week 4. Although the data showed a trend for the IODVA1+imatinib combination to eliminate leukemic burden better than either drug alone, statistical analysis revealed that this trend may not be significant (p=0.186).

Figure 8F:
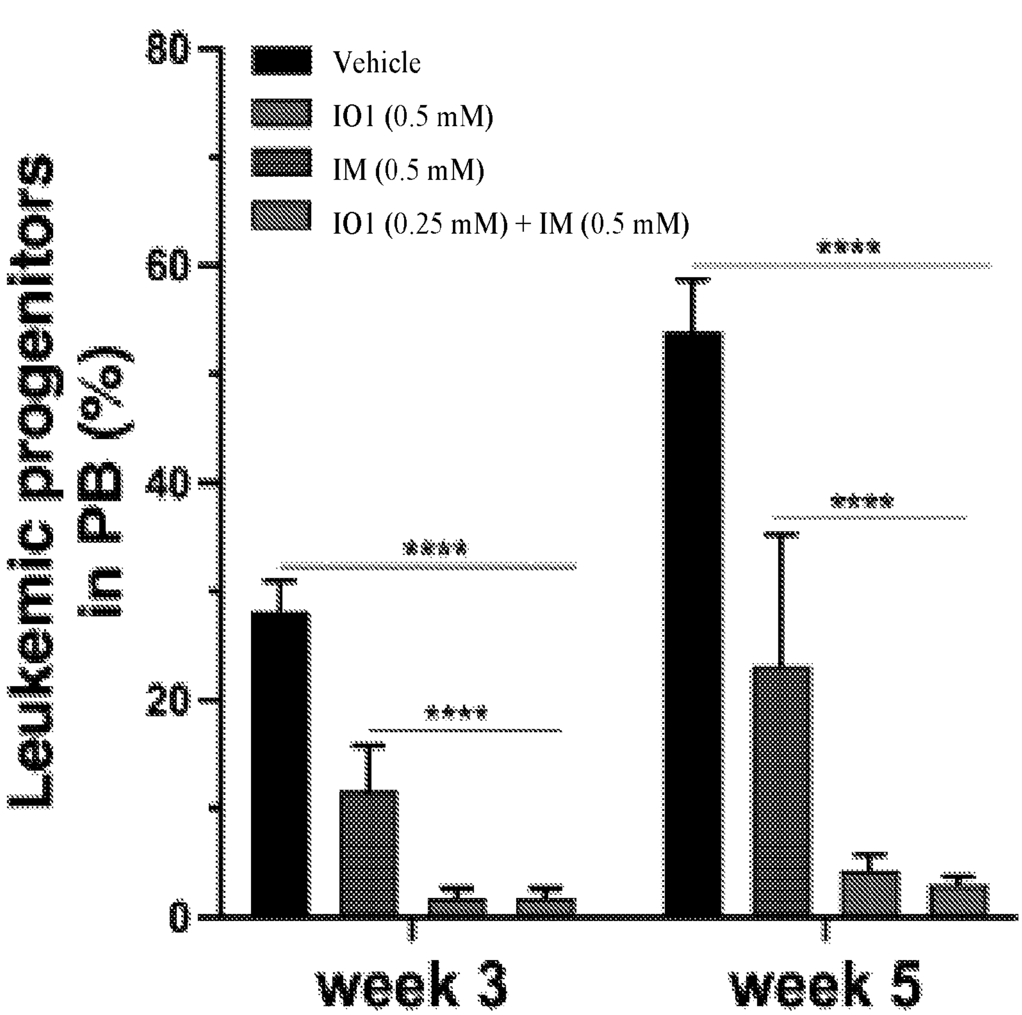
Figure 8G:
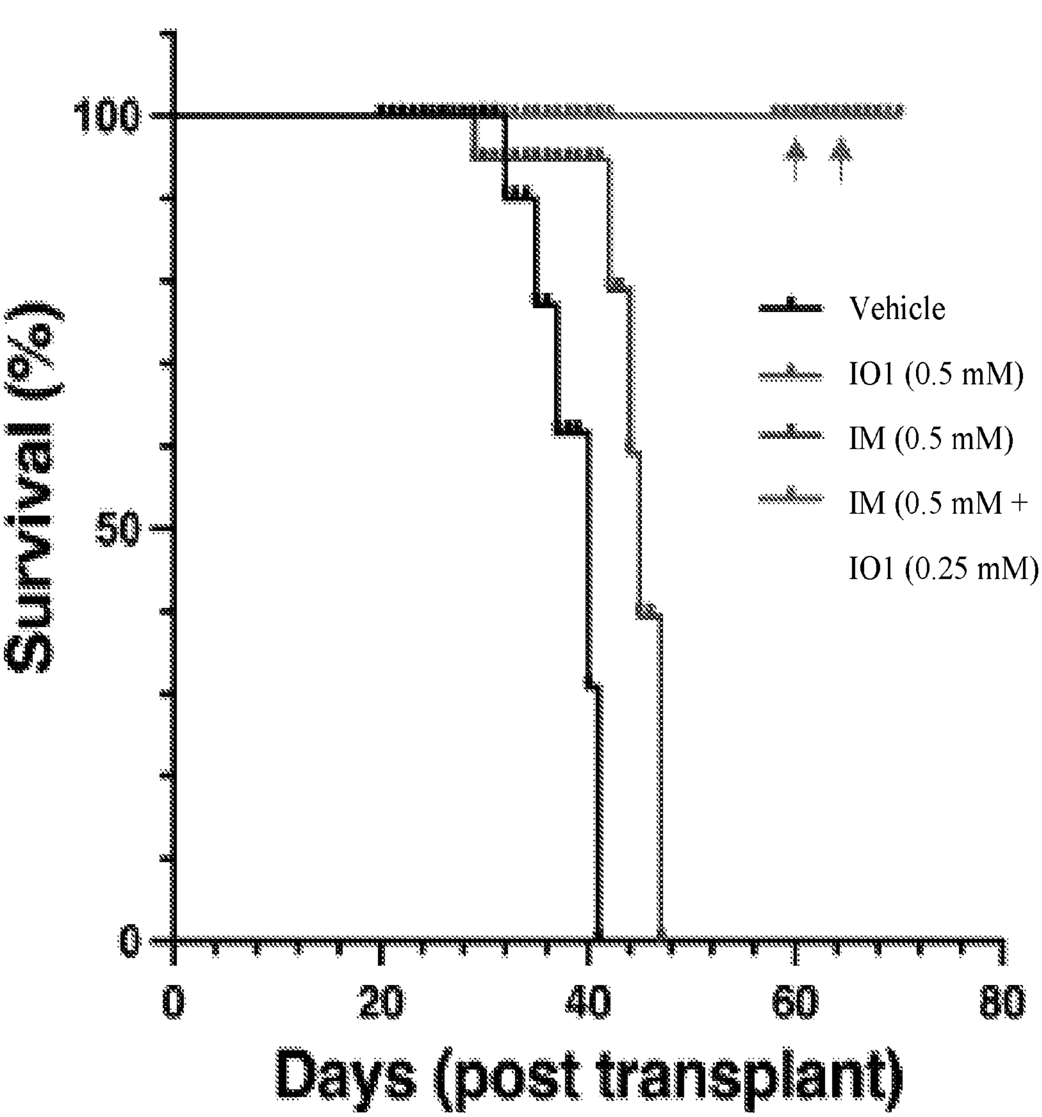
Figure 8H:
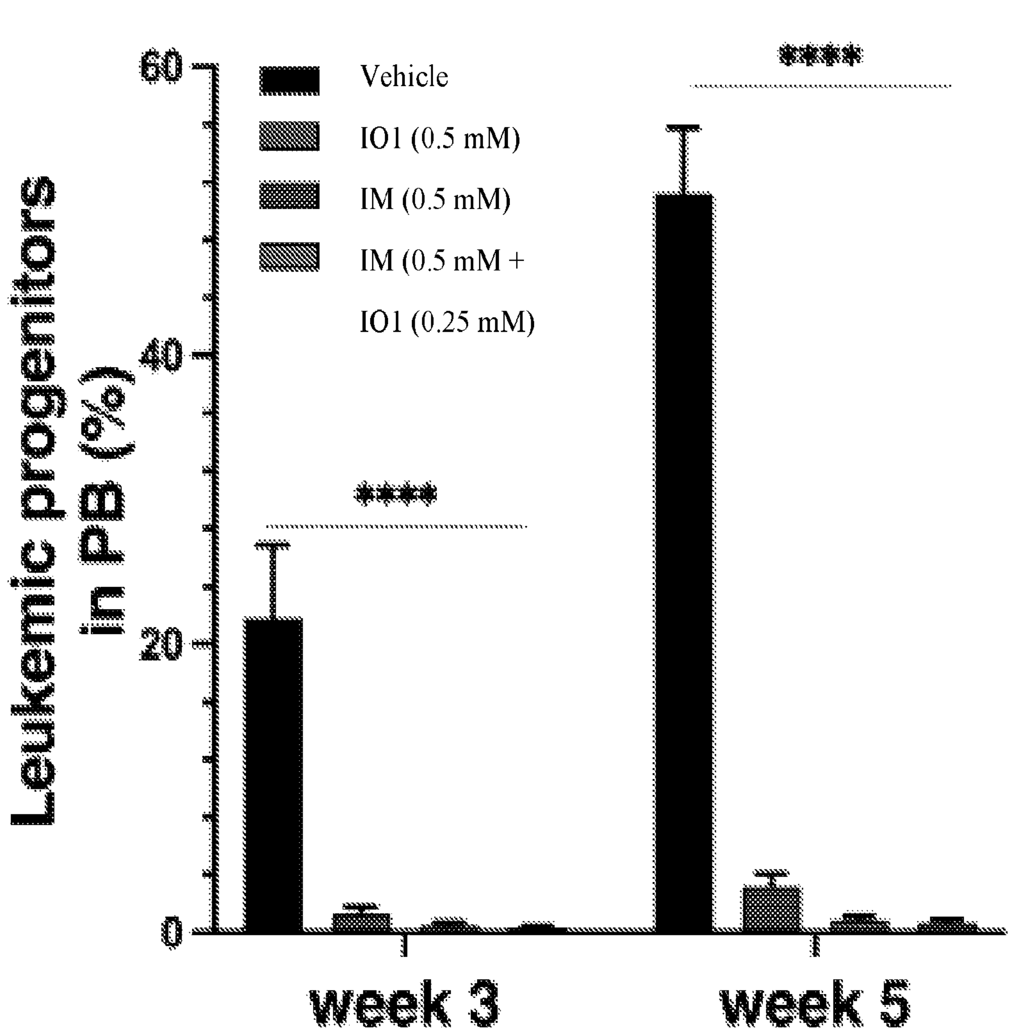
Figure 8I:
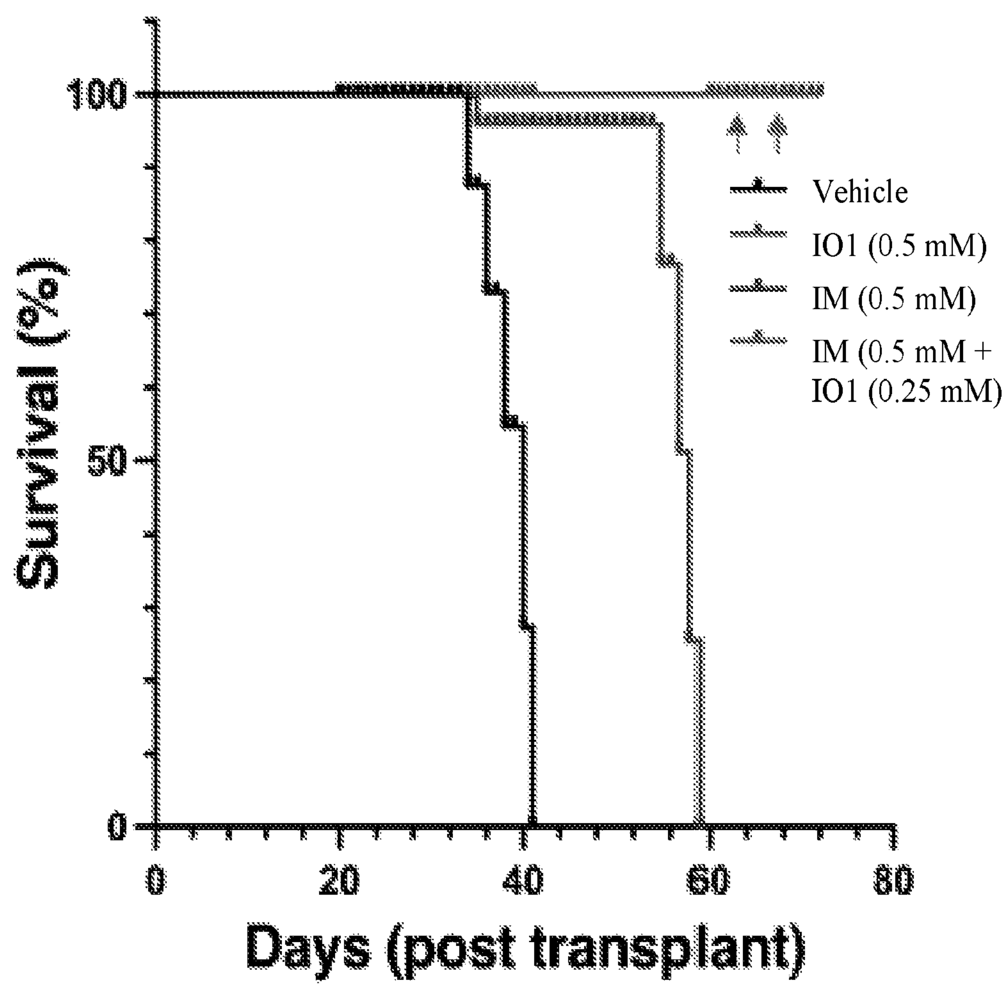
Figure 8J:
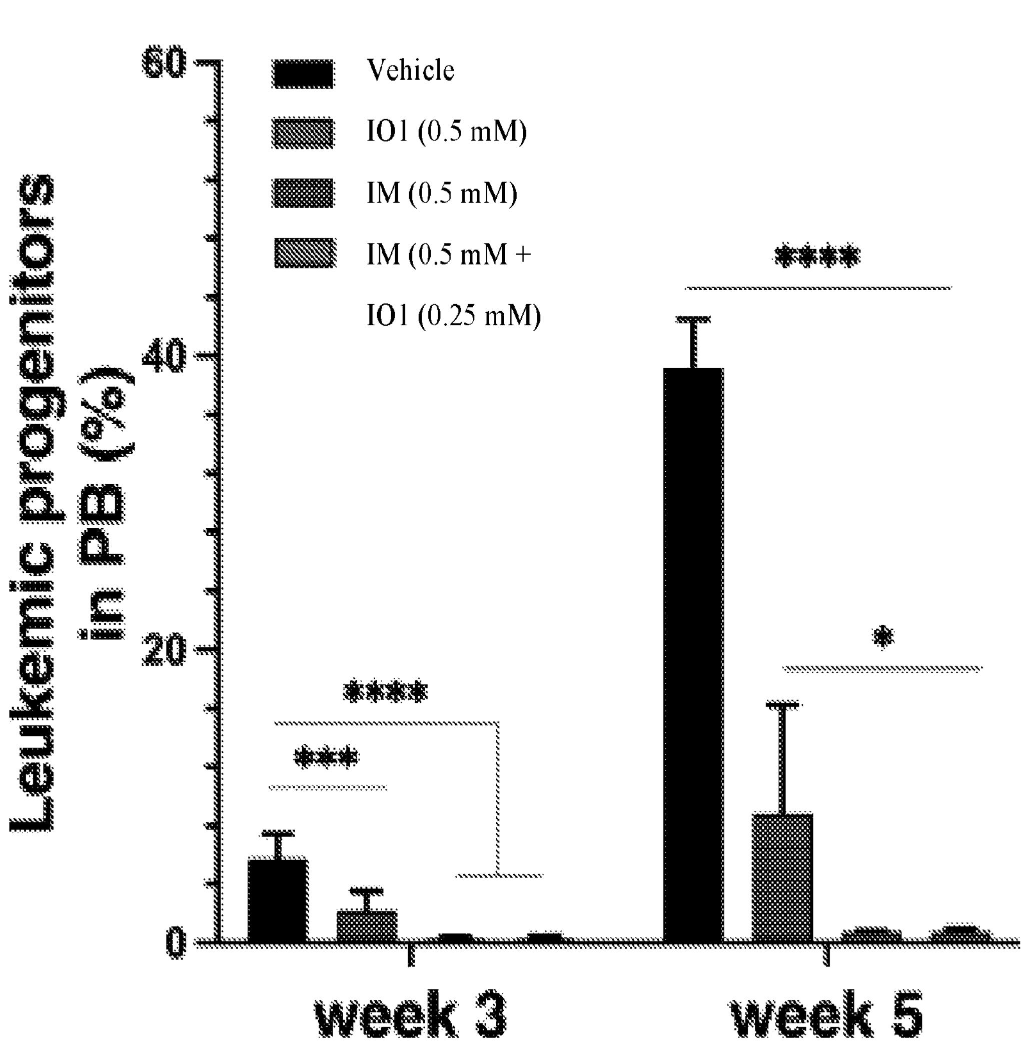

IODVA1 eradicates leukemic propagating activity assessed by serial transplantation. At the 3- and 5-week time points, leukemic progenitor cells ($EGFP^+/B220^+$) from the peripheral blood of secondary transplanted mice from FIG. 1D were analyzed by flow cytometry and plotted as percentage of total PB for the 106-cell dilution. FIG. 8F shows that unlike imatinib-treated mice where $EGFP^+/B220^+$ cells constituted 23.2±5.4% of B-cells 5 weeks post transplantation, IODVA1- and IODVA1+imatinib-treated mice had a 4.2±0.7 and 3.0±0.3%, respectively, $EGFP^+/B220^+$ leukemic B-cells at the same time-point. Similar trends in mice survival and leukemic burden were obtained for the higher dilutions (FIG. 8G-8J). Applicant previously evaluated IODVA1 for any hematological toxicity and detected no adverse changes in body weight or hematological parameters[4]. Together, these data indicate that IODVA1 eradicates all leukemogenic cells in vivo, including the ones responsible for propagation and possibly relapse and that IODVA1 is more efficient than imatinib at decreasing the leukemic cell burden.

IODVA1 does not affect p190-BCR-ABL1 phosphorylation status. p190-BCR-ABL1 expressing Ba/F3 cells were treated with IODVA1 (3 μM) or vehicle control for 4 h, lysed and immunoprecipitated using an anti-ABL1 antibody. The immune complex was separated on SDS-PAGE and blotted for pTyr. IODVA1 did not affect the phosphorylation level of p190-BCR-ABL1 (FIG. 9). Thus, IODVA1 does not target BCR-ABL1.

IODVA1 decreases RAC activity and downstream signaling. To determine the effective concentration that decreases RAC activation[5,6], Ba/F3 cells expressing p190-BCR-ABL1[7-9] were incubated with different concentrations of IODVA1 (0.1-10 μM) for 1 h, followed by GST-PAK-GBD pulldown. FIG. 10, A shows that IODVA1 decreases the levels of active RAC with an IC50 of 1 μM. Applicant also tested the activation of the two related GTPases, Cdc42 and Rho. IODVA1 (3 μM) decreases the levels of active Cdc42 by 60% at 15 min and totally inhibits it at 30 min incubation time. Pull-downs with the Rho-binding domain of Rhotekin show that IODVA1 has no effect on RhoA activation (FIG. 10B).

To determine the kinetics of IODVA1-promoted effector dephosphorylation, Applicant focused on the activity of the RAC pro-survival effectors PAK1/2 and the RAC pro-apoptotic member of the Bcl-2 family, BAD, a mediator of aggressive BCR-ABL1-expressing leukemia[10,11]. Applicant incubated p190-BCR-ABL1 expressing Ba/F3 cells with IODVA1 (3 μM) and determined phosphorylation levels indicative of activity of both effectors at early time points by immunoblot. The phosphorylation of the activation loop PAK1/2 T423/T402, a critical determinant for PAK1/2's enzymatic activity[12-14] is visible at the beginning of the treatment at t=0 and 2 min but decreases sharply beyond the 5 min treatment time (FIG. 10C). Thus, IODVA1 results in quick decrease in RAC and PAK1/2 activity in the leukemic model, consistent with previous observations in solid tumors[4]. The observed difference in deactivation times, i.e. 15 vs. 5 min, is likely due to the difference and sensitivity of the techniques used to detect the activation state of these proteins, e.g. pull-down followed by immunoblotting vs. direct immunoblotting. Similarly, IODVA1 decreased BAD S136 phosphorylation beyond the 15 min time point, indicative of an active or pro-cell death protein[15].

IODVA1 does not interfere with RAC-specific GAP or GDI functions. RAC activity and signaling[16-26] is regulated by RAC-specific GAPs, GDIs, and GEFs. Applicant argued that the decrease in RAC activity might be caused by IODVA1 targeting one RAC regulator. First, Applicant tested in vitro if IODVA1 stimulates the activity of the RAC negative regulator p50GAP. RAC was loaded with the fluorescently-labeled tamraGTP and the stimulated increase in GTP-hydrolysis by the C-terminal GAP homology of p50GAP was monitored by stopped-flow fast kinetics for 3 s. FIG. 10E shows that the initial decrease in fluorescence, which is coupled to GTP-hydrolysis, does not change in the presence ($k_{obs}$=5.7) or absence ($k_{obs}$=6.6) of high IODVA1 concentration (50 μM). Applicant thus concluded that IODVA1 does not stimulate the activity of p50GAP to explain the observed decrease in RAC activity.

Second, Applicant tested if IODVA1 increases the detachment of RAC1 from membranes thus making it unavailable for activation by GEFs. Applicant studied the displacement of prenylated RAC1-GDP from synthetic liposomes by GST-RhoGDI1 in the presence and absence of IODVA1 using liposome sedimentation assay[27]. GST-RhoGDI1 (4 μM) was added to liposome containing phosphatidylinositol 4,5-bisphosphate ($PIP_2$) and prenylated RAC1-GDP (1 μM) in the absence or presence of IODVA1 and further incubated on ice for 30 min. Samples were centrifuged at 20,000×g for 20 min at 4° C. and pellet (p) and supernatant(s) fractions were collected and immunoblotted for RAC1. Addition of IODVA1 (2 μM) did not affect prenylated-RAC1 displacement by RhoGDI1 from liposomes (FIG. 10,F, 2$^{nd}$ and 3$^{rd}$ lanes). Applicant then measured the interaction between fluorescently labeled RAC1 and RhoGDI1 using stopped-flow fast kinetics techniques. The stopped-flow data show that the observed binding affinity between the two proteins did not significantly change in the presence of IODVA1 ($k_d$=0.078 μM) or vehicle control ($k_d$=0.1 μM), even though the two proteins interact with a different amplitude (FIG. 10,G). Taken together, IODVA1 does not interfere with RhoGDI binding to RAC1 or with its ability to extract prenylated-RAC1 from $PIP_2$-containing membranes.

VAV3-deficient leukemic cells do not respond to IODVA1 in vitro and in vivo. To further validate VAV3 as target of IODVA1, Applicant studied the effects of IODVA1 on leukemic cells from the VAV3-deficient ($VAV3^{-/-}$) mice previously published[7,11,28]. Applicant argued that if IODVA1 targets VAV3, then $VAV3^{-/-}$ cells should be significantly less sensitive to its action. Applicant tested if the lack of response to IODVA1 by $VAV3^{-/-}$ cells holds in vivo. Applicant transplanted wild-type ($VAV3^{+/+}$) or $VAV3^{-/-}$ LDBM cells transduced with p190-BCR-ABL1 retrovirus into lethally irradiated C57BL/6 mice (N=5 per group), waited 21 days for the leukemia to develop, and treated the mice with either vehicle control or IODVA1 administered through osmotic pumps as before (FIG. 11, A). Because the mice died shortly post leukemia transplantation, only one pump was used in all groups, e.g. all treatments started at day 21 and ended by day 35. Kaplan-Meier survival plots show that, as expected, mice transplanted with wild-type leukemia and treated with vehicle control die between days 33 and 38. Mice treated with IODVA1 survive until day 60, i.e. 25 days after treatment has ended. Compared to mice receiving vehicle control where leukemic progenitors constituted 23.8% of peripheral blood cells, mice treated with IODVA1 showed drastic reduction of levels of leukemic progenitors to 5% and 2% after one week and two weeks of IODVA1 treatment, respectively (FIG. 11B). These in vivo data are consistent with FIG. 8E and with the hypothesis that IODVA1 eliminates leukemic progenitor cells responsible for disease propagation despite the short treatment time. Mice transplanted with $VAV3^{-/-}$ leukemia and treated with vehicle control or IODVA1 (FIG. 11A) die between days 34 and 42 and days 40 and 44, respectively. Thus, IODVA1 had no significant effect on $VAV3^{-/-}$ leukemic mice (p=0.41). $VAV3^{-/-}$ leukemic mice seem to have increased survival compared to their wild-type leukemic counterpart, but analysis showed weak statistical significance (p=0.1). This can also be seen in the level of peripheral blood leukemic progenitor cells that kept increasing in $VAV3^{-/-}$ leukemic mice treated with IODVA1 or vehicle control (FIG. 11B).

The observation that mice engrafted with $VAV3^{-/-}$ leukemia die by day 44 while mice engrafted with normal leukemia and treated with IODVA1 survive until day 60 even after treatment has ended suggests that $VAV3^{-/-}$ leukemia relies on VAV3- and IODVA1-independent pathways for survival. To test this hypothesis, Applicant studied by phospho-flow cytometry the activity of several effectors in BM cells from one-week treated mice. The phosphorylation levels of the VAV3/RAC effectors JNK and PAK1 are severely reduced in IODVA1-treated mice regardless of VAV3 status (FIG. 11, C). The levels of pJNK and pPAK1 in $VAV3^{-/-}$ leukemia are not affected by IODVA1 and are similar to IODVA1-treated wild-type leukemia. Interestingly, the phosphorylation levels of the non-VAV3/RAC effectors AKT and STAT3 are not only unaffected by IODVA1 in wild-type leukemia as seen before in FIGS. 2C & 3B but significantly increased in $VAV3^{-/-}$ leukemia. This observation suggests that in vivo, $VAV3^{-/-}$ leukemic cells are not only unresponsive to IODVA1 but rely among others on AKT and STAT3 signaling for survival.

IODVA1 decreases survival of patient-derived leukemia cells. Cells from PDX models representing pediatric $Ph^+$, Ph-like with a diverse series of genetic aberrations, and a few cases of MLL-rearranged B-ALL patients (Table 1) generally responded positively to IODVA1 ex vivo (FIG. 12).

$Ph^+$ B-ALL. Cells from patient #2017-58 with a dual $Ph^+$ (BCR-ABL1) and Ph-like (P2RY8-CRLF2) rearrangement were treated with ABL1-TKI dasatinib, JAK inhibitor ruxolitinib, dasatinib and ruxolitinib combination (das+rux), CDK-inhibitor abemaciclib, or IODVA1 (FIG. 12, A, left panel). These cells clearly responded to dasatinib, ruxolitinib, and the combination. IODVA1 was not as potent as it decreased their proliferation by only 40% at 1 UM and had no effect at 0.2 μM. Cells from relapsed patient #2018-136 with $Ph^+$ (BCR-ABL1), IKZF1, ΔCDKN2A/B, and ΔPAX5 were similarly treated. Dasatinib (20 nM) reduced the proliferation of #2018-136 cells by 56%; ruxolitinib or abemaciclib (0.1 μM) had no effect. The das+rux combination resulted in 63% decrease in proliferation, which is likely due to inhibitory action of dasatinib. IODVA1 (0.5 M) reduced the proliferation of these cells by 78%. When tested in the colony formation assay, IODVA1 (1 μM) reduced the number of colonies by 60% (p=0.001) (FIG. 12, A, middle panels).

Original $CD19^+$ cells from patient #2017-129 with $Ph^+$ (BCR-ABL1; T315I) and mutated SETD2, SF3B1, and TP53 who relapsed after initial treatment were treated with vehicle control, dasatinib, ruxolitinib, (das+rux), and IODVA1. As expected dasatinib, ruxolitinib, or the combination had no effect on proliferation of the $CD19^+$ cells (FIG. 12, A, right panel). In contrast, IODVA1 at 1 μM but not at 0.2 μM reduced the $CD19^+$ B-ALL cell counts by 80%. Additionally, Applicant confirmed that IODVA1 does not exert toxic effects to cells of normal stroma (FIG. 12, A, right panel arrows). Thus, IODVA1 decreases the proliferation of $Ph^+$ B-ALL (BCR-ABL1) primary cells including cells expressing the TKI-resistant T315I mutant consistent with Applicant's findings that $Ph^+$ B-ALL (BCR-ABL1) model cells express high-levels of VAV3.

The fact that #2017-58 cells did not respond to IODVA1 as well as the other two patient samples is probably due to the low VAV3 expression and level of phosphorylation (FIG. 7A) and the existence of other genetic mutations (e.g. P2RY8-CRLF2) that promote cell growth independently of VAV3.

Ph-like B-ALL. The cohort of samples contained numerous cases of Ph-like disease with a diverse series of genetic aberrations. Ph-like ALL is a high-risk subset of leukemia that shares many characteristics of $Ph^+$ B-ALL and contains a variety of genomic alterations that activate kinase and cytokine signaling but where BCR-ABL1 is not expressed [29-31]. Ph-like patient derived cells generally responded positively to the treatment they received (FIG. 12B). At 1 but not 0.2 μM, IODVA1 reduced cell proliferation by at least 95%. The exception was sample #2018-132 which did not respond to any treatment including the CDK4/6 selective inhibitor abemaciclib. IODVA1 (0.5 μM) reduced the proliferation of these cells by 25% similar to the other FDA approved drugs. Thus, IODVA1 decreases the proliferation of majority of Ph-like B-ALL primary cells despite their heterogenous genetic lesions.

MLL-rearranged B-ALL. Cells from #2018-190, an MLL/AF9 fusion, were also treated with the same drugs. FIG. 12C shows that these cells resisted dasatinib, ruxolitinib, and the combination. IODVA1 (0.5 μM) and abemaciclib (0.1 μM) decreased proliferation of these cells by 50 and 43%, respectively. Similarly, cells from relapsed patient #2016-116 with MLL t(1; 11), t(6; 6) responded very well to IODVA1 either with or without combined SCF/Flt3L/IL-7 cytokine supplementation.

Supplemental Methods

Plasmids, Cell Lines, and Reagents: Scrambled and VAV3-specific shRNAs (Sigma-Aldrich MISSION shRNA) were obtained from Cincinnati Children's Lenti-shRNA Library Core. Plasmid set for purification of fixed-arm carrier fusions pMalX (A-E) was a kind gift from Dr. Lars C. Pedersen (NIEHS), pET28b-$N_9$-MBP-mOrange plasmid was from Addgene (#29748), chaperone co-expression plasmid set was from TaKaRa (cat #3340). Primers were from Integrated DNA Technologies (IDT, Inc.). Restriction enzymes, polymerases, cloning assembly kits and competent cells were from New England Biolabs and Invitrogen.

MDA-MB-231 cells were maintained in IMEM (Invitrogen) supplemented with 10% FBS, 1% penicillin/streptomycin, and 1% amphotericin B. Ba/F3 cells were cultured in RPMI (GIBCO) supplemented with 10% FBS and IL-3 (10 ng/ml), NALM-1 cells were maintained in RPMI supplemented with 15% FBS. HEK293T cells were maintained with DMEM supplemented with 10% FBS and 1% penicillin/streptomycin. All cell lines were cultured at 37° C. in a 5% $CO_2$ humidified incubator. Cell viability was assessed by trypan blue exclusion assay as previously described[4]. Cytokines were from Peprotech.

The following antibodies were used: GAPDH (#627408, GeneTex), pERK1/2 (#4370), pAKT (#9271 and #9018), c-Abl (#2862), Cdc42 (#2462), RhoA (#2117), pPAK1/2 (#2601S), pS6 (#4851S), PAK1 (#2602S), pBAD (#4366), and BAD (#9292), anti-mouse HRP (#7076), anti-rabbit HRP (#7074) were from Cell Signaling Technologies, pVAV1 (Y174) (#ab76225), pVAV3 (Y173) (#ab109544), total VAV3 (#ab203315) were from Abcam. Total VAV3 antibody was also graciously shared by Dr. Xosé Bustelo's laboratory, pJNK (Alexa Fluor 647 conjugated, #562481), p-p38 (PE-conjugated, #612565), RAC2 (#610850), pSTAT3 (#55385), and pSTAT5 (Alexa Fluor 647 conjugated, #612599), and B220 APC-Cy7 antibody (#552094) were from BD Bioscience, anti-phosphotyrosine (Millipore Sigma) antibody was from Millipore Sigma (#05321), p4EBP1 (PE-conjugated, #12-9107-42) was from ThermoFisher. Anti-human CD19 APC-Cy7 (#363009) and anti-human CD45 FITC (#304005) were from BioLegend.

Lipids (Phosphatidylserine (PS), Phosphatidylcholine (PC), phosphatidylethanolamine (PE) and sphingomyelin (SM), and phosphatidylinositol 4,5-bisphosphate ($PIP_2$) for membrane displacement assays were from Avanti Polar Lipids.

IODVA1 and its biotinylated analog were synthesized by WuXi AppTech (Hong Kong) from 2-guanidinobenzimidazole and purified as described[4] but at 20° C. Imatinib methanesulfonate salt (#I-5508), dasatinib (#D-3307), and ponatinib (#P-7022) were from LC Laboratories, ruxolitinib (#S1378) from Selleck.

Viral Particle Production, Transduction and Transplantation: Production of lentivirus and retrovirus for stable transduction of murine and human cells were done as described previously[32]. Retroviral and lentiviral vectors, viral transduction of cell lines and mouse LDBM, and transplantation of transduced leukemic cells were previously described [11].

For VAV3 rescue experiments, low density bone marrow cells from wild-type ($VAV3^{+/+}$) or $VAV3^{-/-}$ mice were transduced with bicistronic retroviral vector encoding p190 BCR-ABL1-IRES-YFP and sorted for $YFP^+$ 48 h post-transduction. Cells were then transduced with lentiviral particles encoding either empty vector, full-length WT or mutant VAV3 (pCDH1-MCS1-EF1-copGFP). Cells were sorted for $GFP^+/YFP^+$ and treated with IODVA1 at the indicated concentrations. Cell cycle was analyzed at 18 h post BrdU incorporation.

Flow Cytometry Analysis: Red blood cells were removed from the peripheral blood samples using fixative-free lysis buffer (BD Pharm Lyse Cat #555899). After a single wash in PBS, cells were stained with anti-B220 APC-Cy7 antibody. Stained cells were washed once and analyzed by flow cytometry.

SDS-PAGE, Pull-down Assays and Immunoblotting: For analysis of GTPase status, exponentially growing cells, treated with either vehicle or IODVA1 at indicated concentrations and time points, were subjected to active GTPase pulldown kits using GST-PAK1-GBD or GST-Rhotekin (ThermoFisher). Protein complexes were separated on SDS-PAGE and immunoblotted with anti-RAC1, anti-Cdc42 and anti-RhoA antibodies. For analysis of VAV3 binding to biotinylated IODVA1, recombinant VAV3 or lysates from PDX specimens were subjected to neutravidin pulldowns, followed by SDS-PAGE and immunoblotting analyses.

For analysis of expression and cell signaling, cells were subjected to lysis and immunoblotting, as described previously[11,32]. Relative signals were normalized to the unstimulated conditions after normalization to the total protein amount. Quantification was performed using Li-COR Image Studio or ImageJ (NIH).

Recombinant Protein Cloning, Expression and Purification: Human RAC1 (GenBank accession n° NM_006908.4) was subcloned as N-terminally $His_6$-tagged construct into pFastBacHTB vector (Invitrogen). Full-length human RAC1 was purified from baculovirus. RAC1 was produced in TNAO38 insect cells and purified using Ni-IMAC chromatography.

RhoGDI Extracting Prenylated RAC1 from Liposomes: Displacement of prenylated-RAC1-GDP from synthetic liposomes by GST-RhoGDI1 in the presence and absence of IODVA1 was studied using liposome sedimentation assay as described[27]. Briefly, liposomes were generated by using a defined composition of lipids (194 μg) containing 39% w/w phosphatidylethanolamine, 16% w/w phosphatidylcholine, 36% w/w phosphatidylserine, 4% sphingomyelin, and 5% w/w phosphatidylinositol 4,5-bisphosphate. Prenylated RAC1-GDP (1 μM) was added to liposomes suspended in protein buffer (20 mM Hepes, pH 7.4, 150 mM NaCl, 5 mM $MgCl_2$, 3 mM DTT) and incubated for 20 min on ice. GST-RHOGDI1 (2 μM) in the absence or presence of IODVA1 was added to the liposome/prenylated RAC1 and further incubated on ice for 30 min. The samples were then centrifuged at 20,000×g for 20 min at 4° C. Pellet and supernatant fractions were collected, separated on SDS-PAGE and immunoblotted for RAC1.

Stopped-flow Spectrometry: GTPase assay and nucleotide exchange reaction were performed with a Hi-Tech Scientific (SF-61) stopped-flow instrument as described [33] The excitation wavelengths were 543 nm and 362 nm for tamraGTP and mantGppNHp, respectively. For GTPase assay, equal volumes (600 μl) of 0.2 μM RAC1-tamraGTP and 10 μM of p50GAP were used. GTPase assay as well the protein-protein interaction were performed in presence of 5% DMSO.

SUPPLEMENTAL REFERENCES

1. Warmuth, M., Kim, S., Gu, X. J., Xia, G. & Adrian, F. Ba/F3 cells and their use in kinase drug discovery. *Curr Opin Oncol* 19, 55-60 (2007).
2. Sonta, S. I., Minowada, J., Tsubota, T. & Sandberg, A. A. Cytogenetic study of a new Ph1-positive cell line (NALM-1). *J Natl Cancer Inst* 59, 833-7 (1977).
3. Williams, D. A. et al. Dominant negative mutation of the hematopoietic-specific Rho GTPase, Rac2, is associated with a human phagocyte immunodeficiency. *Blood* 96, 1646-54 (2000).
4. Gasilina, A. et al. IODVA1, a guanidinobenzimidazole derivative, targets Rac activity and Ras-driven cancer models. *PLOS One* 15, e0229801 (2020).
5. Nieborowska-Skorska, M. et al. Rac2-MRC-cIII-generated ROS cause genomic instability in chronic myeloid leukemia stem cells and primitive progenitors. *Blood* 119, 4253-63 (2012).
6. Wei, J. et al. Microenvironment determines lineage fate in a human model of MLL-AF9 leukemia. *Cancer Cell* 13, 483-95 (2008).
7. Thomas, E. K., Cancelas, J. A., Zheng, Y. & Williams, D. A. Rac GTPases as key regulators of p210-BCR-ABL-dependent leukemogenesis. *Leukemia* 22, 898-904 (2008).
8. Harnois, T. et al. Differential interaction and activation of Rho family GTPases by p210bcr-abl and p190bcr-abl. *Oncogene* 22, 6445-54 (2003).
9. Sahay, S. et al. The RhoGEF domain of p210 Bcr-Abl activates RhoA and is required for transformation. *Oncogene* 27, 2064-71 (2008).
10. Mizukawa, B. et al. Inhibition of Rac GTPase signaling and downstream prosurvival Bcl-2 proteins as combination targeted therapy in MLL-AF9 leukemia. *Blood* 118, 5235-45 (2011).
11. Chang, K. H. et al. Vav3 collaborates with p190-BCR-ABL in lymphoid progenitor leukemogenesis, proliferation, and survival. *Blood* 120, 800-11 (2012).
12. Yu, J. S., Chen, W. J., Ni, M. H., Chan, W. H. & Yang, S. D. Identification of the regulatory autophosphorylation site of autophosphorylation-dependent protein kinase (auto-kinase). Evidence that auto-kinase belongs to a member of the p21-activated kinase family. *Biochem J* 334 (Pt 1), 121-31 (1998).
13. Zenke, F. T., King, C. C., Bohl, B. P. & Bokoch, G. M. Identification of a central phosphorylation site in p21-activated kinase regulating autoinhibition and kinase activity. *J Biol Chem* 274, 32565-73 (1999).
14. Gatti, A., Huang, Z., Tuazon, P. T. & Traugh, J. A. Multisite autophosphorylation of p21-activated protein kinase gamma-PAK as a function of activation. *J Biol Chem* 274, 8022-8 (1999).
15. Zha, J., Harada, H., Yang, E., Jockel, J. & Korsmeyer, S. J. Serine phosphorylation of death agonist BAD in response to survival factor results in binding to 14-3-3 not BCL-X(L). *Cell* 87, 619-28 (1996).
16. Jaffe, A. B. & Hall, A. Rho GTPases: biochemistry and biology. *Annu Rev Cell Dev Biol* 21, 247-69 (2005).
17. Loirand, G. & Pacaud, P. The role of Rho protein signaling in hypertension. *Nat Rev* Cardiol 7, 637-47 (2010).
18. Newey, S. E., Velamoor, V., Govek, E. E. & Van Aelst, L. Rho GTPases, dendritic structure, and mental retardation. *J Neurobiol* 64, 58-74 (2005).
19. Vigil, D., Cherfils, J., Rossman, K. L. & Der, C. J. Ras superfamily GEFs and GAPs: validated and tractable targets for cancer therapy? *Nat Rev Cancer* 10, 842-57 (2010).
20. Zandvakili, I., Lin, Y., Morris, J. C. & Zheng, Y. Rho GTPases: Anti- or pro-neoplastic targets? *Oncogene* 36, 3213-3222 (2017).
21. Coleman, M. L., Marshall, C. J. & Olson, M. F. RAS and RHO GTPases in G1-phase cell-cycle regulation. *Nat Rev Mol Cell Biol* 5, 355-66 (2004).
22. Kiosses, W. B., Shattil, S. J., Pampori, N. & Schwartz, M. A. Rac recruits high-affinity integrin alphavbeta3 to lamellipodia in endothelial cell migration. *Nat Cell Biol* 3, 316-20 (2001).

23. Sundaresan, M. et al. Regulation of reactive-oxygen-species generation in fibroblasts by Rac1. *Biochem J* 318 (Pt 2), 379-82 (1996).
24. Bustelo, X. R. RHO GTPases in cancer: known facts, open questions, and therapeutic challenges. *Biochem Soc Trans* 46, 741-760 (2018).
25. Ridley, A. J. Rho GTPase signalling in cell migration. *Curr Opin Cell Biol* 36, 103-12 (2015).
26. Steffen, A. et al. Rac function is crucial for cell migration but is not required for spreading and focal adhesion formation. *J Cell Sci* 126, 4572-88 (2013).
27. Zhang, S. C. et al. Liposome reconstitution and modulation of recombinant prenylated human Rac1 by GEFs, GDI1 and Pak1. *PLOS One* 9, e102425 (2014).
28. Thomas, E. K. et al. Rac guanosine triphosphatases represent integrating molecular therapeutic targets for BCR-ABL-induced myeloproliferative disease. *Cancer Cell* 12, 467-78 (2007).
29. Tasian, S. K., Loh, M. L. & Hunger, S. P. Philadelphia chromosome-like acute lymphoblastic leukemia. *Blood* 130, 2064-2072 (2017).
30. Roberts, K. G. & Mullighan, C. G. Genomics in acute lymphoblastic leukaemia: insights and treatment implications. *Nat Rev Clin Oncol* 12, 344-57 (2015).
31. Pui, C. H., Roberts, K. G., Yang, J. J. & Mullighan, C. G. Philadelphia Chromosome-like Acute Lymphoblastic Leukemia. *Clin Lymphoma Myeloma Leuk* 17, 464-470 (2017).
32. Lee, L. H. et al. Real-time genomic profiling of histiocytoses identifies early-kinase domain BRAF alterations while improving treatment outcomes. *JCI Insight* 2, e89473 (2017).
33. Nouri, K. et al. IQGAP1 Interaction with RHO Family Proteins Revisited: KINETIC AND EQUILIBRIUM EVIDENCE FOR MULTIPLE DISTINCT BINDING SITES. *J Biol Chem* 291, 26364-26376 (2016).

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. All accessioned information (e.g., as identified by PUBMED, PUBCHEM, NCBI, UNIPROT, or EBI accession numbers) and publications in their entireties are incorporated into this disclosure by reference in order to more fully describe the state of the art as known to those skilled therein as of the date of this disclosure. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

SEQUENCE LISTING

```
Sequence total quantity: 3
SEQ ID NO: 1            moltype = AA  length = 4
FEATURE                 Location/Qualifiers
source                  1..4
                        mol_type = protein
                        organism = unidentified
SEQUENCE: 1
AAAA                                                              4

SEQ ID NO: 2            moltype = AA  length = 7
FEATURE                 Location/Qualifiers
source                  1..7
                        mol_type = protein
                        organism = unidentified
SEQUENCE: 2
AAAASEF                                                           7

SEQ ID NO: 3            moltype = AA  length = 9
FEATURE                 Location/Qualifiers
source                  1..9
                        mol_type = protein
                        organism = unidentified
SEQUENCE: 3
AAAASEFGS                                                         9
```

What is claimed is:

1. A method of treating an individual having a leukemia comprising administering a compound having the structure (IODVA1)

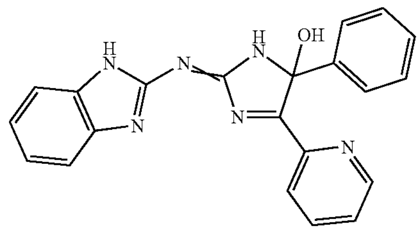

or a tautomer, pharmaceutically acceptable salt, solvate, or hydrate thereof to the individual; and administering ponatinib to the individual.

2. The method of claim 1, the compound being administered at one or more time points selected from prior to administration of the ponatinib, concurrent with administration of the ponatinib, or following administration of the ponatinib.

3. The method of claim 1, the compound IODVA1 being administered via one or more routes selected from orally and intravenously.

4. The method of claim 1, the ponatinib being administered via one or more routes selected from orally and intravenously.

5. The method of claim 1, the leukemia being selected from a Tyrosine Kinase Inhibitor resistant (TKI-resistant) leukemia, a TKI-resistant Ph+B-ALL, Chronic Myelogenous Leukemia (CML), Ph-Positive Acute Lymphoblastic Leukemia (ALL), Ph-like ALL, Chronic Myeloid Leukemia, Resistant Chronic Phase Chronic Myeloid Leukemia (CP-CML), MLL-rearranged B-ALL, and combinations thereof.

6. The method of claim 1, wherein the leukemia is not a RAC-deficient leukemia.

7. The method of claim 1, wherein the leukemia is a VAV3 positive leukemia.

8. The method of claim 1, the individual having a p210-BCR-ABL1(T3151) mutation.

9. The method of claim 1, the individual being a pediatric individual.

* * * * *